US006287564B1

(12) United States Patent
Wagter-Lesperance et al.

(10) Patent No.: US 6,287,564 B1
(45) Date of Patent: Sep. 11, 2001

(54) METHOD OF IDENTIFYING HIGH IMMUNE RESPONSE ANIMALS

(76) Inventors: Lauraine Wagter-Lesperance, 120 Milcrest Way, S.W., Calgary, Alberta (CA), T2Y 2J6; Bonnie Mallard, 12 Atchison Lane, Fergus, Ontario (CA), N1M 3K1

( * ) Notice: Subject to any disclaimer, the term of this patent is extended or adjusted under 35 U.S.C. 154(b) by 0 days.

(21) Appl. No.: 09/215,328

(22) Filed: Dec. 18, 1998

Related U.S. Application Data
(60) Provisional application No. 60/068,750, filed on Dec. 24, 1997.

(51) Int. Cl.$^7$ .................................................. A61K 39/00

(52) U.S. Cl. ........................................ 424/184.1; 424/9.1

(58) Field of Search ................................... 424/184.1, 9.1

(56) References Cited

FOREIGN PATENT DOCUMENTS

WO94/14064    6/1994  (WO) .

OTHER PUBLICATIONS

Wagter et al. *J. Dairy Science*, 1996, 79 (suppl. 1):119.
Biozzi, G.; Stiffel, C.; Mouton, D.; Bouthillier, Y.; Decreusefond, C. "Cytodynamics of the Immune Response in Two Lines of Mice Genetically Selected for "High" and "Low" Antibody Synthesis", The Journal of Experimental Medicine, 1972, 135:1071–1094.
Burton, J.L.; Burnside, E.B.; Kennedy, B.W.; Wilkie, B.N.; Burton, J.H. "Antibody Response to Human Erythrocytes and Ovalbumin as Marker Traits of Disease and Resistance in Dairy Calves", J. Dairy Science, 1989, 72:1252–1265.
Corbeil, L.B.; Watt, B.; Corbeil, R.R., Betzen, T.G.; Brownson, R.K.; Morill, J.L. "Immunoglobulin Concentrations in Serum and Nasal Secretions of Calves at the Onset of Pneumonia", 1984, American Journal of Veterinary Research, 1984, 45:773–778.
Dekkers, J.C.M.; Boettcher, P.J.; Mallard, B.A. "Genetic Improvement of Udder Health", Proc. 6$^{th}$ World Congress on Genetics Applied to Livestock Production, 1998, vol. 27.
Detilleux, J.C.; Koehler, K.J.; Freeman, A.E.; Kehrli, M.E.; Kelley, D.H. "Immunological Parameters of Periparturient Holstein Cattle: Genetic Variation", J. Dairy Sci., 1994, 77:2640–2650.
Detilleux, J.C.; Kehrli, M.E.; Freeman, A.E.; Fox, L.K.; Kelley, D.H. "Mastitis of Periparturient Holstein Cattle: A Phenotype and Genetic Study", J. Dairy Sci., 1995, 78:2285–2293.
Detilleux, J.C.; Kehrli, M.E.; Stabel, J.R.; Freeman, A.E.; Kelley, D.H. "Study of Immunological Dysfunction in Periparturient Holstein Cattle Selected for High and Average Milk Production", Veterinary Immunology and Immunopathology, 1995, 44:251–267.

Griffin, J.F.T. "Stress and Immunity: A Unifying Concept", Veterinary Immunology and Immunopathology, 1989, 20:263–312.
Harp, J.A.; Kehrli, M.E.; Hurley, D.J.; Wilson, R.A., Boone, T.C. "Numbers and Percent of T Lymphocytes in Bovine Peripheral Blood During the Periparturient Period", Veterinary Immunology and Immunopathology, 1991, 28:29–35.
Hoshino, S.; Wakita, M.; Kobayashi, Y.; Sakauchi, R.; Nishiguchi, Y.; Ozawa, A.; Hodate, K.; Hamaguchi, I.; Yotani, Y. "Variations in Serum Levels of Insulin–like Growth Factor–1, Growth Hormone and Thyroid Hormones During Lactation in Dairy Cows", Comparative Biochemistry and Physiology, 1991, 99A:61–64.
Kehrli, M.E. Jr.; Nonnecke, B.J.; Roth, J.A. "Alterations in Bovine Lymphocyte Function During the Periparturient Period", American Journal of Veterinary Research, 1989, 50:215–220.
Kehrli, M.E. Jr.; Weigel, K.A.; Freeman, A.E.; Thurston, J.R.; Kelley, D.H. "Bovine Sire Effects on Daughters' In Vitro Blood Neutrophil Functions, Lymphocyte Blastogenesis, Serum Complement and Conglutinin Levels", Veterinary Immunology and Immunopathology, 1991, 27:303–319.
Kelley, K.W., "The Role of Growth Hormone in Modulation of the Immune Response", Annals New York Academy of Sciences, 1990, 594:95–103.
Khansari, D.N.; Murgo, A.J.; Faith, R.E. "Effects of Stress on the Immune System", Immunology Today, 1990, 11:170–175.
Mallard, B.A.; Wilkie, B.N.; Kennedy, B.W.; Gibson, J.; Quinton, M. "Immune Responsiveness In Swine: Eight Generations of Selection for High and Low Immune Response in Yorkshire Pigs", Proc. 6$^{th}$ World Congress on Genetics Applied to Livestock Production, 1998, 27:257–264.
Mallard, B.A.; Wilkie, B.N.; Kennedy, B.W.; Quinton, M. "Use of Estimated Breeding Values in a Selection Index to Breed Yorkshire Pigs for High and Low Immune and Innate Resistance Factors", Animal Biotechnology, 1992, 3:257.
Mallard, B.A.; Ireland, M.J.; Lacey, C.; Sharif, S.; Wagter, L. "Immunogenetic Markers to Enhance Immune Response and Disease Resistance of Periparturient Holstein Cows, 76$^{th}$ Conference on Research Workers in Animal Disease", Nov. 13–14, 1995.
Mallard, B.A.; Dekkers, J.C.; Ireland, M.J.; Leslie, K.E.; Sharif, S.; Lacey, C.; Van Kampen, L.; Wagter, L.; Wilkie, B.N. "Alteration in Immune Responsiveness During the Peripartum Period and its Ramification on Dairy Cow and Calf Health", J. Diary Sci., 1998, 81:585–595.

(List continued on next page.)

*Primary Examiner*—Patrick J. Nolan
(74) *Attorney, Agent, or Firm*—Bereskin & Parr; Micheline Gravelle

(57) ABSTRACT

The invention relates to a method and use of a method of identifying high immune response animals under stress. The animals are identified by a ranking procedure that classifies the animal's immune response to an antigen over a period of time that spans the stress.

5 Claims, 15 Drawing Sheets

OTHER PUBLICATIONS

Mallard, B.A.; Wagter, L.C.; Ireland, M.J.; Dekkers, J.C.M. "Effects of Growth Hormone, Insulin–like Growth Factor–I, and Cortisol on Pariparturient Antibody Response Profiles of Dairy Cattle", Veterinary Immunology and Immunopathology, 1997, 60:61–76.

Nagahata, H.; Ogawa, A.; Sanada, Y.; Noda, H.; Yamamoto, S. "Peripartum Changes in Antibody Producing Capability of Lymphocytes from Dairy Cows", Veterinary Quarterly, 1992, 14:39–40.

Van Kampen, C.; Mallard, B.A. "Effects of Peripartum Stress and Health on Circulating Bovine Lymphocyte Subsets", Veterinary Immunology and Immunopathology, 1997, 59:79–91.

Wagter, L.; Ireland, M.J.; Mallard, B.A. "Feasibility of Genetic Selection for Enhanced Disease and Stress Resistance: Effects if Periparturient Stress on Hormone and Immune Response Profiles of Holstein Cows", $4^{th}$ IVIS, Jul. 16–20, 1995.

Wagter, L.C.; Mallard, B.A.; Dekkers, J.C.M.; Leslie, K.E.; Wilkie, B.N. "Phenotypic Variation of Immune Response Profiles and Disease Occurrence During the Peripartum Period", ADSA Meeting, Jun. 22–25, 1997.

Sordillo, L.M.; Redmond, M.J.; Campos, M.; Warren, L.; Babiuk, L.A. "Cytokine Activity in Bovine Mammary Gland Secretions During the Periparturient Period", Canadian Journal of Veterinary Research, 1991, 55:298–301.

Week relative to calving

Antibody Response Group

Week relative to calving

METHOD OF IDENTIFYING HIGH IMMUNE RESPONSE ANIMALS

This application claims priority to U.S. Provisional Application No. 60/068,750, filed Dec. 24, 1997.

FIELD OF THE INVENTION

The invention relates to a method of identifying and breeding high immune response animals within a population of animals under stress, such as during peripartum.

BACKGROUND OF THE INVENTION

It has been found that there is an association between stress and disease occurrence in animals (T. Molitor and L. Schwandtdt, "Role Of Stress On Mediating Disease In Animals", Proc. Stress Symposia: Mechanisms, Responses, Management. Ed., N. H. Granholm, South Dakota State University Press, Apr. 6–7, 1993). Further it has been suggested that stress can lead to a compromised immune system. (T. Molitor and L. Schwandtdt, "Role Of Stress On Mediating Disease In Animals", Proc. Stress Symposia: Mechanisms, Responses, Management. Ed., N. H. Granholm, South Dakaota State University Press, Apr. 6–7, 1993/ Morrow-Tesch J. L. et al. 1996 J. Therm. Biol. 21(2):101–108) This can have significant effect on populations of animals such as commercial livestock including cattle, pigs, poultry, horses, and fish, wherein stress can be related to growth inhibition, infertility, and decreased milk or egg production (where applicable). It has been shown that the peripartum period or periparturition, in animals is a period of stress. (L. G. Johnson, "Temperature Tolerance, Temperature Stress, and Animal Development", Proc. Stress Symposia: Mechanisms, Responses, Management. Ed., N. H. Granholm, South Dakota State University Press, Apr. 6–7, 1993; J. J. McGloner, "Indicators Of Stress In Livestock And Implications For Advancements In Livestock Housing", Proc. Stress Symposia, : Mechanisms, Responses, Management. Ed., N. H. Granholm, South Dakota State University Press, Apr. 6–7, 1993; T. Molitor and L. Schwandtdt, "Role Of Stress On Mediating Disease In Animals", Proc. Stress Symposia: Mechanisms, Responses, Management. Ed., N. H. Granholm, South Dakaota State University Press, Apr. 6–7, 1993; M. J. C. Hessing et al, "Social Rank And Disease Susceptibility In Pigs", Vet Immunol. Immunopath 43:373–387, 1994; F. Blecha, "Immunoligcal Reactions Of Pigs Regrouped At Or Near Weaning", Am. J. Vet. Res. 46(9): 1934–1937, 1985; D. L. Thompson et al., "Cell Mediated Immunity In Marek's Disease Virus-Infected Chickens Genetically Selected For High and Low Concentrations Of Plasma Corticosterone", Am. J. Vet. Res. 41(1):91–96, 1980; Kehrli, H. E. et al., 1989a & b, Am. J. Vet. Res. 50(2):207 and 215).

Impairment of bovine host defense during the peripartum period may be associated with high concurrent disease occurrence. Impaired resistance may be due to endocrine factors associated with metabolic and physical changes occurring during gestation, parturition and lactation (Smith et al., 1973; Guidry et al., 1976; Burton et al., 1993). Infectious diseases of the peripartum period include mastitis, metritis and pneumonia. Metabolic and some reproductive diseases also predominate during this period and include retained placenta, milk fever, ketosis, and displaced abomasum. Mastitis is the most economically relevant disease. Estimated annual losses from mastitis are $35 billion (U.S) worldwide (Giraudo et al. 1997), $2 billion (U.S.) in the United States (Harmon, 1994) and $ 17 million (Can.) in Canada ($140–300 Can./cow) (Zhang et al., 1993).

Mastitis is an inflammation of the mammary gland characterized by local and systemic responses (Burvenich et al., 1994). Mastitis can be clinical or subclinical, when signs are not directly observable, but somatic cell counts in milk (SCC) increase and overall production performance decreases. Mastitis is caused by a number of Gram positive and Gram negative bacteria which are either major or minor pathogens. Major pathogens induce the greatest compositional changes in milk and have the greatest economic impact (Harmon, 1994). They include *Staphylococcus aureus, Escherichia coli, Streptococcus agalactiae*, Klebsiella spp., and others, while minor pathogens include coagulase negative staphylococci, and *Corynebacterium bovis*. The incidence of udder infection and clinical mastitis is usually highest at parturition and during early lactation (Smith et al., 1985). Coliforms such as *E. coli* and Klebsiella are the most common major pathogen during this period. Since coliform mastitis is difficult to treat, natural defence mechanisms of the mammary gland have been investigated in pursuit of control procedures (Burvenich et al., 1994). Coliform mastitis may be peracute and fatal, or subclinical. Most commonly it is acute clinical mastitis, with local and systemic signs of disease. Coliforms are Gram-negative microorganisms from the family Enterobacteriaceae which include important species from the genera Escherichia, Klebsiella, Enterobacter, Citrobacter and Proteus (Harmon, 1994; Kremer et al., 1994). The structure of the cell wall of coliform bacteria plays an important role in the virulence of the bacteria and subsequently in the pathogenesis of mastitis. The cell wall of *E. coli* has an inner cytoplasmic membrane, a peptidoglycan layer, an outer membrane that consists of two layers: a phospholipid protein layer and an outer lipopolysaccharide layer (LPS), and finally some strains possess an additional capsular polysaccharide layer. The LPS layer has three components: the O-specific polysaccharide chain, a polysaccharide core, and lipid A. Lipid A mediates the biological properties of LPS (endotoxin). Endotoxemia causes clinical signs of disease including high fever, drowsiness, appetite loss, dehydration, loss in milk production, cardiovascular failure, shock and often death (Kremer et al., 1994; Burvenich et al., 1994). Factors which contribute to susceptibility to mastitis include the complex environment (pasture, bedding, cleanliness of holding areas), management (milking practices, antibiotic therapy during lactation and dry-off) and physical trauma to the teat and/or udder (Cullor, 1995).

Various attempts have been made to develop vaccines against *S. aureus* as a treatment for mastitis, but without success. Vaccines have included toxoid, protein A, capsule and fibronectin in varying combinations and concentrations (reviewed by Sordillo, 1995). While these preparations may reduce the severity and duration of mastitis, new infections are not prevented. Inclusion of capsular polysaccharide in vaccine preparation slightly reduced the rate of new infection (Watson and Schwartskoff, 1990). More recently, the combination of a crude extract of *S. aureus* exopolysaccharides and inactivated unencapsulated *S. aureus* and Streptococcus spp. in a vaccine decreased incidence of intramammary infections caused by *S. aureus* (Giraudo et al., 1997). Newer vaccines against environmental coliforms contain rough or R-mutants of *E. coli* or *Salmonella typhimurium*. The surface core antigens of these mutants induces formation of cross-protective antibody that provides protection against various gram-negative diseases of animals including mastitis and calf scours. (Parker et al., 1994). These vaccines decrease incidence and severity of clinical disease but do not affect prevalence of coliform infections (Sordillo, 1995).

Direct selection for disease resistance may be done either by selecting the most disease-resistant breeding stock under normal environmental conditions, or by challenging the breeding stock with specific pathogens (Hutt, 1959). Indirect selection is based on identification of reliable indirect markers of disease resistance (Detilleux et al., 1993). Phenotypic indicators include morphological markers (eg. eye margin pigmentation in bovine infectious keraconjunctivitis), physiological markers (eg. hemoglobin type in malaria), and innate or immune response traits (eg. PMN function, antibody response and CMI). Genotypic indicators include candidate genes (eg. MHC genes, Ig genes, TcR genes), and anonymous molecular genetic markers (eg. RFLPs, tandem repeats loci, microsatellite loci) (Detilleux et al., 1993).

Experiments using immune response variation as selection criteria have been successful at directing response to be high or low (Biozzi et al., 1968; Ibanez et al., 1980; Siegel et al., 1980; Van der Zijpp et al., 1983; and Mallard et al., 1992). The continuous distribution antibody response suggests that response is under multigenic control (Puel and Mouton, 1996) and that characteristic quantitative antibody responsiveness is controlled by several independently segregating loci (Stiffel et al., 1987). The first selection experiment using antibody response following immunization was reported in guinea pigs assortatively mated for five generations. The immunogen used was diphtheria anatoxin and the immune responses of progeny were progressively modified in upward and downward directions (Shiebel, 1943). A similar experiment was conducted using rabbits selected for two generations based on antibody produced to Streptococcus sp. (Eichmann et al., 1971). A more extensive examination of antibody response variability in mice was demonstrated by Biozzi et al. (1979). Several independent selective matings were carried out with mice for antibody responsiveness to sheep red blood cells (SRBCs). SRBCs are multideterminant antigens which are strongly immunogenic in all strains of mice (Puel and Mouton, 1996). Assortative mating of mice with extreme phenotypes in upward or downward directions were repeated for successive generations until maximal divergence of the two lines was achieved (Biozzi et al., 1972). The relevance of this dichotomy pertains to the ability of mice to mount strong responses, either antibody or cell mediated immune response, to extra or intra cellular organisms. The low line (L line) was determined to be more resistant than the high line (H line) to intra-cellular organisms such as Salmonellae, Yersinia, Mycobacteria, and Brucellae, and when the macrophage provides the dominant defensive barrier. The H line was more resistant to extracellular microorganism including Pneumococcus, Klebsiella, Plasmodia, and Trypanosoma. The major genetic modification which explained differences between these selected lines was at the level of the macrophage. Antigen was observed to be slowly catabolized and persisted on the macrophage membrane of the H line mice, whereas it was rapidly destroyed in L line macrophages. Selection of chickens based on antibody response to SRBC has also demonstrated variation and the consequent divergence of high and low lines of chickens (Siegel and Gross, 1980; Van der Zijpp et al., 1983; Pinard et al., 1992). Antibody response to SRBC and chicken erythrocytes was similarly evaluated in guinea pigs, which diverged to high and low immune response lines after successive selection for 8 generations (Ibanez et al., 1980). Yorkshire pigs selected using estimated breeding values (EBVs) for both antibody and cell mediated immune response, were reported to diverge into high and low immune response lines (Mallard et al., 1992). The maximum divergence of high and low responses were observed between generation 1($G_1$) and 3 ($G_3$) with little or no response to selection after generation 4 ($G_4$) (Mallard et al., 1997). Although a few studies have examined the effect that selecting for milk production has on various innate and immune response parameters, no breeding studies have been conducted using immune response variation as selection criteria.

Selective breeding of cattle for resistance to mastitis using somatic cell count (SCC) is currently under evaluation. Current industry trends favour a low somatic cell count in milk secretions. A SCC that is too low may be detrimental to innate mechanisms of resistance to mastitis and therefore must be used with caution. Genetic correlation between SCC and mastitis vary, but values are mainly positive (r=0.81; Madsen, 1989; r=0.3, Weller et al., 1996). SCC is now considered the primary trait used to evaluate susceptibility to mastitis which enables indirect selection for resistance to mastitis (Shook, 1994; Dekkers et al., 1998). Selection based on occurrence of clinical mastitis is unreliable since it is not routinely recorded, it has complex aetiology, and observations on the occurrence and severity of mastitis are subjectively evaluated by producers. Several records on SCC are available through dairy herd improvement corporations which provide a substantial database from which to determine estimated breeding values for SCC. SCC and its logarithmic transformation, SCS, have higher heritability ($h^2$=ranging between 0.10–0.12) (Emmanuelson et al., 1988; Banos and Shook, 1990; Boettcher et al., 1992) than clinical mastitis ($h^2$=0.03) (Emmanuelson, 1988; Madsen, 1989). However, low heritability estimates of SCS, in contrast to some production traits, indicate that SCS is not influenced to a greater degree by environmental factors. Low heritabilities suggest that SCS and mastitis will respond more slowly to genetic improvement than milk yield (Shook, 1993; Boettcher et al., 1992). Research conducted in Ontario by Dekkers and Burnside (1994) evaluating estimated transmitting abilities (ETAs) for linear somatic cell score (LSCS) indicated that daughters of the poorest sires had double the average SCC (transformed from LSCS) of daughters of the best sires, and, sires whose daughters had a higher LSCS tend to have more mastitis problems. This research indicated that, although adding LSCS to genetic selection will reduce genetic progress for production by <2 percent, it will also slow down the current genetic deterioration of resistance to mastitis. Its inclusion would be relevant since there would be lower treatment and other related mastitis costs and there would be an increase in the revenue per cow per year by 0.3 to 1.0 percent, despite a slight decrease in milk sales. While there is some benefit to using SCS as a selection tool, it is not as heritable as some aspects of immune response phenotype. Antibody response to ovalbumin (OVA) in dairy calves was reported by Burton et al. (1989) to be moderately heritable ($h^2$=0.48), and in contrast to SCS may be more promising as a selection tool for improved inherent disease resistance (Burton et al., 1989).

Dekkers et al. (1996a) recently developed a sire index called the total economic value index (TEV) which includes economically weighted traits of importance. It includes production, herd life and udder health. Production accounts for 64% of the TEV, herd life for 26% and udder health, which includes SCS, accounts for 10% of the TEV. While production still is the most economically important, more emphasis can now be placed on the costs associated with mastitis by evaluating SCS. Once more heritable candidate markers of immune response are determined, more information about udder health could be added to the TEV.

SUMMARY OF THE INVENTION

The present invention relates to a method of identifying high immune response animals under stress and a method of determining an animal's susceptibility to stress related disease. The method involves evaluating the animal's antibody response to an antigen over a time interval spanning the stress, for example in periparturition, the pre- and postpartum period. Based on the response to the antigen, the animals can be classified as a high, average or low immune responder. Accordingly the present invention provides a method of ranking the immune response of a test animal within a population of animals under stress comprising:

(a) immunizing the animals with at least one antigen at least once before onset of the stress; and (b) for each of the animals within the population, measuring an antibody response to the at least one antigen at least once before the onset of the stress and at least once during the stress, wherein an antibody response from the test animal that is greater than the average antibody response of the population during the stress indicates that the test animal is a high immune responder.

According to another embodiment of the present invention there is provided a method of ranking the immune response of a test animal within a population of animals under stress comprising:

(a) immunizing the animals with at least one antigen at least once before onset of the stress and at least once during the stress; and (b) for each of the animals within the population, measuring an antibody response to the at least one antigen at least once before the onset of the stress and at least once during the stress, wherein an antibody response from the test animal that is greater than the average antibody response of the population during the stress indicates that the test animal is a high immune responder.

Where the stress is periparturition, the high immune responders comprise animals that have a sustained antibody response in both the pre and postpartum period, (herein referred to as Group 1 animals). These animals are least likely to develop peripartum disease. The average (herein referred to as Group 2 animals) and the low (herein referred to as Group 3 animals) immune responders comprise animals that initially have an average antibody response which declines either prior to, or at, parturition. In particular, the average immune responders comprise animals that have an average antibody response up until parturition, and thereafter show a lack of measurable antibody response. The low immune responders comprise animals that have an average antibody response until several weeks prepartum, (e.g., 3 weeks) and show a progressive decline in antibody response thereafter.

Measuring the antibody responses to the antigen over time intervals, rather than at a discreet point in time, allowed the present inventors to develop a mathematical index which can be used to rank the animals. The mathematical index as part of the immunization and measurement schedules of the present invention provide a method of ranking the immune response of a test animal within a population of animals under the stress of periparturition. The method with the index comprise the following:

(a) immunizing the animals with at least one antigen at least once before onset of the stress and at least once during the stress; and (b) for each of the animals within the population, measuring an antibody response to the at least one antigen at least once before the onset of the stress and at least three times during the stress, and at least once after the stress, (c) calculating the mathematical index of the antibody response wherein the mathematical index is: y=primary response+secondary response+tertiary response+quaternary response wherein, (i) y is the total antibody response;

(ii) the primary response is the difference in antibody quantity at a first period of time preperipartum and at a second period of time prepartum, wherein the animal is immunized at the first period of time preperipartum;

(iii) the secondary response is the difference in antibody quantity at the second period of time prepartum and at about parturition, wherein the animal is immunized at the second period of time prepartum;

(iv) the tertiary response is the difference in antibody quantity at about parturition and at a first period of time postpartum, wherein the animal is immunized at about parturition; and (v) the quaternary response is the difference in antibody quantity at the first period of time postpartum and a second period of time post peripartum, wherein animals exhibiting negative secondary or tertiary responses are weighted with a positive coefficient and the test animal having a y value greater than about one standard deviation above the average of the population is a high immune responder.

The inventors have also shown that exposing a population of animals to an antigen which can evoke a cell mediated immune response (CMIR) and measuring at least one indicator of the CMIR of each animal during stress, when combined with the immunization and measurement of antibody schedule of the present invention, there is provided yet another embodiment of the present invention for ranking the immune response of a test animal within a population of animals under stress. According to this embodiment of the invention the method comprises:

(a) immunizing the animals with at least one antigen at least once before onset of the stress;

(b) for each of the animals within the population, measuring antibody response to the at least one antigen at least once before the onset of the stress and at least once during the stress;

(c) exposing the animals to an antigen which can evoke a cell mediated immune response (CMIR); and (d) measuring at least one indicator of the CMIRof each animal during the stress, wherein the measurement of the indicator is combined with the measurement of the antibody response to provide an immune response and a test animal having an immune response greater than the average immune response of the population indicates that the test animal is a high immune responder.

The mathematical index as part of the immunization and measurement schedules of the present invention according to the embodiment just described provides a further embodiment of a method of ranking the immune response of a test animal within a population of animals under the stress of periparturition. The method with the index comprise the following:

(a) immunizing the animals with at least one antigen at least once before onset of the stress;

(b) for each of the animals within the population, measuring antibody response to the at least one antigen at least once before the onset of the stress and at least once during the stress;

(c) exposing the animals to an antigen which can evoke a cell mediated immune response (CMIR);

(d) measuring at least one indicator of the CMIR of each animal of the population during the stress; and (e) calculating the mathematical index of the antibody response and CMIR wherein the mathematical index is: y=primary antibody response+secondary antibody response+tertiary antibody response+quaternary antibody response+CMIR wherein, (i) y is the total antibody response;

(ii) the primary response is the difference in antibody quantity at a first period of time preperipartum and at a second period of time prepartum, wherein the animal is immunized at the first period of time preparipartum;

(iii) the secondary response is the difference in antibody quantity at the second period of time prepartum and at about parturition, wherein the animal is immunized at the second period of time prepartum;

(iv) the tertiary response is the difference in antibody quantity at about parturition and at a first period of time postpartum, wherein the animal is immunized at about parturition;

(v) the quaternary response is the difference in antibody quantity at the first period of time postpartum and a second period of time post peripartum; and (vi) CMIR is the measurement obtained from at least one method of determining CMIR, wherein animals exhibiting negative secondary or tertiary antibody responses are weighted with a positive coefficient and a test animal having a y value greater than about one standard deviation above the average of the population is a high immune responder.

The methods of ranking the animals according to the present invention can be used to identify animals that are least susceptible to developing a postpartum disease. In particular, the present inventors have demonstrated that high immune responder dairy cows have a lower incidence of mastitis as compared to animals that are ranked as average or low immune responders. Accordingly, the present invention provides a use of a method of the invention to identify animals that are selected from the group consisting of: animals that are less susceptible to developing a peripartum disease wherein antibody quantity and quality are relevant host resistance factors; animals that are less susceptible to developing a peripartum disease wherein antibody quantity and quality and CMIR mediate broad-based disease resistance; animals with increased growth hormone; and animals with increased IGF-1 outside the peripartum period and with decreased IGF-1 inside the peripartum period.

Once animals have been ranked by the method of the present invention, the high immune responder animals may be selectively bred in order to produce animals that have lower incidence of peripartum disease.

The methods of the present invention may be used in a wide range of animals including cows, pigs, chickens and other commercially useful animals.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

DETAILED DESCRIPTION OF THE INVENTION

Figure 1:
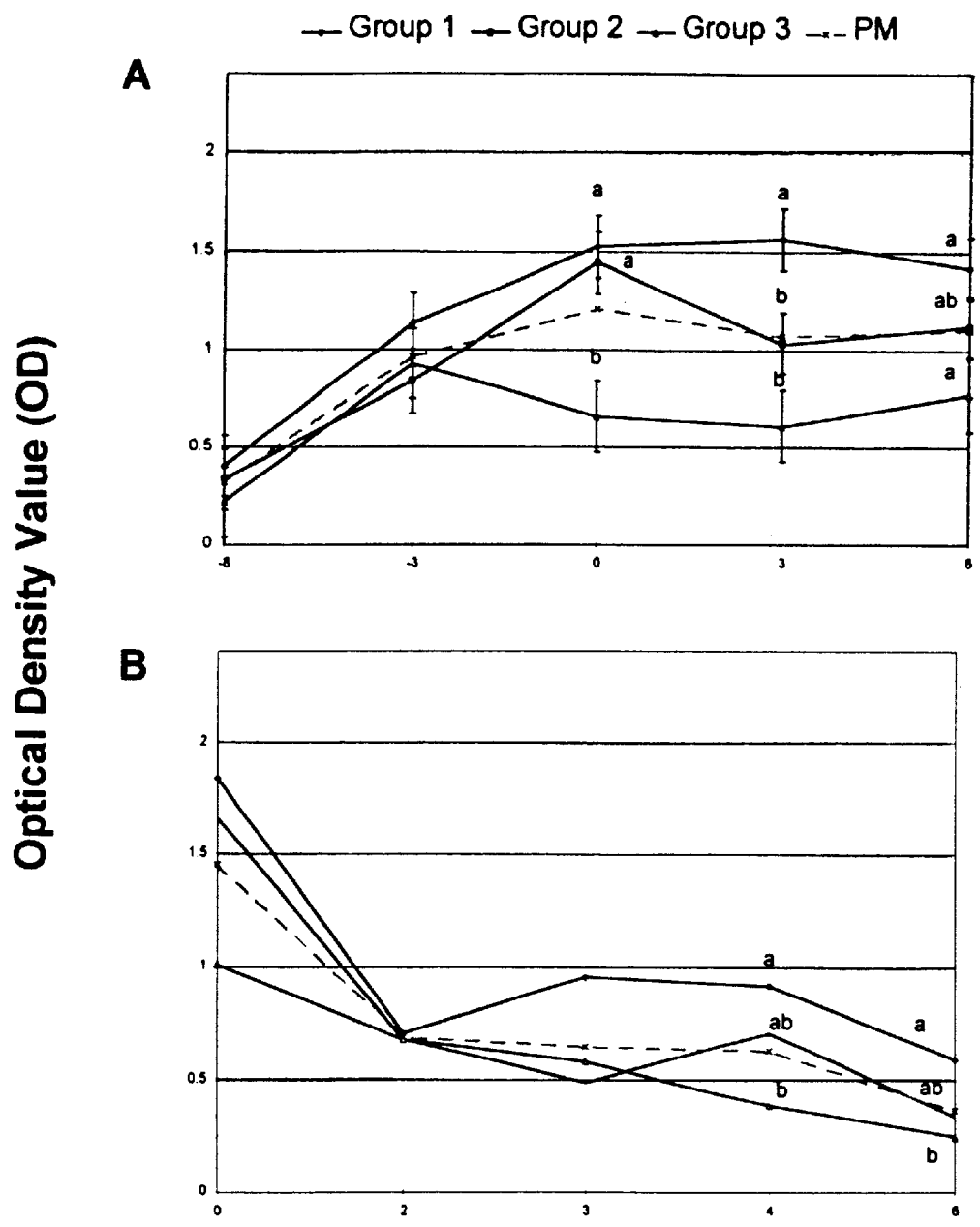
FIGS. 1A and B are graphs showing the anti-OVA antibody levels versus time for animals of Group 1, Group 2 and Group 3.

As hereinbefore mentioned, the present invention is directed to a method of ranking the immune response of an animal within a population of animals. Further the present invention is directed to a method of calculating a mathematical index of the immune response in an animal. The present invention is also directed to the use of the methods of the invention to decrease the incident of disease, to enhance growth hormone (GH) and IGF-1 levels in animals during periods of stress and to breed high immune response animals.

More particularly, the invention is directed to a method of ranking the immune response of a test animal within a population of animals under stress comprising: (a) immunizing the animals with at least one antigen at least once before the onset of the stress; and (b) for each of the animals within the population, measuring antibody response to the at least one antigen at least once during the stress, wherein an antibody response from the test animal that is greater than the average antibody response of the population during the stress indicates that the test animal is a high immune responder.

In a preferred embodiment, each animal is further immunized at least once during the stress. In yet a further embodiment, the antibody response of the animals of the population is also measured at least once before the onset of the stress.

According to another embodiment of the invention, the method of ranking the immune response further comprises exposing the animals of a population to an antigen, preferably under stress, which can evoke a cell mediated immune response (CMIR), measuring an indicator of the CMIR at least once during the stress and combining it with the measurement for antibody response, to obtain an immune response, wherein an immune response of a test animal that is greater than the average immune response of the population during stress indicates that the test animal is a high immune responder. Preferably, the CMIR is specific to the antigen. The antigen used to evoke the CMIR is preferably different than the antigen used to invoke the antibody response.

Suitable indicators of CMIR include, but are not limited to: the measurement of one or more predetermined cytokines [for example, as described in L. T. Jordan et al. "Interferon Induction in SLA-Defined Pigs", Res. Vet. Sci. 58:282–283, 1995; J. Reddy et al., "Construction Of An Internal Control To Quantitate Multiple Porcine Cytokine mRNAs by rtPCR", BioTechniques 21:868–875, 1996; W. C. Brown et al., "Bovine Type 1 And Type 2 Responses", Vet. Immunl. Immunopath 63:45–55, 1998]; measuring delayed-type hypersensitivity (for example as described in Mallard, 1992, PCT/CA93/00533); and measuring in vitro lymphocyte proliferation to at least one antigen (for example, as described in Mallard B. A. et al., Animal Biotech 1992 ref. PCT/CA93/00533).

"Stress" as defined herein, is any acute or chronic increase in physical, metabolic, or production related pressure to the animal. It is the sum of the biological reactions to any adverse stimulus, physical, metabolic, mental or emotional, internal or external, that tends to disturb an organisms homeostasis. Should an animal's compensating reactions be inadequate or inappropriate, stress may lead to various disorders. Many events can place an animal under stress. These include, but are not limited to: weaning, castration, dehorning, branding, social disruption, change in ration, temperature exercise and parturition. Examples of social disruption include, but are not limited to: change of location, shipping, and addition or removal of animals from immediate environment. The onset of parturition (also known as "prepartum"), parturition and after parturition (also known as "postpartum"), herein collectively referred to as "periparturition" or "peripartum", are also known causes of stress in animals. The time of periparturition, the time around parturition, is hereinafter referred to as the "peripartum period". In cows the peripartum period is from about three weeks before to about three weeks after parturition. Therefore, in cows, about 8 weeks prior to parturition would be prior to onset of the periparturition stress; about 3 weeks prior to parturition to about 3 weeks postparturition would be during the periparturition stress; and after about 3 weeks postparturition would be after the peripartum stress.

Although the examples below use cows as the animal model, a person skilled in the art, upon reading this description, would understand that the present invention could be applied to other animals, preferably animals used for commercial use, such as pigs, poultry, fish, horses, and companion animals such as dogs and cats. Accordingly, "animal" as used herein includes, all members of the animal kingdom. In a preferred embodiment of the invention, the animals used are from the bovine genus and more preferably are selected from the group consisting of multiparous and primiparous cows. Further, it is understood that when conducting a method of the invention relatives may be used as the animal to define the rank of other relatives.

One skilled in the art would appreciate that the gestation period differs between animal species. As such, when peripartum is the stress, such a person upon reading this description would know that the optimum times for immunizing and measuring an animal's immune response, as provided in this description for cows, may have to be adjusted, if another animal species is used.

In one embodiment of the invention, pre-peripartum or before the on-set of stress, preferably refers to 2 or more weeks before the onset of stress. For instance, a person skilled in the art would appreciate that the actual time an animal is immunized before the onset of stress will depend on the antigen and animal species used.

According to one embodiment of the invention, when periparturition is the stress and cows are the animals, the animals are immunized at least once before the stress at about 8 weeks before parturition and at least once during the stress at about 3 weeks before parturition and at about parturition.

According to a preferred embodiment of the invention, when periparturition is the stress and cows are the animals, the antibody response is preferably measured at about 8 weeks before parturition, at about 3 weeks before partuition and at about parturition. In a more preferred embodiment the antibody response is further measured at about 3 weeks after parturition. "At about 8 weeks before parturition", as used herein, means at 8 weeks before parturition +/−4 days. "At about 3 weeks before parturition", as used herein, means at 3 weeks before parturition +/−4 days. "At about parturition", as used herein, means at or up to one week after parturition, but not before parturition. "At about 3 weeks after parturition", as used herein means at one week, and preferably at or up to 3 days, after parturition +/−4 days. "Antigen" as used herein, refers to any agent to which an animal is exposed and elicits an immune response. Suitable antigens for use in the present invention can be of bacterial, viral, synthetic, or other origin. For instance in cows, suitable antigens include but are not limited to ovalbumin, hen egg white lysozyme, human seralbumin, red blood cells from any animal other than the cow; tyrosine-glutamine-alaninelysine (SEQ. ID. NO. 1) co-polymer (a synthetic antigen). In choosing suitable antigens for the present invention, the antigens are preferably ones to which the animal is not normally exposed, and preferably one to which they have not been exposed.

The antigens can be formulated into a vaccine, such as *Ecoli* J5, as used in the examples discussed herein. Examples of other possible vaccine antigens for use in cows include but are not limited to: Presponse (Merial) and IBR/PI3/BVD/BRSV combination vaccine (Bovilan 4K) etc.

The term "greater than average antibody response" as used herein means the production of antibody in response to an antigen in an amount that is greater than approximately one standard deviation (sd) above that of the population mean. The preferred source for measuring antibody response in the present invention is milk or blood. "Milk", as used herein, is meant to include both the milk and the colostrum.

The term "greater than average immune response" as used herein means a measure of an indicator of cell mediated immune response combined with the indicator of antibody response, which together provide a value that is one standard deviation above the population mean.

The term "population" as used herein refers to a group of animals of the same species in which the measurements are obtained. For instance, in the examples of the present invention, three different groups or herds are used to obtain the population data. Population as used herein can also refer to a sample of the population, in so far as obtaining the ranking of immune response in a significant sample of a population can enable one to estimate or predict the immune response ranking of other related animals within the population.

According to one embodiment of the present invention, there is a method of ranking the immune response of a test animal within a population of animals under the stress of periparturition comprising: (a) immunizing the animals with at least one antigen at least once before onset of the stress and at least twice during the stress; and (b) for each animal of the population, measuring antibody response to the at least one antigen at least once before the onset of the stress, at least three times during stress and at least once after the stress, calculating the mathematical index of the antibody response wherein the mathematical index is: y=primary response+secondary response+tertiary response+quaternary response wherein, (i) y is the total antibody response;
(ii) the primary response is the difference in antibody quantity at a first period of time before preperipartum and at a second period of time during prepartum, wherein the animal is immunized at the first period of time prepartum;
(iii) the secondary response is the difference in antibody quantity at a second period of time prepartum and at about parturition, wherein the animal is immunized at the second period of time before prepartum;
(iv) the tertiary response is the difference in antibody quantity at about parturition and at a first period of time postpartum, wherein the animal is immunized at about parturition; and
(v) the quaternary response is the difference in antibody quantity at the first period of time postpartum and at a second period of time after post partum, wherein animals exhibiting negative secondary or tertiary responses are weighted with a positive co-efficient, preferably about 1.5. This is done to discriminate against animals with low antibody response during stress. Test animals having a y value greater than about one standard deviation above the average of the population are high immune responders.

The mathematical index of the total immune response can also be obtained with the method of the present invention, wherein the CMIR is added to the above-noted equation and results in y=primary response+secondary response+tertiary response+quartenary response+CMIR, wherein "y" is the total immune response of each animal of a population, and test animals having a "y" value greater than about one standard deviation above the average of the population are high immune responders.

In one embodiment the present invention relates to a modification of the mathematical index in which all phenotypic indicators of immune response are converted to estimated breeding values. The use of this method is as previously described and includes: to identify animals with high immune response; and allow breeding of animals with increased accuracy for inherent increases in immune responsiveness.

The methods of this invention can be used to identify preferred animals selected from the group consisting of: animals that are less susceptible to developing a peripartum disease wherein antibody quantity and quality are relevant host resistance factors; animals that are less susceptible to developing a peripartum disease wherein antibody quantity and quality and CMIR mediate broad-based disease resistance; animals with increased growth hormone; and animals with increased IGF-1 outside the peripartum period and with decreased IGF-1 inside the peripartum period.

The methods of the invention can also be used to obtain a population of animals through traditional hereditary breeding techniques by calculating estimated breeding values (EBVs) of the indicators of immune responsiveness (Veterinary Genetics, F. W. Nicholas, Oxford Science Publications, 1987; D. S. Falconer. An introduction to quantitative genetics. Longman, London, 1981), preferably cows, which are high, average or low immune responders.

The methods of the invention can also be used to predict or estimate the immune response ranking of an animal by having knowledge of the immune response ranking of at least one of the animal's relatives. Factors which would increase the accuracy of the estimate or prediction of such an immune response ranking of an animal, include but are not limited to: (i) Degree of separation from the animal (the knowledge of the ranking of the animal's full siblings and parents would result in a better estimate than with knowledge of the ranking of only cousins or partial siblings); (ii) The amount of data (the greater the database of knowledge of the ranking of one's relatives, the better the estimate or prediction); and (iii) The similarity of environmental factors.

Experimental Design

Identifying variation in immune response traits during the peripartum period, and any association with disease or production traits is the first step toward breeding dairy cows with superior health attributes. To evaluate phenotypic variation in peripartum antibody and cell-mediated immune responses of dairy cows, a total of 136 Holstein dairy animals (88 cows and 49 heifers) from 2 research herds (Herd 1, n=32, 6 heifers and 26 cows; Herd 2, n=67; 34 heifers and 33 cows) and 1 commercial herd (Herd 3, n=37, 8 heifers and 29 cows) were examined weekly from dry-off (approximately eight weeks prepartum; wk-8) to six weeks postpartum (wk 6). To stimulate specific antibody response during the peripartum period, all cows and heifers received intramuscular (im) injections of a mastitis endotoxemia preventive vaccine, an Rc mutant of *Escherichia coli* O111:B4 (Rhône Mérieux *Escherichia coli* J5, Rhône Mérieux, Lenexa, Kans.) with the manufacturer's adjuvant. In addition, cows were simultaneously administered ovalbumin antigen (OVA, Type VII, Sigma Chemical Co., St. Louis, Mo.) approximately 8 weeks (4 mg) and 3 weeks (2 mg) prior to predicted calving dates. At parturition (wk 0), cows received an additional immunization of the OVA dissolved in phosphate buffered saline (PBS–0.1 M, pH 7.4) (2 mg, im). Peripheral blood was sampled via tail venipuncture at weeks −8, −3, 0, 3, 6, and 9 relative to parturition, and centrifuged to monitor serum $IgG_{1\&2}$, as well as specific antibody responses to OVA and J5 *E. coli*. Colostrum and milk samples were also collected to measure specific antibody to OVA and total $IgG_1$ and $IgG_2$ in whey. Colostrum was collected at the first milking following parturition. Milk samples were stripped from all quarters approximately 2–4 hr after morning milking. Colostrum and milk samples were stored frozen without preservative at −20° C. until time of whey separation and Ig quantification.

In order to evaluate delayed type hypersensitivity (DTH) as a measure of cell-mediated immune (CMI) response a subset (n=36) of cows from research Herd 2 (Ponsonby Research Station, Elora, Ontario; n=15 cows and 21 heifers) were given a 1.5 mg/mL intradermal injection of the Bacillus Calmette Guerin (BCG; Connaught, Mississauga, Ontario) vaccine in the left caudal tail fold at wk 1 postpartum. At wk 3 postpartum, animals that had received the BCG vaccine were given a 0.1 mL (250 US Tuberculin Units) intradermal injection of the purified protein derivative (PPD) of *Mycobacterium tuberculosis* and 0.1 mL of the control (PBS), in the right caudal tail fold. These sites were located proximally to one another, about 4 cm apart. Injection sites in the left and right caudal folds were located approximately the same distance from the base of the tail head (10 cm) and across from one another. Double skinfold thickness was measured at 48 and 72 hours using Harpenden Skin Calipers (John Bull, England). As a measure of peripartum lymphocyte proliferation, lymphocytes were harvested from whole blood at weeks −3, 0, 3, and 6 relative to parturition and cultured with OVA antigen (5 μg/mL) and the T-cell mitogen concanavalin A (Con A; 5 μg/mL).

Production Data

Production data were obtained through monthly reports from the Ontario Dairy Herd Improvement Corporation (Ontario DHIC). All monthly milk samples were tested by the Central Milk Testing Laboratory, Guelph, Ontario, for SCC, and compositional content (fat %, protein %). In addition, milk samples from cows in research Herd 1 (Shurgain Research Farm, Burford, Ontario; n=26 cows and 7 heifers) were tested weekly by Ontario DHI. Projected 305 day production parameters for milk, fat, and protein were used as a measure to compare production between cows from the three herds investigated. Three hundred and five day (305-day) projections were calculated based on at least 100 days in milk (DIM). This allows comparisons between cows which may not be at the same stage of lactation when a monthly milk test is taken and between animals with varying lactation lengths.

Disease Data

Occurrence of infectious and metabolic diseases were investigated throughout the study period. All disease events were recorded by the herd manager. If an animal had two or more of the same disease event, it was recorded as one event for the study period.

Specific Antibody Quantification by Enzyme Linked Immunosorbent Assay (ELISA)

Anti-OVA antibody

Serum was separated from coagulated peripheral blood by centrifugation (700×g, 15 min) and stored frozen (−20° C.) until time of assay. Milk samples were centrifuged twice (11000×g, 15 min) to separate fat from whey. Whey was stored frozen at −20° C. Antibody to OVA was detected by ELISA according to the procedure described by Burton, et al., 1993. Dynatech Immulon II flat bottom 96-well polystyrene plates (Fisher Scientific, Don Mills, Ont.) were coated with a $3.11 \times 10^{-5}$ M solution of OVA (OVA, Type VII, Sigma Chemical Co., St. Louis Mo.) dissolved in carbonate-bicarbonate coating buffer (pH 9.6). Plates were incubated (4° C., 48 h), then washed with PBS and 0.05% Tween 20 (Fisher Scientific, Don Mills, Ontario) wash buffer, (pH 7.4) using a EL403 plate washer (Biotek, Mandel Scientific, Guelph, Ontario). Plates were then blocked with a PBS −3% Tween 20 solution and incubated (rt, 1 h). Plates were washed and diluted test sera (1/50 and 1/200) or milk whey (Neat, 1/10, 1/100 and 1/400) and controls were added using the quadrant system described by Wright (1987). After blocking, sera samples were added in duplicate, and milk whey samples were added in quadruplicate. Plates were incubated (rt, 2 h). Subsequently, alkaline phosphatase conjugate rabbit anti-bovine IgG (whole molecule) (Sigma Chemical Co., St. Louis, Mo.) was dissolved in wash buffer, added to the plates and incubated (rt, 2 h). P-Nitrophenyl Phosphate Disodium tablets (pNPP) (Sigma, St. Louis, Mo.) were dissolved in a 10% diethanolamine substrate buffer, (pH 9.8). Plates were washed with wash buffer, pNPP was added to the plates and then incubated (rt, 30 min). Plates were read on a EL311 automatic ELISA plate reader (BIO-TEK Instruments, Highland Park, Vt.) and the optical density (OD) was recorded at 405 and 630 nanometres (nm) when the positive control reached OD≧.999. The 630 filter was used as a reference filter to correct for fingerprints and irregularities in the plastic of the plates. The mean of the number of replicates added to each plate was corrected to an OD=1.0 by multiplying by the inverse of the mean of the positive controls. Corrected means of each dilution were then added together to give an additive OD value, indicative of antibody response.

Negative and positive controls included a pooled sample of pre-immunization sera and a pooled sample of sera from cows 14 days post secondary immunization, respectively. Sera from 20 animals was tested by ELISA to determine antibody responses at 4 dilutions (1/50, 1/200, 1/800, and 1/3200). The dilutions 1/50 and 1/200 provided responses with minimal prozone which corresponded to anticipated antibody response curve kinetics based on the immunization schedule, and allowed a clear differentiation between positive and negative controls. Since for a small subpopulation of cows these dilutions exhibited some prozone effects, the dilutions were added together to provide an index of antibody response. Similarly, in order to determine the optimal sample dilutions that would be used to quantify antibody in milk whey, milk from two cows was serially diluted (neat, 1/2, 1/4 . . . 1/512) to determine the dilution which had a minimal prozone, and allowed optimal differentiation of responses of positive and negative control sera. Acceptable dilutions included Neat, 1/10, 1/100 and 1/400. These dilutions were added together to give and index of whey antibody response.

Anti-*E.coli* antibody

Lyophilized *E.coli* J5 (American Type Culture Collection, Rockville, Md., USA) was grown in 5 mL Tryptic Soy Broth (TSB) for 2 days to obtain log phase growth. This culture was then transferred to a 1 L flask of sterile TSB and sealed aseptically. The culture was incubated (37° C., 12 hrs, 200 rpm) on an INNOVA platform shaker (New Brunswick Scientific, Edison, N.J.). A 1 mL sample of cells was diluted logarithmically and plated on blood agar to determine the colony forming unit count (cfu). The number of cfu was $1.13 \times 10^9$. Live cells were then pelleted by centrifugation (5000 g, 15 min). Cells were washed in PBS and pelleted by centrifugation 3 times (first wash, 5000×g, 15 min; second and third washes, 7500×g, 15 min) Cells were suspended in PBS at a final volume of 1 L. The culture was then heat-killed by boiling for 2 hours. The final preparation was diluted until an absorbance reading=1.0 at 540 nm was obtained. The *E.coli* J5 was stored frozen (−20° C.) until time of assay.

Serum was separated from coagulated peripheral blood by centrifugation (700×g, 15 min) and stored frozen (−20° C.) until time of assay. According to the method described by Rhône-Mérieux Animal Health (Lenexa, Kans.; 1994 personal communication), heat-killed *Escherichia coli* strain J5 (ATCC, Rockville, Md.) was coated at a concentration of $6.25 \times 10^7$ cfu per mL onto Dynatech Immulon II polystyrene 96 well flat bottom plates overnight at 4° C. After washing with wash buffer (PBS plus 0.05% Tween 20), 1% gelatin was added to block non-specific binding and plates were incubated (rt, 1 h). Plates were washed and four replicates of test serum (dilutions of 1/1000, 1/1500, 1/2000 and 1/2500) were added using a modified quadrant system (Wright, 1987). One column with PBS −0.05% Tween 20 was used as a blank, one column of fetal calf serum (FCS, Bockneck Laboratories, Can Sera, Rexdale, Ontario, Canada) was used as a negative control and one column each of the negative and positive controls prepared from pooled pre- and post immunization sera were plated, respectively. Test sera were incubated (rt, 2 h), and then the plates were washed with PBS −0.05% Tween 20. Horseradish peroxidase conjugate goat anti-bovine IgG whole molecule in PBS (1/4000) (The Binding Site, Birmingham, England) was added and the plates were incubated (rt, 1 h). After subsequent washing with PBS −0.05% Tween 20, the substrate, 2,2'-azino-di-(4-ethyl-benzthiazoline sulphonate-6) (ABTS) was added and plates were incubated (rt, 30 min). Plates were then read on an EL311 automatic ELISA plate reader (BIO-TEK Instruments, Highland Park, Vt.) and the OD was recorded at 405 nm and 490 nm. The mean OD of the four sample replicates were corrected for each plate by multiplying by the inverse of the mean of the positive controls and used as an indicator of antibody response. Based on the immunization protocol and phenotypic observation of antibody response curve kinetics of all dilutions tested, the 1/1000 dilution consistently allowed for differentiation between positive and negative controls, exhibiting minimal prozone effect. Therefore 1/1000 was the dilution of choice for comparison between animals.

The same pooled positive sera used in the OVA ELISA was tested to ensure a differentiation between pre-immune negative sera and post secondary immunization sera. This positive control was determined to be suitable for this assay since an OD of 1.0 was reached at a dilution of 1/200 while the negative sera had an OD that was <0.100. Negative control sera in this assay was prepared by absorbing boiled whole cell *E.coli* J5 in pooled non-vaccinated sera. FCS was also used as a negative control.

Quantification of Immunoglobulin $G_{1\&2}$ by Radial Immunodiffusion (RID)

Quantification of Total $IgG_{1\&2}$ in sera

Radial immunodiffusion (RID) was used according to a modified method described by Mallard et al, 1992, to determine the concentrations of $IgG_{1\&2}$ in serum at weeks 0, 3, and 6 relative to parturition. Immunodiffusion medium was prepared by dissolving 2% Seakem agarose (FMC Bioproducts, Mandel Scientific, Guelph, Canada) and 2% Polyethylene Glycol 8000 (Carbowax 8000, Fisher Scientific, Fairlawn, N.J.) in PBS. Rabbit anti-bovine isotype specific $IgG_{1\&2}$ (VMRD, Pullman, Wash.) was suspended in the immunodiffusion agarose at a concentration of 33% (vol/vol) for $IgG_1$ and 30% (vol/vol) for $IgG_2$. Immunodiffusion medium was held in a liquid state and poured into 5 mL immunodiffusion plates. Agarose was allowed to solidify and then three rows of wells, 6 wells per row, were punched with a 3 mm glass pipette tip. Standard concentrations of $IgG_1$ (1800 mg/100 mL) and $IgG_2$ (1600 mg/100 mL) as controls (VMRD, Pullman, Wash.) were diluted (neat, 1/2, 1/4, 1/8, 1/16, 1/32) and five microlitres of these standard serial dilutions were added to the top row of each plate. Five µL of each test sample was added to the two bottom rows of each plate. Plates were incubated (rt, 20 h) in a humidified chamber. Afterwards, ring diameters were measured using a calibrated grid held over a fluorescent light source. Ring diameters from standards were used to make a standard curve for each plate determined by linear regression. By plotting ring diameter on the x axis and the log of the concentration (mg/100 mL) on the y axis, the concentration of Ig could be determined.

Quantification of Total $IgG_{1\&2}$ in whey

In order to determine Ig concentration in colostrum, immunodiffusion medium was prepared by dissolving 2% Seakem agarose (FMC Bioproducts, Mandel Scientific, Guelph, Canada) and 2% Polyethylene Glycol 4000 (Carbowax 3350, Fisher Scientific, Fairlawn, N.J.) in PBS. Rabbit anti-bovine isotype specific $IgG_{1\&2}$ (VMRD, Pullman, Wash.) was suspended in the immunodiffusion agarose at a concentration of 33% (vol/vol) for $IgG_1$ and 30% (vol/vol) for $IgG_2$. The procedure for the preparation of RID medium and plates for colostral whey samples was essentially the same as that described for sera except that polyethylene glycol 3350 was used instead of 8000 to improve ring clarity. Colostrum samples were centrifuged twice (11000×g, 15 min) to separate fat from whey prior to plate application.

In order to determine Ig concentration in milk, immunodiffusion medium was prepared by dissolving 2% Seakem agarose and 2% Polyethylene Glycol 4000 (Carbowax 3350, Fisher Scientific, Fairlawn, N.J.) in PBS. Rabbit anti-bovine isotype specific $IgG_1$ (VMRD, Pullman, Wash.) was suspended in the immunodiffusion agarose at a concentration of 12.5% (vol/vol). Milk samples were centrifuged twice (11000×g, 15 min) to separate fat from whey. The procedure for the preparation of RID medium and plates for milk whey samples is essentially the same as that described for colostrum except that the concentration of goat-antibovine sera suspended in the immunodiffusion media was 33% for IgG1 and 30 % for IgG2. Whey from wk 3 was tested for both $IgG_{1\&2}$ subclasses. At wk 6 however, $IgG_1$ only was tested in whey since very low concentrations of $IgG_2$ exist in normal milk.

Examination of the Cell-Mediated Immune Response (CMIR) Delayed Type Hypersensitivity A preliminary study was conducted to determine if the Ponsonby herd was previously exposed to *Mycobacterium tuberculosis* or other cross reactive antigens from *Mycobacterium paratuberculosis*. Five cows and six heifers were injected intradermally with 0.1 cc of the PPD of *M. tuberculosis* (Connaught, Mississauga) and a control dose of 0.1 cc PBS (pH 7.4) in the right caudal tail fold located proximally to one another (approx. 4 cm apart) PPD was injected in a designated area above the PBS site. Both injection sites were 10 cm from the base of the tail head. Prior to injection, injection sites were encircled with a coloured marker and a pre-test and pre-control thickness measurement was taken in triplicate, using Harpenden skin calipers (John Bull, England). This measurement was identified as the time=zero hours measurement. After 24 and 48 hours, skin thickness measurements were taken to assess the percent increase in skin thickness of control and test sites. It was determined that the herd had not previously been exposed to the *M. tuberculosis* antigen since 95% of all the animals tested had very little or no increase in skin thickness at the injection sites (i.e a 0–7% increase in skin thickness) and that the BCG/PPD test system would be suitable to measure DTH responses in this herd.

Two animals from the Ponsonby herd were selected to determine the optimal time point following the injection of PPD that would yield a maximal response and ensure that actual DTH responses were induced. Animals were evaluated at 0, 6, 12, 24, 48 and 72 hours post PPD challenge. Measurements taken at 6 to 12 hours were used to ensure that the response to antigen was not characteristic of an antibody-mediated reaction. In cattle, the maximal response to PPD is normally observed around 72 hours (Radostits et al, 1990). Preliminary results indicated that the response was optimal at 48 hours, therefore both time points were evaluated for comparison between animals.

Prior to immunization using PPD, and a PBS control, a pre-test and pre-control (at time=0 hours) skin thickness measurement was obtained in triplicate from each of the 36 animals evaluated. Forty eight and 72 hours after secondary challenge, these measurements were taken again. The amount of skin thickness increase at 48 and 72 hours expressed as a percent increase in skin thickness was calculated as follows:

$$\% \text{ increase in skin thickness} = (((A-B)/B)-(C-D)/D)))\times100$$

where A=mean test thickness (at time=48, 72 hours),
B=mean of pre-test thickness (at time=0 hours),
C=mean of control thickness (at time=48, 72 hours),
D=mean of pre-control thickness (at time=0 hours).

Cows could be classified according to their % increase in skin thickness as either non-responsive or low responders (less than one sd below the mean), moderate responders (between one sd below and one sd above the mean), or high responders (more than one sd above the mean).

Lymphocyte Proliferative Response

Lymphocyte proliferation assays were performed according to the procedure of Chang, et al. (1993). Peripheral whole blood was centrifuged (850×g, 15 min) and buffy coats were diluted in phosphate buffered saline (PBS 0.1 M, pH 7.4). Peripheral blood lymphocytes (PBL) were separated by density gradient centrifugation (1000×g, 30 min) of buffy coats using aqueous Histopaque 1.077 (Sigma Chemical Co. St. Louis, Mo.) Cell pellets were washed by centrifugation in PBS (400×g, 7 min) and suspended in a volume of culture medium (Rosewell Park Memorial Institute; RPMI-1640, and 100 I.U. penicillin-streptomycin, prepared by Central Media Laboratory; Ontario Veterinary College, University of Guelph, Guelph, Ontario.) and 10% FCS and brought to a final concentration of $2.0\times10^6$ cells/mL in culture medium. In order to determine specific clonal proliferative responses to antigen, a stock solution (50 μg/mL) of OVA (Sigma Chemical Co., St. Louis Mo.) dissolved in RPMI-1640 was prepared and stored in small aliquots at −70° C. Five μg/mL of OVA was added to 6 replicates of test lymphocytes in 96 well flat-bottom plates (Nunc, Fisher Scientific, Don Mills, Ontario). Medium was added to 6 well replicates of cells as non-stimulated controls and this represented background or unstimulated cell proliferation. As a general indicator of lymphocyte proliferation, Con A mitogen similarly prepared from stock solution (50 μg/mL) and diluted (5 μg/mL) was added to 6 replicates of cells on a separate plate containing an additional 6 wells as medium controls. Following 24 h of incubation with OVA or Con A(37° C., 6% $CO_2$) cells received an 18 h 'pulse' incubation with 0.5 μCi methyl tritiated thymidine per well (ICN Biochemical, Canada Ltd. Montreal, PQ). Plates were frozen until cells were harvested using a plate harvesting system (LKB Wallac, Turku, Finland) onto fiberglass filter mats (LKB Wallac, Turku, Finland). Radioactivity was recorded as counts per minute (cpm) of test minus non-stimulated controls of retained radioactivity measured by a beta plate liquid scintillation counter (LKB Wallac,Turku, Finland).

OVA antigen preparations were tested using the above described method at a concentration of 5 μg/mL, 10 μg/mL, and 20 μg/mL. Although lymphocyte proliferative responses did not differ significantly between the tested concentrations, 5 μg/mL was selected to induce PBL proliferation in subsequent assays. To determine the concentration of the mitogen able to induce optimal PBL proliferation, Con A concentrations were tested at 2 μg/mL, 5 μg/mL and 10 μg/mL. Five μg/mL yielded maximal lymphocyte proliferative responses and was therefore selected as the concentration applied in further investigations.

Flow Cytometric Assay for the detection of CD Surface Molecules on Lymphocytes either not stimulated or stimulated with Con A or OVA In order to determine which lymphocyte subsets were present after stimulation with either Con A or OVA, cells were stained with monoclonal antibodies recognizing 5 cell surface markers according to the method described by Van Kampen and Mallard (1997). The monoclonal antibodies used in this study were kindly provided by Dr. Jan Naessens of ILRAD (Institute for Animal Health, Compton, Berkshire) and included antibodies to the following cell surface markers: CD2+(IL-A43), CD4+(IL-A11), CD8+(IL-A105), WCI (IL-A29), and IgM (IL-A30). A subset of animals (n=10) from research Herd 2 (Ponsonby, Elora, Ontario; n=7) and the commercial herd (Speedvalley Holsteins, Fergus, Ontario; n=3) were evaluated for expression of these lymphocyte cell surface markers at weeks −3, 0, 3, and 6 relative to parturition. Lymphocytes were prepared and cultured as previously described for lymphocyte proliferation assays, however, each 96 well plate was divided into quadrants each with 24 wells. Twenty four replicates each of Con A stimulated, OVA stimulated (at 5 μg/mL and 20 μg/mL) and non-stimulated controls were cultured for 42 hours (the same total duration used in the lymphocyte proliferation assays). After 42 hours, cells were harvested by pipette, washed with PBS and transferred to 10 mL glass test tubes. Cells were centrifuged (400×g, 10 min), and supernatants were poured off and cells were resuspended in 250 μL PBS+0.1M Azide. Immunostaining was performed in 96-well round-bottom plates (Coming, New York, N.Y.). Fifty μL of cells and 50 μL of diluted primary antibody were added to each well and incubated (20 min, rt). After incubation, 100 μL of PBS+0.1M sodium azide (Fisher Scientific, Fairlawn, N.J.) was added to each well to wash the cells. Cells were suspended by mixing on a shaker and centrifuged (400×g, 6 min). Supernatants were then removed using an aspirator. This washing procedure was performed twice. Fifty μL of FITC-conjugated goat anti-mouse IgG(H+L) (Cedarlane Laboratories, Hornby, Ontario) was then added to the cells and cells were incubated (rt, 20 min). After incubation, plates were washed twice as described above. Cells were fixed in 1% paraformaldehyde and transferred into 3 mL polystyrene tubes (Becton Dickinson, Lincoln Park, N.J.) containing 300 μL of 1% paraformaldehyde. Tubes were covered with parafilm and refrigerated until time of assay.

A FACS Scan flow cytometer (Becton Dickinson, Lincoln Park, N.J.) was used to acquire all lymphocyte subset data. LYSIS II software (Becton Dickinson, Lincoln Park, N.J.) was used for fluorescence data analyses. Lymphocytes were gated from other populations based on their forward and side scatter characteristics. Five FITC histograms were plotted for each cow, time point and culture condition observed. Histograms representing fluorescence of cells expressing CD2 (pan T cell), CD4 (helper T cells), CD8 (cytotoxic/ suppressor T cells), WCI (gd T cells), and IgM (B cells) cell surface markers were examined. The region of background fluorescence was established with the negative control marker, M1. Everything to the right of this marker was considered positive.

Complete Blood Cell Counts

Complete Differential Blood Cell Counts were determined by the Clinical Pathology Laboratory at the Ontario Veterinary College, University of Guelph, Guelph, Ontario, Canada. Counts included the percent and number erythrocytes, banded neutrophils, segmented neutrophils, lymphocytes, monocytes, basophils, eosinophils, as well as total leukocytes.

Somatic Cell Counts in Milk

Weekly somatic cell counts (SCC) of the Shurgain herd were obtained using the weekly sampling service offered by Ontario DHI. Weekly samples of cows in the Ponsonby and Dunk herds sampled 1–4 hours after morning milking were tested for SCC by the Mastitis Laboratory at the Ontario Veterinary College, University of Guelph, Guelph, Ontario Canada. Monthly somatic cell counts were obtained from Ontario DHI records for all three herds.

Categorization of Cows Based on Antibody Response Biological Classification Using Antibody Response Curves Serum antibody responses to OVA from the first herd investigated (Shurgain, Burford, Ontario, n=32) were graphed individually for each cow at weeks –8, –3, 0, 3, and 6 to examine response curve patterns. Evaluation of these curves during the peripartum period through to peak lactation indicated that enough variation existed to rank animals according to antibody response to OVA. Cows that showed consistently above average responses to OVA were categorized as high or Group 1. Cows that had an average antibody response up until parturition and thereafter showed a lack of measurable (LOM) antibody response were categorized as the postpartum LOM response group or Group 2. Cows that had an average antibody response until three weeks prepartum and showed a progressive decline in measurable antibody response were categorized as the peripartum LOM group or Group 3.

Subsequent investigations of immune responses between cows in the other herds studied revealed similarities. However, subtle differences in the amplitude and direction of antibody response curves, in relation to the immunization schedule, indicated that the data was continuous in nature. Thus, the groups determined for Herd 1 wouldn't necessarily apply to all herds. It was clear then, that antibody responses to OVA were on a continuum, and any classification method implemented would benefit from a quantitative approach to readily and appropriately partition phenotypic variation between cows.

Quantitative Classification Using a Mathematical Index

Serum antibody responses to OVA were evaluated over time intervals, rather than discrete points in time. Individual animal antibody response curves from week –8 to week 6 relative to parturition (week 0) were dissected into components reflecting the response to antigen following immunizations. Primary response was defined as the change in antibody to OVA from week –8 to week –3 relative to parturition following primary immunization at week –8 (Primary=OD value at week –3 minus OD value at week –8). Secondary response was defined as the change in antibody to OVA from week –3 to parturition following secondary immunization at week –3 (Secondary=OD value at week 0 minus OD value at week –3). Tertiary response was defined as the change in antibody to OVA from parturition to week 3 following tertiary immunization at parturition (Tertiary=OD at week 3 minus OD at week 0). Quaternary response was defined as change in antibody to OVA from week 3 to week 6 (Quaternary=OD value at week 6 minus OD value at week 3). Quaternary response was included to observe the change in antibody response between the end of the immediate postpartum period (wk 3) and peak lactation. These responses were added together to give an index of antibody response to OVA between wk –8 and wk +6 relative to parturition as follows:

$y_{index}$=primary+secondary+tertiary+quaternary where, y=total antibody response;

primary, secondary, tertiary, and quaternary responses are as previously defined;

primary, secondary, tertiary, and quaternary responses when positive, have an equal weight of 1.

Animals which exhibited negative secondary or tertiary responses during the immediate pre-and post-partum period were weighted with a coefficient of 1.5 instead of 1. Only secondary and tertiary responses were weighted in this manner, since this is the period when lowered host resistance mechanisms are thought to contribute to increased occurrence of disease. The coefficients for weighting negative secondary and tertiary responses were optimized using the original biological assessment for grouping animals in the first herd investigated. The quantitative ranking of animals had to reflect the biological assessment of grouping animals based on the magnitude and direction of response to immunization.

The mean of the antibody response index was determined and animals that exceeded one standard deviation above the mean were classified as high responders (Group 1). Animals that were one standard deviation below the mean were classified as low responders (Group 3). Animals with an index of antibody response that ranged between one standard deviation below and above the mean were classified as average responders (Group 2).

Statistical Methods

Least squares analysis of variance (ANOVA) and corrected means (least square means, LS Means) were generated using the General Linear Models (GLM) Procedure of the Statistical Analysis System (Helwig and Council, 1982). A model was constructed for the following dependent variables: antibody response to OVA in sera and whey, antibody response to E.coli in sera, concentration of $IgG_{1\&2}$ in serum and whey, background lymphocyte proliferation and lymphocyte proliferation following culture with Con A or OVA, DTH, SCS and production variables. Sources of variation included in the model for each dependent variable are summarized in Table 1. Data that did not show a normal distribution, as indicated by the univariate procedure of SAS (Helwig and Council, 1982), were transformed to natural logarithms. The Proc CORR procedure of SAS was used to generate Pearson product moment correlation coefficients between immune response parameters and production variables. Results were considered to be statistically significant if the p-value was $\leq 0.05$ and trends were reported at a p-value $\leq 0.10$.

Models indicated are base models. Some parameters were excluded if non-significant in order to generate LS Means.

Model 1

Antibody response to OVA in serum and whey, Ig in serum and whey and E. coli in serum $y_{ijklmn}=\mu+herd_i+season-yr_j+cow(group*parity)_{klm}+week_n+group_k+parity_l+(group*parity)_{kl}+(group*week)_{kn}+e_{ijklmno}$ where,
- $y_{ijklmno}$=observed response of cow m in group k and parity l for each sample week of each cow,
- $\mu$=the population mean,
- $herd_i$=fixed effect of herd (i=1,2,3),
- season-$yr_j$=fixed season-year effect (j=Spring 1994, Summer 1994, Fall 1994, Winter 1994/1995, Spring 1995, Summer 1995, Fall 1995, Winter 1995/96),
- $group_k$=fixed effect of group based on antibody response to OVA (k=1,2,3),
- $parity_l$=fixed effect of parity (l=1,2, or >3),
- $(group*parity)_{kl}$=fixed effect of group*parity interaction,
- $cow(group*parity)_{klm}$=random effect of cow-grouped within group*parity term,
- $week_n$=fixed effect of sample week (n=−8,−3, 0, 3, 6, 9),
- $(group*week)_{kn}$=fixed effect of group by week interaction term;
- $e_{ijklmno}$=random or residual error term.

When parity was not significant, the cow term was edited to reflect the appropriate nested variable.

Model 2
Cell Mediated Immune Responses and Lymphocyte proliferation $y_{ijklmnop}=\mu+herd_i+season-yr_j+cow(group*parity)_{klm}+week_n+group_k+parity_l+(group*parity)_{kl}+(group*week)_{kn}+replicate_o+b(cov)_{ijklmno}+e_{ijklmnop}$ where all variables are as described for model 1 except,
- $y_{ijklmnop}$=observed response of cow m in group k and parity l for each replicate o at each sample week,
- $replicate_o$=fixed effect of replicate (o=1,2,3,4,5,6), and
- $b(cov)_{ijklmno}$=regression coefficient of $y_{ijklmnop}$ on resting cell proliferation for the $klm^{th}$ cow The model for DTH was:

$y_{ij}=\mu+group_i+e_{ij}$;

where,
- $\mu$=the population mean,
- $group_i$=fixed effect of group based on antibody response to OVA (i=1,2,3),
- $e_{ij}$=random or residual error term.

Parity was not included in this model since it was not significant, and when included with group, did not provide enough degrees of freedom to run the analysis of variance.

Tests of hypothesis of group or parity were tested against the MS random error term for cow. Type III Sums of Squares corrected for all other variable within the model were used account for the variation in immune responses.

The following non-limiting examples are illustrative of the present invention:

EXAMPLES

Example 1
Periparturient Antibody Response Profiles of Holstein Cows: An Initial Immunobiological Assessment To evaluate phenotypic variation in peripartum immune responsiveness of dairy cattle, 33 Holstein cows were immunized with ovalbumin (OVA) and *Escherichia coli* J5 at weeks −8 and −3 prior to parturition. At parturition (week 0), cows received an additional immunization of OVA. Blood was collected at weeks −8, −3, 0, 3 and 6 relative to parturition to measure serum immunoglobulin (Ig) concentration, and antibody to OVA and *E.coli*. Colostrum and milk were also collected post-parturition to measure Ig and antibody to OVA. All cows had a measurable antibody to OVA following primary immunization, but not all cows responded to second and/or third immunizations. Antibody response to OVA was used to classify cows into three groups recognizing animals with sustained measurable antibody response before and after parturition (Group 1), animals which responded poorly or did not respond to immunization at parturition (Group 2), and animals which did not respond to immunizations at week −3 or at parturition (Group 3).

The objectives of this example were threefold: 1) to investigate antibody response during the peripartum period; 2) to classify cows based on variation of antibody response; and, 3) determine if antibody response is associated with the occurrence of disease.

Materials and Methods

Animals and Treatments

Antibody response of 33 Holstein cows were examined from approximately eight weeks prepartum (week −8), based on predicted calving dates to six weeks postpartum (week 6). Twenty-six animals were multiparous cows and seven were primiparous heifers. Cows received an intramuscular (im) injection of a mastitis endotoxemia preventive vaccine with the manufacturer's adjuvant (Rhône Mérieux *E. coli* J5, Rhône Meérieux, Lenexa, Kans.) along with the antigen OVA (Type VII, Sigma Chemical Co., St. Louis, Mo.), at weeks −8 (4 mg OVA) and −3 (2 mg OVA). At parturition (week 0), cows received an additional immunization of OVA without adjuvant dissolved in phosphate buffered saline (PBS–0.1 M, pH 7.4) (2 mg, im). Ovalbumin was chosen as an inert soluble antigen to which these animals had likely not been previously exposed. *E. coli* J5 was used as a complex, insoluble, biologically relevant antigen to which most dairy cows were likely to have been previously exposed. Antibody response to OVA was used to classify cows into three groups recognizing animals with sustained measurable antibody response before and after parturition (Group 1), animals which responded poorly or did not respond to immunization at parturition (Group 2), and animals which did not respond to immunizations at week −3 or at parturition (Group 3)(FIG. 1A).

Blood and Milk Sampling Schedule

Blood was collected by tail venipuncture at week −8, and weekly from weeks −3 to 6 relative to parturition. Serum was used to monitor immunoglobulin $G_{1\&2}$ concentrations, and determine antibody to OVA and *E. coli* J5. Colostrum and milk were collected to determine antibody to OVA and to monitor $IgG_1$ (weeks 0, 3, 6) and $IgG_2$ (weeks 0 and 3) concentration. Colostrum was collected at the first milking following parturition. Milk was obtained from all quarters approximately 2–4 hr after morning milking. Colostrum and milk samples were frozen without preservative at −20° C. until the time of whey separation and analysis.

Anti-OVA Enzyme Linked Immunosorbent assay (ELISA) As described in the General Methods section.

Anti-*E. coli* J5 ELISA As described in the General Methods section.

Radial Immunodiffusion Assay As described in the General Methods section.

Disease Occurrence As described in the General Methods section.

Milk Somatic Cell Count

Milk (AM/PM composite sample) was collected weekly by the herd milker during milking to determine somatic cell count (SCC). Only SCC which coincided with the day of blood sample collection for each week are reported. SCC, an indicator of subclinical mastitis, was transformed to somatic cell score (SCS) for analysis. SCS is the natural logarithm of SCC in cells/$\mu$L and is calculated as follows (Shook, 1993):

$SCS = \log_e(SCC/100) \div \log_e(2) + 3$

Statistical Methods

Type III least squares analysis of variance (ANOVA) and corrected means (least square means, LS Means) were generated using the General Linear Models (GLM) Procedure of the Statistical Analysis System (SAS; Helwig and Council, 1982). The statistical models used included fixed effects of antibody response groups (1,2,3), cow nested within antibody response group, and week relative to parturition (weeks −8, −3, 0, 3, and 6). In preliminary analysis, the effect of parity was not significant and was therefore removed from all subsequent models. A model was constructed for the following dependent variables: antibody response to OVA in sera and whey, antibody response to $E.$ $coli$ J5 in sera, and the concentration of $IgG_{1\&2}$ in serum and whey. Sources of variation included in the model for each dependent variable are summarized in Table 1. Data that were not normally distributed as indicated by the univariate procedure of SAS, were transformed to natural logarithms. (whey antibody to OVA, serum antibody to $E.$ $coli$, serum and whey $IgG_2$. Pearson product moment correlation coefficients between immune response variables were generated using the correlations procedure of SAS (Proc CORR). Results were considered to be statistically significant if the P-value was $\leq 0.05$ and trends were reported at P-values $\leq 0.10$.

Results

Antibody Response to OVA

Antibody in serum

Serum antibody to OVA varied significantly over the peripartum period and individuals could readily be classified into three immune response groups: high responders (Group 1, n=12; 6 heifers, 6 cows) versus animals which exhibited a LOM response to immunization either postpartum (Group 2, n=12 cows) or pre- and postpartum (Group 3, n=9; 8 cows, 1 heifer). Approximately ⅓ (Group 1) of the animals had consistently above average serum antibody response to OVA following immunization at weeks −8, −3, and 0 relative to parturition. The remaining animals had OD values measuring antibody to OVA that were close to the population mean or had responses lower than the population mean and did not respond following immunization at week −3 or parturition (FIG. 1A). All cows, including those of Group 3, had serum antibody greater than background (week −8) at week −3 and therefore were considered low responders rather than non-responders. The statistical model (ANOVA) accounted for 94.19% of the total variation in serum antibody to OVA over the peripartum period. Effects of cow ($P \leq 0.0001$), antibody response group ($P \leq 0.0001$), week ($P \leq 0.0001$), and the interaction between antibody response group and week ($P \leq 0.0001$), contributed significantly to the variation in serum antibody to OVA (Table 1).

Antibody in Whey

Cow ($P \leq 0.0001$), week ($P \leq 0.0001$), and antibody response group ($P \leq 0.0001$) contributed significantly to the variation in antibody in whey (Table 1). There was also a tendency for the interaction between antibody response group and week ($P \leq 0.09$) to account for variation in whey antibody to OVA. Population LS Means of whey antibody to OVA declined significantly following parturition, such that at week 0 the OD value was 1.456 compared to 0.645 ($P \leq 0.004$) at week 3 and 0.366±0.20 ($P \leq 0.0001$) at week 6 (FIG. 1B). At weeks 3 and 6, Group 1 cows were significantly higher than ($P \leq 0.05$) Group 3 cows.

Antibody Response to $E.$ $coli$ L5

Cow ($P \leq 0.0001$), week ($P \leq 0.0001$), and antibody response group (0.0001) all contributed significantly to variation in antibody response to $E.$ $coli$ J5. OD values of pre-immunization sera (week −8) indicated that these cows had minimal measurable $E.$ $coli$ J5 antibody (population mean of OD=0.296; n=33) compared to post-vaccination antibody at week −3 (0.739) and week 0 (0.789). Antibody response to $E.$ $coli$ J5 was positively correlated with antibody response to OVA ($r^2=0.59$, $P \leq 0.0001$).

$IgG_1$ & $IgG_2$ in serum, colostrum, and milk

Antibody response group significantly contributed to the variation of serum $IgG_2$ ($P \leq 0.0001$) only. Group 3 cows had a significantly ($P \leq 0.05$) higher serum $IgG_2$ concentration than Groups 1 and 2 at parturition. Antibody to OVA was negatively and significantly correlated with serum $IgG_2$ ($r=-0.23$; $P \leq 0.05$).

Disease Occurrence

Fifty four and a half % of the 33 animals evaluated were considered healthy during this study. Of the diseased animals, seven cows had mastitis (21.21%), seven had ketosis (21.21%) and three cows had other diseases (9.09%). Animals in Group 1 that had above average antibody to OVA, had the lowest percent occurrence of disease (17%) (FIG. 2) and actually had no clinical mastitis.

3.5. Somatic Cell Score (SCS)

At parturition, LS Means of SCS were significantly lower ($P \leq 0.05$) for Group 2 cows (SCS=3.2) compared to Group 1 (SCS=4.36) and Group 3 (SCS=4.98) cows. At weeks 2,3,4, and 6 after parturition, all groups differed significantly from one another, and, Group 1 cows consistently had the lowest SCS while Group 3 cows consistently had the highest SCS.

Discussion

Antibody response before and after parturition has not been thoroughly investigated. Antibody response to OVA, a test antigen to which these animals would normally not have and had probably not been previously exposed, was utilized to partition cows into three immune response groups recognizing animals with sustained antibody response before and after parturition (Group 1), animals which did not respond to immunization at parturition (Group 2), and animals responding poorly throughout the peripartum period (Group 3). Variation in antibody response to $E.$ $coli$ J5, a biologically relevant antigen, was more difficult to partition. Pre-immunization $E.$ $coli$ antibody was significantly lower compared to post immunization antibody in this herd. This indicates that the $E.$ $coli$ J5 antigen would be useful for classifying animals in the herd evaluated according to their antibody response but does not indicate that another herd will respond in the same way. Pre-immunization antibody may be higher in other herds where gram negative bacteria are frequently encountered.

Nagahata et al. (1992), examined B lymphocyte populations in order to evaluate host defense in dairy cows during the periparturient period. This study found no significant changes in the number of B lymphocytes of cows from two weeks before until two weeks after parturition. However, they did report a significant decrease in antibody producing cells immediately after parturition. The authors suggested this indicated a decrease in B lymphocyte function during the immediate postpartum period. This is consistent with the low peripartum antibody response seen in some animals in the present study.

Although it has been reported that serum antibodies decline at parturition and colostral antibodies increase due to the sequestration of immunoglobulins into the mammary gland (Detilleux et al., 1995), this study suggests that lower antibody in serum does not necessarily relate to Ig transport. For instance, Group 1 cows, which had the highest serum antibody responses, also tended to have higher whey antibodies to OVA postpartum, when compared to cows of Groups 2 and 3. Initially, it was questioned whether low serum antibody may be associated with higher antibody in the colostrum or milk. This data indicates that animals with high serum antibody also supply high concentrations of antibody to the mammary gland.

This example has demonstrated significant individual variation during the peripartum period and confirms that not all cows have depressed antibody response. In swine, animals with inherently high and low immune response phenotypes can also be identified in a population (Mallard et al., 1992). In light of previously reported heritability ($h^2$) estimates of bovine antibody response (Burton et al., 1989), these data from this study may suggest that Group 1 animals could be inherently better able to produce antibody, in spite of the metabolic and physical stresses of the peripartum period. Cows in Group 1 did have the lowest occurrence of peripartum disease, particularly mastitis (0% occurrence), and significantly lower SCS scores following parturition than cows in Groups 2 and 3, thus indicating that antibody response should be considered as a potential marker of peripartum disease resistance.

Example 2
A Quantitative Approach to Classifying Holstein Dairy Cows Based on Antibody Response, the Relationship Between Antibody Response and Peripartum Disease Occurrence, and Heridability Estimates A quantitative approach was developed to partition phenotypic variation of peripartum antibody response profiles of Holstein cows and to determine associations with peripartum mastitis. Using a mathematical index, 136 cows and heifers from three herds were ranked as high responders (Group 1), average responders (Group 2) or low responders (Group 3) to OVA. Grouping animals by serum antibody response to OVA indicated that animals ranked similarly for antibody to OVA in whey and antibody to *Escherichia coli* in serum. Differences in serum and whey $IgG_1$ concentrations between antibody response groups were not significant. Serum $IgG_2$ concentration however, varied between group, within herd and across time. Whey $IgG_2$ did not differ significantly between antibody response groups within herd. Occurrence of mastitis was negligible for Group 1 animals. In contrast, Group 1 animals from Herd 2, had the greatest occurrence of mastitis while Group 3 had the lowest. Milk somatic cell score (SCS), was lowest for Group 1 animals in Herd 1 and lowest for Group 3 animals in Herd 2, thus supporting the distribution frequency of clinical mastitis in those herds. Herd 3 SCS did not differ significantly between antibody response groups and did not underscore the distribution of clinical mastitis.

The objective of this study was to confirm the existence of high and low antibody response profiles amongst individuals across three herds and to devise a method for quantitatively classifying cows into groups based on antibody response to standardized immunization protocols. Relationships were evaluated between antibody response, immunoglobulin concentration, milk somatic cell score, and disease occurrence with respect to antibody response group.

Materials & Methods

Animals and Treatments

Antibody responses of 136 Holstein dairy cows and heifers from 2 research herds (Herd 1, n=32, 6 heifers and 26 cows; Herd 2, n=67; 34 heifers and 33 cows) and 1 commercial herd (Herd 3, n=37, 8 heifers and 29 cows) were examined from eight weeks prepartum (week −8) based on predicted parturition dates to six weeks postpartum (week 6). Forty nine animals were primiparous heifers, 47 animals were in their second lactation and 41 were multiparous cows (>2 lactations). Antibody responses were evaluated as previously described (Mallard et al., 1997; Ch. V ). Animals received an intramuscular (im) injection of ovalbumin (OVA; Type VII, Sigma Chemical Co., St. Louis, Mo.) and a mastitis endotoxemia preventive vaccine with the manufacturer's adjuvant (Rhône Mérieux *E. coli* J5, Rhône Mérieux, Lenexa, Kans.) at weeks −8 (4 mg) and −3 (2 mg). At parturition (week 0), animals received an additional immunization of OVA in phosphate buffered saline (PBS– 0.1 M, pH 7.4) (2 mg, im). OVA was chosen as an inert test antigen to which these animals had not likely been previously exposed. *E. coli* J5 was used because dairy cows could be expected to have been previously exposed to *E. coli*, a complex antigen, having biological relevance.

Blood and Milk Sampling Schedule

Blood was collected by caudal tail venipuncture at approximately week −8 relative to parturition, and weekly from weeks −3 to 6 relative to parturition. Samples were used to monitor serum immunoglobulin $G_{1\&2}$ and serum antibody to OVA and *E. coli* J5. Colostrum and milk samples were collected to monitor whey $IgG_{1\&2}$ and antibody to OVA in whey. Colostrum was collected at the first milking following parturition. Milk samples were stripped from all quarters approximately 2–4 hr after morning milking. Colostrum and milk samples were stored frozen without preservative at −20° C. until time of whey separation and immunoglobulin quantification.

ELISA for OVA Antibody Detection In Serum and Whey

Antibody to OVA was detected by ELISA, and quantified based on optical density measurements according to a procedure previously described (Mallard et al., 1997; Ch. V). Sera samples (weeks −8, −3, 0, 3, and 6) diluted $\frac{1}{50}$ and $\frac{1}{200}$ were assayed in duplicate. Whey samples (weeks 0,2,3,4, and 6) diluted $1/10, 1/100, 1/400$ and undiluted were assayed in quadruplicate.

ELISA for *E. coli* J5 Antibody Detection In Serum

Antibody response to *E. coli* J5 was measured according to the method previously described (Mallard et al., 1997; Ch. V). Serum samples (weeks −8, −3, 0, 3, and 6) diluted $\frac{1}{1000}$ were assayed in quadruplicate.

Radial Immunodiffusion Assay

Radial immunodiffusion was used according to the method described by Mallard et al. (1992) to determine the concentrations of serum $IgG_{1\&2}$ at weeks 0, 3, and 6 and whey $IgG_1$ at weeks 0, 3, and 6 and whey $IgG_2$ at weeks 0 and 3.

Quantitative Classification of Animals Based on Antibody Response

Serum antibody responses to OVA were evaluated over time intervals, rather than discrete points in time. Individual animal antibody response curves from week −8 to week 6 relative to parturition (week 0) were dissected into components reflecting the response to antigen following immunizations. Primary response was defined as the change in antibody to OVA from week −8 to week −3 relative to parturition following primary immunization at week −8 (Primary=OD value at week−3 minus OD value at week −8). Secondary response was defined as the change in antibody to OVA from week −3 to parturition following secondary immunization at week −3 (Secondary=OD value at week 0 minus OD value at week −3). Tertiary response was defined as the change in antibody to OVA from parturition to week 3 following tertiary immunization at parturition (Tertiary= OD at week 3 minus OD at week 0). Quaternary response was defined as change in antibody to OVA from week 3 to week 6 (Quaternary=OD value at week 6 minus OD value at week 3). Quaternary response was included to observe the change in antibody response between the end of the immediate postpartum period (wk 3) and peak lactation. These responses were added together to give an index of antibody response to OVA between wk −8 and wk +6 relative to parturition as follows:

$y_{index}$=primary+secondary+tertiary+quaternary where,
- y=total antibody response;
- primary, secondary, tertiary, and quaternary responses are as previously defined;
- primary, secondary, tertiary, and quaternary responses when positive, have an equal weight of 1.

Animals which exhibited negative secondary or tertiary responses during the immediate pre-and postpartum period were weighted with a coefficient of 1.5 instead of 1. Only secondary and tertiary responses were weighted in this manner, since this is the period when lowered host resistance mechanisms are thought to contribute to increased occurrence of disease. The coefficients for weighting negative secondary and tertiary responses were optimized using the original biological assessment for grouping animals in the first herd investigated. The quantitative ranking of animals had to reflect the biological assessment of grouping animals based on the magnitude and direction of response to immunization.

The mean of the antibody response index was determined and animals that exceeded one standard deviation above the mean were classified as high responders (Group 1; n=18). Animals that were one standard deviation below the mean were classified as low responders (Group 3; n=23). Animals with an index of antibody response that ranged between one standard deviation below and above the mean were classified as average responders (Group 2; n=95).

Heritability Estimates

Sire and error variance components of serum antibody to OVA were estimates by REML using Variance Component Estimation (VCE) software (Groeneveld, E. 1994). Sire and error variances were used to estimate paternal half-sib heritabilities for serum antibody to OVA at weeks −8, −3, 0, 3, and 6 relative to calving. Approximate standard errors were computed from the variance covariance matrix of sire and error variance component estimates.

Mastitis Occurrence

Occurrence of clinical mastitis was recorded throughout the study period by herd managers. Two or more events of mastitis it were recorded as one event for the study period (Martin et al., 1993). Incidence of mastitis occurrence was calculated by dividing the number of animals within an antibody response group that had at least one disease event by all the animals in that antibody response group, and multiplying this number by 100. Mastitis occurrence was evaluated for associations with antibody response group within each herd, using odds-ratio (OR) (Martin and Meek, 1987). Odds-ratios in this study was calculated on a within herd basis, as the ratio between the rate of mastitis in one antibody response group versus the rate of mastitis in the rest of the herd (i.e. the other two groups). Odds-ratio is the approximate relative risk when the rate of disease in the population is relatively infrequent (<5%) (Martin and Meek, 1987). Odds ratios values were tested for significance using the chi-square test (Martin and Meek, 1987).

Milk Somatic Cell Count

Milk (AM/PM composite sample) was collected weekly to determine somatic cell count (SCC), an indicator or subclinical mastitis. Only SCC which coincided with blood sample collection for each week were used in evaluation. SCC was transformed to somatic cell score (SCS) for analysis. SCS is the natural logarithm of SCC in cells/mL and is calculated as follows:

SCS=$\log_e$(SCC/100)+$\log_e$(2)+3(Shook, 1993)

Statistical Methods

Type III least squares analysis of variance (ANOVA) and corrected means (least square means, LS Means) were generated using the General Linear Models (GLM) Procedure of the Statistical Analysis System (SAS; Helwig and Council, 1982) to evaluate the effects of herd, season-year, cow, antibody response group, parity, week, and their interaction terms on antibody response to OVA and *E. coli*, and immunoglobulin concentration (Table 2). Tests of hypothesis of main effects were tested against the MS for cow. Sources of variation that were not significant were removed from the model in order to generate LS Means. Data that did not show a normal distribution (*E. coli* antibody response, serum $IgG_2$ and whey $IgG_2$) as indicated by the univariate procedure of SAS (SAS, 1982), were transformed to natural logarithms. LS means were converted back to original units from $\log_e$ transformed data. Consequently, standard errors of means are not shown. The Proc CORR procedure of SAS was used to generate Pearson product moment correlation coefficients between immune response parameters. Results were considered to be statistically significant if the p-value was <0.05 and trends were reported at the p-value <0.10.

Results

Serum Antibody to OVA

Figure 3:
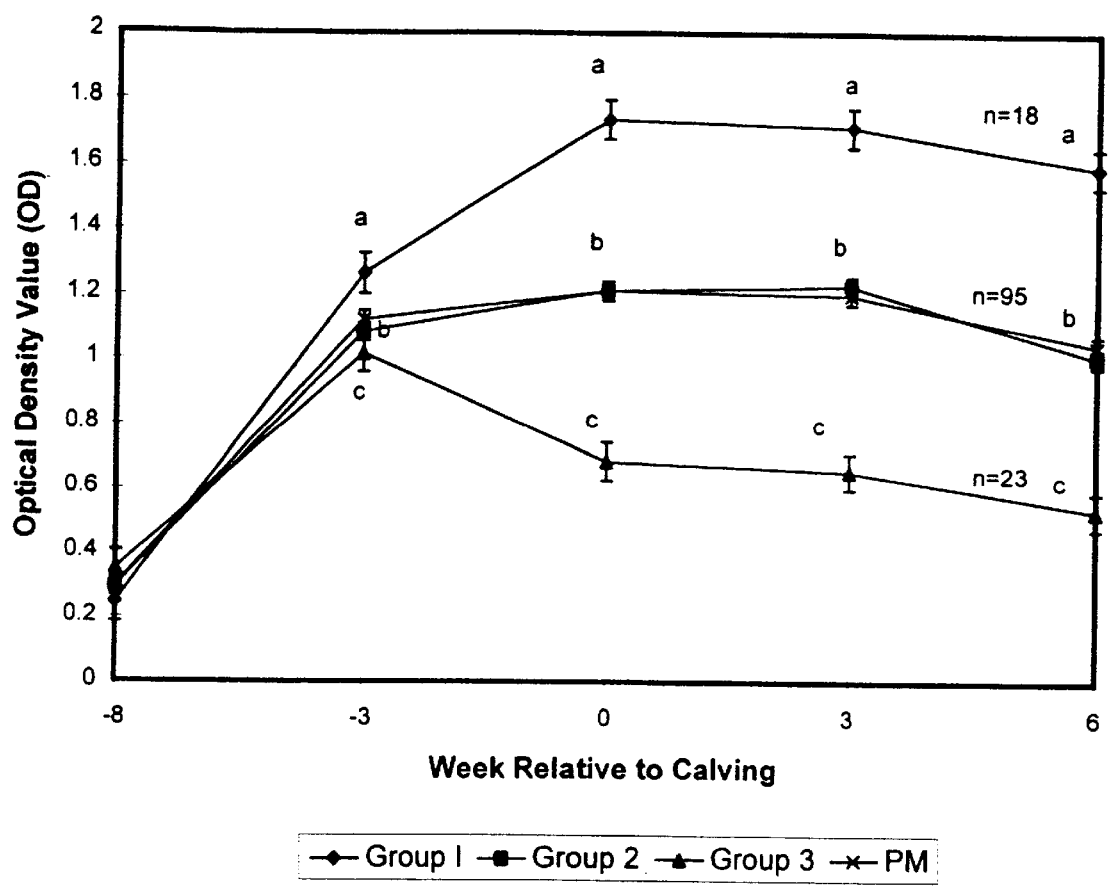
FIG. 3 is a graph showing the anti-OVA antibody levels versus time for the animals of Group 1, Group 2 and Group 3.

Cow, antibody response group, week, and the interaction between antibody response group and week contributed to the variation (P<0.0001) in serum antibody to OVA (Table 2). Herd did not significantly contribute to the variation in serum antibody to OVA. As expected, the rank of antibody response to OVA was Group 1>Group 2>Group 3 except at week −8 prior to immunization and significant differences were noted between all groups at weeks −3, 0, 3, and 6. Population LS means significantly (P<0.0001) increased from pre-immunization (week −8) to week −3 (post primary immunization) in all antibody response groups and OVA antibody response varied significantly across time at weeks −3, 0, 3, and 6. (FIG. 3).

Heritability Estimates of Antibody to OVA

Heritability estimates ($h^2$) of antibody to OVA at weeks −8, −3, 0, 3, and 6 relative to calving were 0.64, 0.62, 0.32, 0.50, and 0.58 respectively. Standard errors could not be calculated by VCE software due to the small sample size evaluated.

These heritability estimates can be used to obtain an Estimated Breeding Value (EBV) of an animal in accordance with the procedure described in PCT/CA93/00533 to Wilkie et al., filed Dec. 9, 1992, entitled "Methodology For Developing A Superior line of Domesticated Animals" (also see, Veterinary Genetics, F. W. Nicholas, Oxford Science Publications, 1987; D. S. Falconer, An introduction to quantitative genetics, Longman, London, 1981). EBV is an indicator of an animal's inherent ability to produce an immune response and its ability to pass genes influencing these traits to offspring. For the purposes of the present invention, EBV values are useful in selecting animals to be bred in order to produce offspring which inherit the level of ability to produce a high immune response when under stress. High immune response may, in part, influence disease resistance.

Whey Antibody to OVA

Herd contributed significantly (P<0.01) to variation in antibody response to OVA and therefore, herds were further analyzed separately. Cow, antibody response group, and week all significantly contributed to the variation in antibody to OVA in whey ($P<0.0001$); however, there was no significant contribution of the interaction term antibody response group and week to the variation in response. For all herds, antibody to OVA in whey by antibody response group, ranked similarly to the antibody responses observed for serum, such that Group 1>2>3. This was consistent for colostral and milk whey from parturition until week 6 of lactation (FIGS. 4A,B, and C). Least squares means of antibody to OVA in whey for all herds declined significantly from parturition to peak lactation. Correlation analysis between antibody to OVA in sera with antibody to OVA in whey, indicated a positive and significant relationship for Herd 1 ($r=0.45$; $P<0.0001$), Herd 2 ($r=0.28$; $P<0.001$) and Herd 3 ($r=0.45$; $P<0.001$) respectively.

Antibody to *E. coli* J5 in sera

Herd contributed significantly ($P<0.003$) to variation in antibody response to *E. coli* J5 and therefore, herds were further analyzed separately (Table 2).

Herd 1

Cow, antibody response group, and week each significantly ($P<0.0001$) contributed to the variation in antibody to *E. coli* J5. Although antibody OD was not significantly different between antibody response groups from week –3 to week 6, the rank of LS Means of antibody response to *E. coli* by antibody response group was Group 1>Group 2>Group 3 (FIG. 5A). Least squares means of antibody to *E. coli* J5 varied during the peripartum period (week –3 to week +3) and up to peak lactation (week +6) and were significantly higher ($P<0.0001$) than pre-immunization antibody at week –8 for all animals, regardless of group (OD value=0.275) (FIG. 5A). Correlation analysis, comparing antibody to *E. coli* J5 with antibody to OVA in sera, indicated a positive and significant relationship ($r=0.56$; $P<0.0001$). The correlation between serum anti-OVA and *E. coli* for Group 1, 2, and 3 was 0.66($P<0.001$), 0.59 ($P<0.0001$) 0.38 ($P<0.06$), respectively.

Herd 2

Cow, antibody response group by parity, parity and week significantly contributed to the variation in antibody response to *E. coli* J5 ($P<0.0001$) for Herd 2. Antibody for Group 3 animals at week –8 was significantly higher (OD value=0.386) than for animals of Group 1 (OD value=0.257; $P<0.005$) and Group 2 (OD value=0.292; $P<0.05$). Optical density values of antibody to *E. coli* for animals in Groups 1 and 2 from week –3 to week 6 was similar to OD values of serum antibody to OVA. Optical density values of antibody were consistently positive following the immunization but were not significantly higher than the population mean. In contrast to serum antibody to OVA, Group 3 animals had OD values that were consistent but not significantly lower than the population mean. (FIG. 5B). Least square means of antibody response to *E. coli* J5 at weeks –3,0,3, and 6 were significantly higher ($P<0.0001$) than pre-immunization antibody at week –8 regardless of group (OD value=0.307). Correlation analysis between serum antibody to *E. coli* J5 and serum antibody to OVA indicated a positive and significant relationship ($r=0.49$; $P<0.0001$). The correlation between antibody to *E. coli* J5 and antibody to OVA for Groups 1, 2, and 3 was 0.65($P<0.0001$), 0.54 ($P<0.0001$), and 0.31 ($P<0.08$) respectively.

Herd 3

Cow grouped within antibody response group, antibody response group, week, and the interaction between week and antibody response group significantly contributed to the variation in antibody to *E. coli* J5 ($P<0.0001$) in Herd 3. In this herd, antibody for Group 1 animals was significantly lower ($P<0.05$) at weeks –8 and –3 compared to Group 2 and 3 animals. At parturition, Group 1 and 2 animals had higher antibody to *E. coli* than Group 3 animals. At weeks 3 and 6, however, the rank of antibody response group for antibody to *E. coli* was similar to the other herds, in that Group 1>Group 2>Group 3 (FIG. 5C). LS Means of antibody to *E. coli* J5 at weeks –3,0,3, and 6 were significantly different across time and were significantly higher ($P<0.0001$) than pre-immunization antibody regardless of group (OD value= 0.224)(FIG. 5C). Correlation analysis between serum antibody to *E. coli* J5 and serum antibody to OVA indicated a positive and significant relationship (0.47; $P<0.0001$). Correlation between serum antibody to *E. coli* J5 and antibody to OVA for Groups 1, 2, and 3 were 0.93($P<0.007$), 0.48 ($P<0.0001$), and 0.36($P<0.006$) respectively.

$IgG_1$ in serum and whey

Analysis of variance indicated that the effect of week contributed significantly ($P<0.05$) and the effect of antibody response group tended ($P<0.07$) to contribute to variation in serum $IgG_1$. Except at week 3, serum $IgG_1$ did not differ significantly between groups; however, Group 1 animals tended to have lower serum $IgG_1$ compared to animals of Group 2 and 3. Least square means of total $IgG_1$ in sera increased significantly ($P<0.0001$) from parturition (430.09 mg/100 mL) to week 3 (687.46 mg/100 mL) and week 6 (799.51 mg/100 mL) (FIG. 6A, population mean). Correlations between serum $IgG_1$ concentration and serum antibody to OVA and *E. coli* were not significant.

The effects of week and parity contributed significantly ($P<0.05$) to the variation in $IgG_1$ concentration in whey. Although antibody response group did not significantly contribute to variation in whey $IgG_1$ (FIG. 6B), LS means of $IgG_1$ concentration (mg/100 mL) at week 0 were significantly lower for Group 1 (768.16 mg/100 mL) and Group 3 (1081.39 mg/100 mL) compared to Group 2 (1381.60 mg/100 mL). Concentration of $IgG_1$ did not differ significantly between groups at weeks 3 and 6. Population LS Means of $IgG_1$ concentration in whey declined significantly from parturition (1046.28 mg/mL) to week 3 (44.93 mg/100 mL, $P<0.0001$). There was no significant change at week 6 (43.25 mg/100 mL). Correlation analysis between whey $IgG_1$ concentration and whey antibody to OVA indicated a positive and significant relationship ($r=0.711$; $P<0.0001$). The correlation coefficients between whey $IgG_1$ and whey OVA antibody response for Groups 1, 2, and 3 were 0.52 ($P<0.0001$), 0.76($P<0.0001$), and 0.69($P<0.0001$), respectively.

$IgG_2$ in sera

Herd contributed significantly ($P<0.0001$) to variation in serum $IgG_2$ concentration and therefore, herds were analyzed separately.

Herd 1

Effects of cow and the interaction between antibody response group and week contributed significantly ($P \leq 0.05$) to variation in $IgG_2$ concentration for Herd 1. Antibody response group did not significantly contribute to the variation in $IgG_2$; however, LS means of $IgG_2$ in sera at weeks 0 and 3 was lowest for Group 1 animals and highest for Group 3 animals. This trend reversed at week 6, such that Group 1 animals had the highest concentration of $IgG_2$ and Group 3 animals had the lowest. LS Means of $IgG_2$ significantly increased from 1019.43 mg/100 mL at parturition to 1534.56 mg/100 mL at week 3 but declined significantly at week 6 to 1103.23 mg/100 mL. Correlation analysis, between antibody to OVA in sera and concentration of $IgG_2$, indicated a negative and significant relationship ($r=-0.23$, $P<0.03$). Correlations between antibody to OVA with serum $IgG_2$ concentration indicated for Group 1, 2, and 3 were 0.07(ns), −0.35(P<0.004) and −0.33 (ns). Significant correlations were not observed between *E. coli* antibody response and serum $IgG_2$ concentration, even when examined by group.

Herd 2

Cow significantly contributed (P<0.05) to the variation of serum $IgG_2$ concentration while antibody response group and the interaction between antibody response group and parity tended to contribute to the variation in serum $IgG_2$ concentration. At parturition, groups did not significantly differ in serum $IgG_2$. At week 6, LS means of $IgG_2$ concentration for animals in Group 1 were significantly higher than for Group 3 animals. Least square means of $IgG_2$ concentration did not differ significantly between weeks 0, 3, and 6. Correlation analysis between serum $IgG_2$ concentration and serum antibody to OVA indicated a positive and significant relationship (r=0.15; P<0.03). Significant correlations were not observed between serum $IgG_2$ concentration and serum antibody to OVA or serum antibody to *E. coli* J5.

Herd 3

Cow (P<0.005) and parity (P<0.04) contributed significantly to the variation of serum $IgG_2$. concentration. Week (P<0.09) tended to contribute to variation in serum $IgG_2$ concentration. Antibody response group did not significantly contribute to variation in serum $IgG_2$ concentration. Correlations between serum $IgG_2$ concentration and antibody to OVA and *E. coli* were not significant.

$IgG_2$ in whey

Herd contributed significantly (P<0.03) to the variation in serum $IgG_2$ concentration and therefore, herds were analyzed separately.

Herd 1

Week contributed significantly to variation in $IgG_2$ concentration in whey. Whey $IgG_2$ concentration did not differ significantly between groups (FIG. 8A). LS Means of total $IgG_2$ concentration in whey declined significantly from week 0 (327.34 mg/100 mL) to week 3 (26.31 mg/100 mL). Correlation analysis between whey $IgG_2$ concentration and antibody to OVA indicated a positive and significant relationship (r=0.7; P<0.0001). Correlations between whey $IgG_2$ concentration and whey antibody to OVA were r=0.9 (P<0.002), 0.6 (P<0.0003), and 0.8 (P<0.02) for Groups 1, 2, and 3, respectively.

Herd 2

None of the parameters in the linear model contributed significantly to variation in whey $IgG_2$ concentration, and, therefore, LS means were not estimable. Correlations between whey $IgG_2$ concentration and whey antibody to OVA indicated a positive and significant relationship (r=0.3, P<0.009). Correlations between whey $IgG_2$ and whey antibody to OVA was 0.2(ns), 0.5(P<0.0001), and 0.6 (ns) for Groups 1, 2, and 3, respectively.

Herd 3

Antibody response group and week significantly contributed to the variation in whey $IgG_2$ concentration. Whey $IgG_2$ concentration did not significantly differ between groups at parturition, and responses at week 3 could only be estimated for Group 3 animals since responses for Groups 1 and 2 were either low or too low to be detected. Correlation analysis indicated no significant relationships between whey $IgG_2$ concentration and whey antibody to OVA.

Mastitis Occurrence

Figure 7:
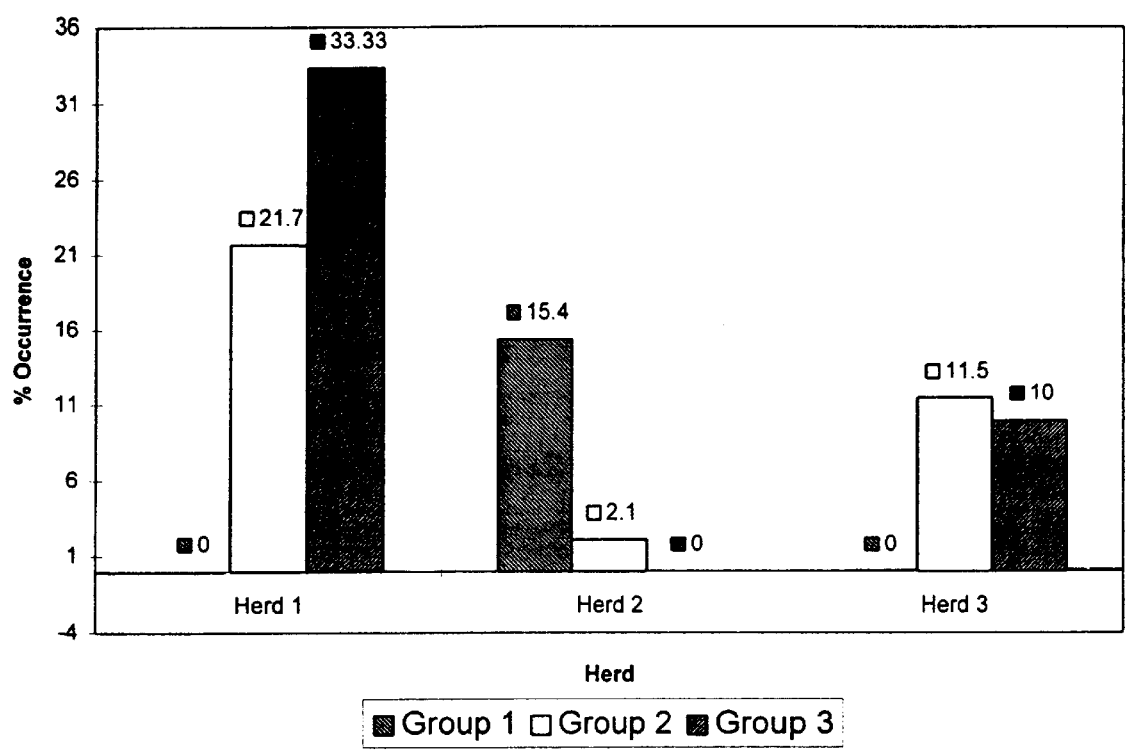
FIG. 7 is a bar graph showing the rate of mastitis occurrence based on antibody response within a herd.

Percent mastitis occurrence varied between groups and between herds. Rates of occurrence of clinical mastitis are presented in table 3. Mastitis did not occur in Group 1 of either Herds 1 or 3. Mastitis occurrence in Herd 1 was 21.7% and 33.3% for Groups 2 and 3, respectively. Mastitis occurrence in Herd 3 was 11.5 and 10% for Groups 2 and 3 respectively. However, in Herd 2, Group 1 animals had the highest occurrence of mastitis (15.4%) which exceeded the percent occurrence of mastitis in Groups 2 (2.1%) and 3 (0%) (FIG. 7). Animals with mastitis in Herds 1 (n=6 heifers; n=26 cows) and 3 (n=8 heifers; n=29 cows) were in their second or greater parity. Animals with mastitis in Herd 2 (n=34 heifers; n=33 cows) were all heifers. Across all herds, animals in Group 3 had the highest rate of mastitis occurrence (13.6%) compared to Group 1 (11.1%) and Group 2 (9.3%) (Table 3). These differences across herds however, were not significant.

Odds—Ratio for Mastitis

Within herd, odds-ratio calculations comparing animals of one antibody response group with the other two groups indicated that only animals in Group 1 of Herd 2 had a statistically significant higher relative risk of having a mastitis event (by 7.57 times) compared to the animals in the rest of the herd. Although the risk of mastitis occurrence within Group 3 of Herds 1 and 3 was 2.16 and 1.8 times greater (respectively) than for other groups, these values were not significant.

Somatic Cell Score

For Herds 1 and 2, cow, week and antibody response group significantly contributed to the variation in SCS (Table 2). In Herd 3, only the effect of cow within antibody response group accounted for the variation in SCS. Somatic cell score was significantly different between groups in Herds 1 and 2 but not Herd 3. LS Means of SCS in Herd 1 were lowest for the high antibody responder animals, and greatest for the low antibody responder animals at weeks 3,4,5 and 6 following parturition (FIG. 8A). Conversely, LS Means of SCS in Herd 2 were significantly lower for low antibody responder animals compared to high antibody responder animals (FIG. 8B).

Discussion

Example 1 indicated that animals could be classified according to the amplitude and direction of their individual OVA antibody response profiles, and that this ranking had some association with mastitis occurrence. This herd, Herd 1 used in Example 1, was evaluated with two more herds, Herds 2 and 3. The objective of the current study was to verify the relevance of high and low antibody response profiles across the three herds and to determine if it would be possible to develop a quantitative measure of classification for antibody response that reflected the initial qualitative assessment of animals. The results indicated substantial variation in antibody response to OVA from the peripartum period to peak lactation and that animals could be ranked using a quantitative index. Animals that ranked high, average or low for serum antibody response, also ranked similarly for whey antibody to OVA. Serum antibody to OVA was expected to be significantly different between groups since animals were purposefully classified into high or low groups based on their total antibody response curve slopes as either less or greater than one standard deviation from the population mean of the total index of antibody response, but antibody in whey was not classified in this manner. Whey antibody responses within each herd demonstrated that high and low serum OVA antibody responses were also high and low in whey, respectively.

In all herds, antibody to the more biologically relevant antigen, *E. coli*, ranked similarly to the ranking for antibody to OVA, particularly at weeks 0, 3, and 6 after parturition. This can help identify animals which respond best following immunization. Nonetheless, ranking based on response to OVA may be preferable since OVA is not normally encountered in the dairy cow's environment thus eliminating the possibility of pre-existing antibody to OVA. In theory, any antibody to OVA responses are expected to be evoked only by the immunization protocol. Further, antibody to *E. coli* was significantly affected by herd making comparisons of populations difficult.

Previous mathematical approaches to assess variation in innate and immune host resistance mechanisms during the peripartum period that have included work by Detilleux et al. (1994) who used a fitted polynomial model to assess hyporesponsiveness during the peripartum period. These results were utilized in an animal model to detect variation between daughters of various sire groups. This method of assessment of hyporesponsiveness was not suitable for this study since it requires many data points across time. Variation in antibody to OVA was partitioned using a simple model wherein animals that had any hyporesponsiveness in the immediate peripartum period were ranked lower compared to animals that responded consistently and positively to OVA immunization.

Antibody response to ovalbumin OVA in dairy calves has been reported by Burton et al. (1989) to be heritable ($h^2=0.48$). Though standard errors of sire and error variances could not be calculated, heritability estimates, of serum antibody to OVA were high ($h^2>0.50$) at time points before and after calving. That the heritability estimate at parturition ($h^2=0.32$) was lower than at other time points evaluated, may be explained by the complex interactions that occur between hormones and the immune system during the immediate postpartum period. Taken together, these results indicate a possible significant genetic component to bovine antibody to OVA, although heritability may be lower at times when the dairy cow experiences the physical and metabolic stresses of parturition and early lactation. These estimates will need to be confirmed on larger populations but suggest that genetic selection for increasing antibody responsiveness is possible, if deemed significant, in the peripartum cow.

Correlation analysis between antibody to OVA in serum or whey and $IgG_{1\&2}$ by antibody response group indicated some significant relationships. However, antibody response group in the statistical model did not significantly, but tended to contribute to the variation in serum or whey $IgG_{1\&2}$. Serum and whey $IgG_2$ distributions by antibody response group differed for each herd and consequently, significant relationships between groups that are common to all herds were difficult to determine. Unpublished data from this laboratory and other studies have indicated that the serum antibody to OVA is largely of the $IgG_2$ subclass (Gilbert et al., 1994) and therefore, may have indicated some association between the two parameters investigated. However, since herd differences existed, it was not feasible to relate previously published results with $IgG_2$ concentration investigated in the current study.

The incidence of mastitis by antibody response group was not consistent between herds. In Herd 1 and Herd 3, the incidence of mastitis was greatest for animals with low antibody response (Group 3). All animals within these herds that had mastitis were in their second or later parity. Though not significant, odds-ratio assessment for these herds indicated that there was a 2.16 and a 1.80 times greater chance of having a mastitis event if animals were classified in Group 3 versus Groups 1 & 2. In contrast, animals from Herd 2 had a very different distribution of mastitis occurrence among groups. Animals in Group 1 had the greatest rate of mastitis occurrence and according to the odds-ratio parameter, were 7.57 (P<0.05) times more likely to have a mastitis event. Further, all animals that had mastitis within Herd 2 were first parity heifers. Differences in herd management and the distribution of heifers and cows within each herd and antibody response group, may help explain the differences in the distribution of mastitis occurrence. Herd 1 (n=6 heifers; n=26 cows) and Herd 3 (n=8 heifers; n=29 cows) had a greater ratio of cows to heifers within each antibody response group, while Herd 2 (n=34 heifers; n=33 cows) heifers and cows were more evenly distributed among all antibody response groups. Previous studies have acknowledged an increase in the rate of occurrence of mastitis with advancing parity (Todhunter et al., 1995, and McClure et al., 1994) which may explain the disparity among herds. The unexpected distribution of mastitis in the Herd 2 might further be explained by a more recent investigation from Finland (Myllys et al., 1995) which indicated that in well managed herds with high milk production and low somatic cell counts, the rate of the treatment of heifers that had a mastitis episode increased from 1.8% to 4.4% over an 8 year period. In contrast to clinical mastitis observed in second parity and multiparous cows, that study further indicated that mastitis in heifers only resulted in small production losses, did not pre-dispose heifers to more mastitis or other diseases later in lactation, and the recovery rate from mastitis was high as indicated by a rapid decline in somatic cell counts (SCC) following infection. This may indicate that mastitis in heifers and in cows cannot be compared directly. That disease occurrence in this study was not consistent among herds, may be explained by a number of factors including the relatively small sample size evaluated, environmental (management) differences, distribution of heifers and multiparous cows, and type of mastitis (subclinical vs. clinical, and the infecting pathogen).

Alterations in antibody response and the incidence of mastitis indicates that immune response phenotype can be a potential phenotypic marker for disease resistance and/or susceptibility.

It was determined that sufficient individual variation in antibody response to OVA existed such that animals could be readily classified quantitatively into high, average and low response groups using a mathematical index based on OD values of antibody response profiles from week −3 to week 6 relative to parturition. Detection of immune response traits such as antibody response, which associate well with disease resistance can provide a useful phenotype to begin selective breeding of dairy cattle for improved inherent immune responsiveness and disease resistance.

Example 3

Relationships Between Cell Mediated Immune Response (CMIR) and Antibody Response in Periparturient Holstein Dairy Cows To examine variation in cell mediated immune response (CMI) response as a function of peripartum serum antibody response to ovalbumin (OVA), 136 Holstein cows and heifers from three herds were evaluated from three weeks before parturition to week 6 following parturition for lymphocyte proliferative responses to OVA and concanavalin A (Con A), delayed type hypersensitivity (DTH) to purified protein derivative (PPD) of tuberculin, differential complete blood cell counts, and somatic cell score (SCS). Using a mathematical index, animals were quantitatively classified based on their antibody responses to OVA into high (Group 1), average (Group 2) or low (Group 3) antibody response phenotypes. Lymphocyte proliferative responses to OVA (r=−0.28; P<0.0001) and Con A (r=−0.14; P<0.0001) were negatively correlated with antibody to OVA. Animals classified as low antibody response (Group 3) had the highest unstimulated and OVA-stimulated lymphocyte proliferative responses. Proliferation of unstimulated lymphocyte proliferative responses was depressed between week −3 and parturition. Con A stimulated lymphocyte proliferative responses were also depressed at parturition but this was significant ($P<0.05$) only in Group 1 which had high antibody response to OVA. Although animals exhibiting high and low DTH response phenotypes could be identified, DTH was not significantly associated to anti-OVA response. Delayed type hypersensitivity at 48 and 72 hours were negatively and significantly correlated with unstimulated ($r=−0.21$; $P<0.002$; $r=−0.17$; $P<0.01$) and Con A stimulated ($r=−0.29$, $P<0.0001$; $r=−0.28$, $P<0.0001$) lymphocyte proliferation, respectively. Lymphocyte number in peripheral blood declined significantly from week −3 to week 0. Milk somatic cell score (SCS) was negatively, and significantly, correlated with in vitro lymphocyte proliferative response to OVA in Herd 2 ($r=−0.13$; $P<0.0001$) only. SCS was not significantly correlated with Con A stimulation. SCS was also negatively and significantly correlated with DTH at 48 hours post-challenge ($r=−0.21$; $P<0.01$). Cumulative results indicate a variety of negative phenotypic associations between measures of antibody response and CMI, and among indicators of CMI. Since both antibody and CMI are important in host resistance to infectious disease, use of a selection index would be required to simultaneously enhance both parameters, assuming there are beneficial associations with cow health.

Introduction

Innate and immune response mechanisms of dairy cows are impaired during the peripartum period. Neutrophil function (Detilleux et al., 1995, Kehrli et al., 1989b, Gilbert et al., 1994 and Cai et al., 1988), complement activity (Detilleux et al., 1995), conglutinin concentration (Detilleux et al., 1995), IgG$_1$ (Detilleux et al., 1995), milk somatic cell count (Shuster et al., 1996) and lymphocyte proliferation (Saad et al., 1989; Kehrli et al., 1989a; Ishikawa, 1987; Kashiwazaki, 1985; Wells et al. 1977) are impaired either pre- or postpartum. Some investigations however, indicated that not all animals exhibit a period of hyporesponsiveness, at least with respect to antibody response. Mallard et al. (1997; Ch. V) demonstrated that peripartum antibody responses to ovalbumin (OVA) are continuous in nature, and that this variability allowed animals to be readily classified as low, average or high antibody producers. Further, animals of the high group had lower mastitis occurrence than animals with average and low antibody response (Mallard et al., 1997; Ch. II & V).

Given that both antibody and cell mediated immune mechanisms are involved in response to infectious disease, it is relevant to evaluate the relationships between antibody and indicators of CMI. Since negative associations have been reported between antibody and aspects of CMI, animals categorized on the basis of antibody response to OVA may have the inverse rank for CMI responses (Biozzi et al., 1972; Arthur and Mason, 1986). This would have practical implications if antibody response was proposed as a candidate marker of disease resistance of dairy cattle. The objectives of this paper were to evaluate CMI responses with respect to antibody response group and to determine if any associations exist with SCS as an indicator of udder health.

Materials and Methods

Experimental Design

To evaluate phenotypic variation in CMIR of dairy cattle, 136 Holstein animals from two research herds Herds 1 and 2, respectively) and one commercial herd (Herd 3) were examined every three weeks from week −3 to six weeks postpartum (week 6). Eighty-eight animals were multiparous cows and 48 were primiparous heifers. To stimulate immune response during the peripartum period, animals received an intramuscular (im) injection of ovalbumin (OVA, Type VII, Sigma Chemical Co., St. Louis, Mo.) and with a mastitis endotoxemia preventive vaccine, an Rc mutant of *Escherichia coli* O111:B4 (Rhône Mérieux *Escherichia coli* J5, Rhône Mérieux, Lenexa, Kans.) approximately eight weeks (4 mg OVA) and three weeks (2 mg OVA) prior to predicted parturition dates. At parturition (week 0), animals received a single im immunization injection of OVA (2 mg) dissolved in phosphate buffered saline (PBS−0.1 M, pH 7.4). Using a mathematical index, animals were classified based on serum antibody to OVA into high (Group 1), average (Group 2) or low (Group 3) response groups (Ch.II). At weeks −3, 0, 3, and 6, PBMC were stimulated in vitro with OVA (5 mg/mL) and concanavalin A (Con A) (5 mg/mL), and proliferative response was measured as described below (section 2.4). For lymphocyte proliferative response, week-3 responses of animals that calved early or later than predicted parturition dates were adjusted to reflect the true time point evaluated (i.e. week −2 or week −4). In order to evaluate delayed type hypersensitivity (DTH) as a measure of CMIR, a subset (n=36; 15 cows and 21 heifers) of animals from Herd 2 were given a 1.5 mg/mL intradermal injection of the Bacillus Calmette Guerin (BCG; Connaught, Mississauga, Ont.) vaccine in the left caudal tail fold at week 1 postpartum.

Delayed Type Hypersensitivity

Animals vaccinated with BCG (1.5 mg/mL) received a 0.1 mL intradermal injection of the PPD of tuberculin (250 US Tuberculin Units; Connaught, Mississauga, Ont.) and for control, received 0.1 mL injection of PBS at week 3 int the right caudal tail fold. The PPD was injected in a designated site approximately 4 cm from the PBS designated site and both were located 10 cm from the base of the tail. Prior to injection, sites were encircled with a coloured marker and double skin thickness measurement was taken in triplicate (time=0), using Harpenden skin thickness calipers (John Bull, England, UK). Forty eight and 72 hours after intradermal injection of PPD and PBS, double skin thickness was measured again. Skin thickness increase at 48 and 72 hours was calculated as follows:

$$\% \text{ increase in skin thickness}=(((A-B)/B)-(C-D)/D)))\times 100$$

where A=mean test thickness (at time=48, 72 hours)
B=mean of pre-test thickness (at time=0 hours)
C=mean of control thickness (at time=48, 72 hours)
D=mean of pre-control thickness (at time=0 hours)

Prior to conducting these experiments it was confirmed that the herd was tuberculin test negative on the basis of negative results in 10 randomly selected animals.

Lymphocyte Proliferative Response

Lymphocyte proliferation assays were performed according to the procedure of Chang et al. (1993). Briefly, blood was centrifuged (850×g, 15 min) and whole blood buffy coats were diluted in phosphate buffered saline (PBS 0.1 M, pH 7.4). Peripheral blood mononuclear cells (PBMCs) were separated from diluted whole blood buffy coats by density gradient centrifugation (1000×g, 30 min) using aqueous Histopaque 1.077 (Sigma Chemical Co. St. Louis, Mo.) Cell pellets were washed by centrifugation in PBS (400×g, 7 min) and suspended in culture medium (Rosewell Park Memorial Institute; RPMI-1640, and 100 I.U. penicillin-streptomycin, prepared by Central Media Laboratory; Ontario Veterinary College, University of Guelph, Guelph, Ont.) and 10% FCS and brought to a final concentration of $2.0 \times 10^6$ cells/mL. To determine specific clonal proliferative responses to antigen, a stock solution (50 µg/mL) of OVA (Sigma Chemical Co., St. Louis, Mo.) dissolved in RPMI-1640 was prepared and stored in small aliquots at −70° C. Five µg/mL of OVA was added to each of 6 replicates of test PBMC in 96 well flat-bottom plates (Nunc, Fisher Scientific, Don Mills, Ont.). Medium only was added to 6 well replicates of PBMC as non-stimulated controls, to obtain background values for unstimulated cell proliferation. The mitogen, concanavalin A (Con A; Sigma Chemical Co., St. Louis, Mo.) prepared from stock solution (50 µg/mL) and diluted to (5 µg/mL) for addition was added to 6 replicates of cells on a plate with 6 non-stimulated control replicates. Following 24 h of incubation with OVA or Con A(37° C., 6% $CO_2$) cells were incubated for 18 h with 0.5 µCi methyl tritiated thymidine per well (ICN Biochemical, Canada Ltd. Montreal, Que.). Plates were frozen until cells were harvested using a plate harvesting system (LKB Wallac, Turku, Finland) onto fiberglass filter mats (LKB Wallac, Turku, Finland). Radioactivity was recorded as counts per minute (cpm) by a beta plate liquid scintillation counter (LKB Wallac,Turku, Finland).

Flow Cytometric Assay for the Detection of CD Surface Molecules of Peripheral Blood Lymphocytes Cell phenotypes were characterized after stimulation with either Con A or OVA, by staining with monoclonal antibodies recognizing five cell surface markers as described by Van Kampen and Mallard (1997). The monoclonal antibodies were kindly provided by Dr. Jan Naessens of ILRI (ILRI, Nairobi, Kenya) and included antibodies to the following bovine cell surface markers: CD2+(IL-A43), CD4+(IL-A11), CD8+(IL-A105), WCI (IL-A29), and IgM (IL-A30). Peripheral blood lymphocytes from a subset of animals (n=10) from Herd 2 (n=7) and Herd 3 (n=3) were evaluated for these lymphocyte cell surface markers at weeks −3, 0, 3, and 6 relative to parturition. Lymphocytes were prepared and cultured as previously described for lymphocyte proliferation assays, however, each 96 well plate was divided into quadrants each with 24 wells. Twenty four replicates each of Con A stimulated (5 µg/mL), OVA stimulated (at 5 µg/mL and 20 µg/mL) and non-stimulated controls were cultured for 42 hours (the same total duration used in the lymphocyte proliferation assays). After 42 hours, cells were harvested by pipette, washed with PBS and transferred to 10 mL glass test tubes. Cells were centrifuged (400×g,10 min), and supernatants decanted and cells were resuspended in 250 µL PBS+ 0.1 M sodium azide (Fisher Scientific, Fairlawn, N.J.). Immunostaining was performed in 96-well round-bottom plates (Corning, New York, N.Y.). Fifty µL of cells and 50 µL of diluted primary antibody were added to each well and plates were incubated (20 min, rt). After incubation, 100 µL of PBS 0.1 M Azide was added to each well to wash the cells. Cells were suspended by mixing on a shaker and centrifuged (400×g, 6 min). Supernatants were then removed using an aspirator. This washing procedure was performed twice. Fifty µL of FITC-conjugated goat anti-mouse IgG(H+L) (Cedarlane Laboratories, Hornby, Ont.) was then added to the cells and cells were incubated (20 min, rt). After incubation, plates were washed twice as described above. Cells were fixed in 1% paraformaldehyde and transferred into 3 mL polystyrene tubes (Becton Dickinson, Lincoln Park, N.J.) containing 300 µL of 1% paraformaldehyde. Tubes were covered with Parafilm and refrigerated (4° C.) µg/mL until time of assay.

A FACS Scan flow cytometer (Becton Dickinson, Lincoln Park, N.J.) was used to acquire lymphocyte subset data. LYSIS II software (Becton Dickinson, Lincoln Park, N.J.) was used for analyzing data describing the frequency of positively stained cells. Lymphocytes were gated out from other populations based on their forward and side scatter characteristics. Histograms representing fluorescence of cells expressing CD2 (pan T cell), CD4 (helper T cells), CD8 (cytotoxic/suppressor T cells), WC1 (γδ T cells), and IgM (B cells) cell surface markers were plotted for each cow, timepoint, and culture condition observed. The region of background fluorescence was established with the negative control marker, M1. Events accumulated to the right of this marker were considered positive. (Appendix III, FIG. 2).

Complete Blood Cell Counts

Complete Blood Cell Counts were determined by the Clinical Pathology Laboratory at the Ontario Veterinary College, University of Guelph, Guelph, Ontario, Canada. Counts included the percent and total number of leukocytes, erythrocytes, banded neutrophils, segmented neutrophils, lymphocytes, monocytes, basophils, and eosinophils.

Milk Somatic Cell Counts

Weekly milk somatic cell counts (SCC), an indicator of subclinical mammary gland infection, were obtained from animals of Herd 1 using the weekly sampling service offered by the Ontario Dairy Herd Improvement Corporation (Ontario DHI). Weekly samples of animals in Herd 2 and Herd 3 sampled 1–4 hours after morning milking were tested for SCC by the Mastitis Laboratory at the Ontario Veterinary College, University of Guelph, Guelph, Ontario Canada. Monthly SCC were obtained from Ontario DHI for all three herds. Somat cell counts were transformed to somatic cell score (SCS) for analysis. Somatic cell score is the log-linear transformation of SCC in cells/mL and is calculated as follows:

$$SCS = \log_e(SCC/100) \div \log_e(2) + 3 \text{ (Shook, 1993)}$$

Statistical Methods

Type III least squares analysis of variance (ANOVA) and corrected means (least square means, LS Means) were generated using the General Linear Models (GLM) Procedure of the Statistical Analysis System (SAS; Helwig and Council, 1982) to evaluate the effects of herd, season-year, cow, antibody response group, parity, week, and their interactions on lymphocyte proliferation to OVA and Con A, DTH, complete blood cell counts and SCS (Table 4). Sources of variation were tested against the mean square (MS) for cow grouped within antibody response group and parity to determine significance in the GLM. Sources of variation that were not significant were removed from the model in order to generate LS Means. Unstimulated lymphocyte proliferation was used as a covariate in the GLM for OVA and Con A stimulated lymphocyte proliferation since some variability in unstimulated responses between dairy animals has been described (Burton et al., 1991). Data that did not show a normal distribution (unstimulated lymphocyte proliferation, OVA and Con A stimulated lymphocyte proliferation, and total neutrophils) as indicated by the univariate procedure of SAS (Helwig and Council, 1982), were transformed to natural logarithms. Lymphocyte count data was transformed using a square root transformation. Least square means were converted back to original units from $\log_e$, or square root transformed data. Consequently, standard errors of means are not shown. The Proc CORR procedure of SAS was used to generate Pearson product moment correlation coefficients. Results were considered to be statistically significant if the P-value was <0.05 and trends were reported at the p-value <0.10.

Results

Unstimulated in vitro lymphocyte proliferation

Individual cow, week relative to parturition, the interaction between antibody response group and week contributed significantly to variation in unstimulated lymphocyte proliferation (Table 4). Herd did not significantly affect the variation in unstimulated lymphocyte proliferative response. Unstimulated lymphocyte proliferative response significantly ($P<0.05$) declined at parturition, but increased again at week 3 of lactation. When these responses were evaluated by antibody response group, at weeks −3, 0, 3, and 6, lymphocyte proliferative responses were significantly lower ($P<0.01$) for animals of the high antibody response group and significantly higher ($P<0.05$) for animals of the low antibody response group (FIG. 9A). The correlation between antibody to OVA and unstimulated lymphocyte proliferation across all groups was negative and significant ($r=-0.26$, $P<0.0001$; Table 5).

OVA stimulated lymphocyte proliferation

Individual cow and the interaction between antibody response group and parity, replicate and unstimulated lymphocyte proliferation, significantly contributed to variation in OVA lymphocyte proliferative response (Table 4). Herd did not significantly contribute to the variation in lymphocyte proliferative responses to OVA. Least square means of lymphocyte proliferation did not differ significantly across weeks. At weeks 0 and 3, lymphocyte proliferation to OVA was significantly lower for Group 1 ($P<0.01$) compared to Group 3. At week 6, the response of these groups was reversed. The correlation between antibody to OVA across all groups and OVA stimulated lymphocyte proliferation across all groups was negative and significant ($r=-0.27$, $P<0.0001$).

Con A Stimulated Lymphocyte Proliferation

Individual cow, parity, the interaction between parity and antibody response group, antibody response group, week and the interaction between week and antibody response group significantly contributed to variation in Con A stimulated lymphocyte proliferation. Herd did not significantly contribute to variation in lymphocyte proliferation to Con A. Least square means of Con A stimulated lymphocyte proliferation declined, though not significantly, from week −4 and −3 to parturition (FIG. 9C). Proliferative responses increased significantly ($P<0.05$) at week 3 compared to parturition. Group 1 animals had the highest Con A-induced lymphocyte proliferation at weeks −4, −3, 0, 3, and 6. Response decreased in Group 1 (high response) animals from week −4 to parturition and significantly increased from parturition to week 3. Antibody response to OVA and Con A-stimulated lymphocyte proliferation was negatively correlated ($r=-0.14$, $P<0.0001$).

Delayed Type Hupersensitivity (DTH)

Antibody response category did not significantly affect variation in DTH response. Cutaneous DTH responses at 48 and 72 hours were highly correlated ($r=0.90$; $P<0.0001$). At 48 hours DTH ranged from 0 to 75% skin thickness increase with a mean of 30.7% while 72 hour values ranged from 0 to 79% with a mean of 29.5%. Antibody response to OVA at week 3 did not correlate significantly with DTH responses. The DTH response at 48 and 72 hours was negatively and significantly correlated with unstimulated ($r=-0.21$; $P<0.002$; $r=-0.17$; $P<0.01$) and Con A ($r=-0.29$; $P<0.0001$; $r=-0.28$; $P<0.0002$) stimulated lymphocyte proliferative responses, respectively. DTH response at 48 hours was significantly and negatively ($r=-0.21$; $P<0.01$) correlated with SCS.

Differential Complete Blood Cell Counts

Figure 11:
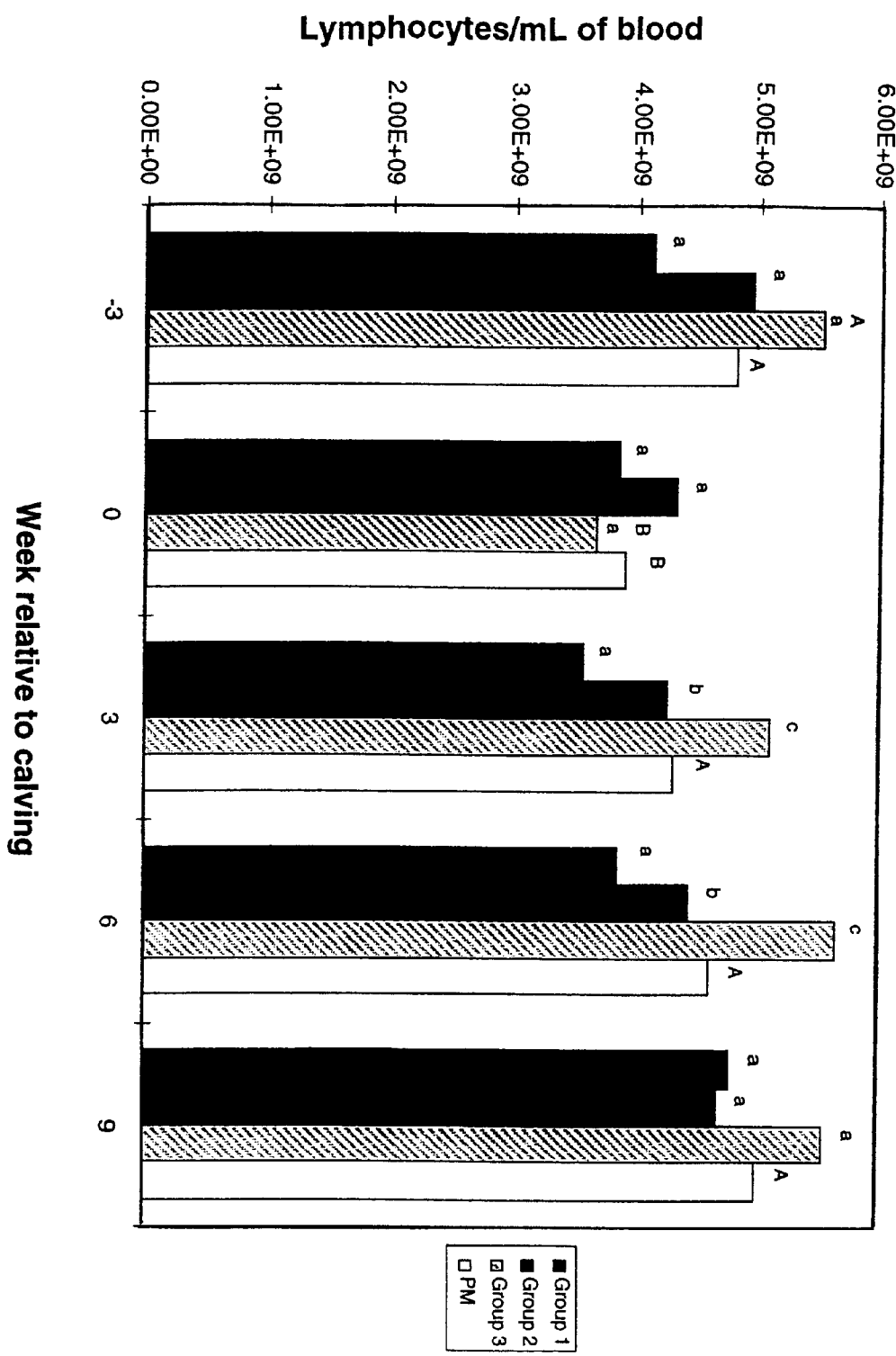
FIG. 11 is a bar graph showing the lymphocyte counts versus time for the animals in Group 1, Group 2 and Group 3.

Counts of segmented neutrophils varied between animals within all herds, but were not significantly affected by week or antibody response group. Since banded neutrophils were not observed in every animal, a general linear model could not be used to explain the variation in this response. Counts of lymphocytes declined significantly ($P<0.05$) from week −3 ($4.8\times10^9$ cells/mL) to week 0 ($3.9\times10^9$ cells/mL) (FIG. 11). Significant differences in lymphocyte numbers between antibody response groups were observed only at weeks 3 and 6 of lactation when Group 3 animals had significantly ($P<0.05$) more lymphocytes compared to Groups 1 and 2. Across time, only Group 3 animals had a significant decline ($P<0.05$) in percent and total numbers of lymphocytes from week −3 to parturition.

Milk Somatic Cell Score

For Herds 1 and 2, individual cow, week relative to parturition and antibody response group contributed significantly to variation in response. In Herd 3, only the effect of cow accounted for the variation in response. Least square means of SCS in Herd 1 were lowest for animals of the high antibody response group, and greatest in animals of the low antibody response group at weeks 3,4,5 and 6 following parturition. Conversely, LS Means of SCS in Herd 2 were significantly lower for animals of the low antibody response group compared to animals of the high antibody response group. Somatic cell score was negatively and significantly correlated with OVA stimulated lymphocyte proliferative responses in Herd 2 ($r=-0.13$; $P<0.0001$). Delayed type hypersensitivity at 48 hours was negatively and significantly correlated with SCS ($r=-0.21$; $P<0.01$).

Lymphocyte Subsets After Culture

Although lymphocyte subset proportions varied depending on week relative to parturition (week −3 to week +6), the percentage of cells positively expressing CD2+, CD4+, CD8+, WC1+, and IgM were not significantly different between unstimulated control and treatment groups. Cells expressing IgM were most frequent (38–60%) regardless of treatment and WC1+ cells were least numerous (5–15%) at all time points. Only at week 3 relative to parturition were there more Con A-stimulated lymphocytes expressing IgM (60%) compared to unstimulated controls (40%) or OVA stimulated PBMC (38–40%).

Discussion

The previous example indicates that in the peripartum period, Holstein animals varied in antibody to OVA and that animals could be grouped into high, average and low groups based on this response. The objectives of this study were to evaluate CMI responses with respect to antibody response group and to evaluate possible associations with SCS as an indicator of udder health.

In the current study, animals with the highest antibody response (Group 1) had significantly ($P<0.05$) lower unstimulated and OVA-stimulated lymphocyte proliferative responses during the peripartum period while low antibody response animals (Group 3) had the highest lymphocyte proliferative responses. Con A-induced lymphocyte proliferation and antibody response to OVA however, were not inversely related, since animals with high antibody response also had high Con-A stimulated lymphocyte proliferative responses, indicating that relationships between antibody and CMI may vary depending on the measurements made. Although no differences in DTH were observed between antibody response groups, DTH responses were demonstrated to vary between individuals. This variation in DTH, a measure of CMI, indicates that it may be possible to select animals for enhanced CMI.

Lymphocyte counts declined in agreement with Saad et al.(1989). Group 3 animals, which that had higher unstimulated and OVA-stimulated in vitro lymphocyte proliferation, had the sharpest decline in lymphocyte numbers at parturition. This may indicate that, although absolute numbers were decreased, lymphocyte function may have been better in that particular group of animals. Neutrophil counts have been reported to decline from week −3 to parturition (Detilleux et al., 1995), however, no significant changes in neutrophil numbers were observed in the current study.

Previous evaluation of SCS indicated that SCS in Herd 1 was lowest for animals of the high antibody response group, and greatest in animals of the low antibody response group at weeks 3,4,5 and 6 following parturition (Mallard et al., 1997; Ch. I). Conversely, SCS in Herd 2 was significantly lower for animals of the low antibody response group compared to animals of the high antibody response group (Ch. II). In the current study, SCS was negatively and significantly correlated with OVA stimulated lymphocyte proliferative responses and DTH response, indicating that sustained selection for low SCS could compromise aspects of CMI.

Depression of lymphocyte proliferation during the postpartum period has been demonstrated previously in humans (Weinberg, 1984), sheep (Burrels et al., 1978), and dairy cattle (Wells et al., 1977; Manak et al., 1982; Kashiwazaki et al., 1985; Ishikawa, 1987; and Kehrli et al., 1989a). Ishikawa (1987) demonstrated decreased blastogenic response in PBMC stimulated with Con A and pokeweed mitogen (PWM) from the third trimester of pregnancy, which reached a minimum at parturition. Saad et al. (1989) described a depressed Con A-, phytohemagglutinin (PHA)-, and PWM-stimulated lymphocyte proliferation that started only 1 week prior to parturition and was minimal one day before parturition. Saad et al. (1989) also evaluated milk mononuclear cell (MC) proliferative responses and, in contrast to PBMC, milk MC did not increase in proliferative response two weeks after lactation. Peripartum depression of lymphocyte proliferation was observed in unstimulated lymphocyte proliferative responses between weeks −3 and parturition (week 0), and a depression of response to Con A was also observed. The largest (P<0.05) depression of Con A stimulated lymphocyte proliferative responses at parturition were observed in animals with a high antibody response phenotype (Group 1). Again, this may indicate a negative association between high antibody response and certain indicators of CMI in dairy animals, which would need to be considered in the development of a selection index for high and low immune response.

Example 4
The Relationship Between Milk Production and Antibody Response to Ovalbumin (OVA) During the Peripartum Period Suboptimal innate and immune mechanisms of host resistance during the peripartum period may contribute to increased incidence of mastitis. To evaluate associations between antibody response to OVA and milk production variables during the peripartum period, 136 Holstein cows and heifers from 3 herds with known antibody response profiles, were evaluated for projected 305-day milk, protein, and fat yield. Using a mathematical index, animals were quantitatively classified based on their antibody responses to OVA into high (Group 1), average (Group 2) or low (Group 3) response groups. Group 3 had the highest (P<0.0001) milk yield (8448.6 kg) compared to Groups 1 (8191.2 kg) and 2 (8174.8 kg). Group 3 had the highest 305-day predicted protein (279.8 kg) and fat yield (343.1 kg) compared to Groups 1 (263.5 kg, 314.0 kg) and 2 (261.4 kg, 314.9 kg) respectively. However, in two out of the three herds investigated, Group 1 animals had no incidence of clinical mastitis compared to other antibody response groups. Although this suggests that animals with low antibody response produce more milk, fat and protein, and therefore more income, mastitis occurrence was observed to be highest for these animals in two out of three herds investigated. The development of animals that produce optimal levels of milk with reduced occurrence of mastitis may be possible through selective breeding for both production and enhanced immune response.

The objective of this example was to evaluate the effect of antibody response group on 305-day projected production traits (milk, fat, and protein) and relate production and immune response associations with disease occurrence.

Materials and Methods

Animals and Treatments

Phenotypic variation in immune responses of 136 Holstein cows and heifers from 2 research herds (n=32; n=67) and 1 commercial herd (n=37) were examined from week −3 relative to calving (week 0) to six weeks postpartum (week 6). Eighty-eight animals were multiparous cows and 48 were primiparous heifers. As described previously (Mallard et al., 1997; Ch. V), to stimulate antibody response during the peripartum period, animals received an intramuscular (im) injection of ovalbumin antigen (OVA, Type VII, Sigma Chemical Co., St. Louis, Mo.) and a mastitis endotoxemia preventive vaccine, an Rc mutant of *Escherichia coli* O111B4 (Rhône Mérieux *Escherichia coli* J5, Rhône Mérieux, Lenexa, Kans.) approximately 8 weeks (4 mg OVA) and 3 weeks (2 mg OVA) prior to predicted calving dates. At parturition (week 0), animals received a single immunization of the OVA dissolved in phosphate buffered saline (PBS−0.1 M, pH 7.4) (2 mg, im). Using a mathematical model described previously (Ch. II), animals were categorized based on their antibody response to OVA and grouped into high (Group 1), average (Group 2) and low (Group 3) antibody response phenotypes.

Production Variables

Projected 305 day milk, fat, and protein yields were obtained from the Ontario Dairy Herd Improvement Corporation (Ontario DHI). The last test day before the end of lactation was used to calculate projected 305-day milk, fat and protein and was based on at least 100 days in milk (DIM).

Statistical Methods

Type III least squares analysis of variance (ANOVA) and corrected means (least square means, LS Means) were generated using the General Linear Models (GLM) Procedure of the Statistical Analysis System (SAS; Helwig and Council, 1982) to evaluate the effects of herd, season-year, antibody response group, parity, week, and their interactions milk, fat, and protein yield (Table 6). Results were considered to be statistically significant if the p-value was <0.05 and trends were reported at the p-value <0.10.

Results

Effects of antibody response group on milk production variables

Milk yield

Parity and the interaction between antibody response group and parity contributed significantly (P<0.0001) and antibody response group tended (P<0.06) tended to contribute to variation in projected 305-day milk yield (Table 6). Group 3 animals had a significantly higher (P<0.0001) 305-day cumulative milk yield (8448.6 kg) compared to average (8174.8 kg) and high (8191.2 kg) antibody responding dairy animals (FIG. 12A).

Protein

Antibody response group, parity and the interaction between antibody response group and parity contributed significantly (P<0.0001) to variation in protein yield (Table 6). Group 3 animals had a significantly higher (P<0.0001) 305-day protein yield (279.8 kg) compared to average (261.3 kg) and high (263.5 kg) antibody responder animals (FIG. 12B).

Fat

Antibody response group, parity, and the interaction between antibody response group and parity significantly (P<0.0001) contributed to variation in 305-day fat yield (Table 6). Group 3 animals had a significantly higher (P<0.0001) 305-day cumulative fat yield (343.1 kg) compared to average (314.9 kg) and high (314.0 kg) antibody responding animals (FIG. 12C).

Discussion

The current study suggests that animals with the highest antibody response have lower milk, fat and protein yield. However, animals that have high antibody response in two out of the three herds evaluated were reported (Ch.II) to have the lowest occurrence of mastitis compared to animals with low antibody response. Given the positive correlation between the selection for increased milk production and the increased rate of clinical mastitis occurrence, one might hypothesize that superior production could be associated with unfavourable changes in host defense which could result in a higher occurrence of mastitis. The fact that animals of average and high antibody response (Groups 1 and 2) tended to produce less milk and milk solids per lactation than animals of the low antibody response group might indicate that selection based on antibody response to OVA is not economically feasible in the short term. At a price of $5.15/kg of fat and $8.39/kg protein (Ontario Milk Producer, October 1997), animals with low antibody response would earn an estimated revenue of Cdn$ 4114.49/ lactation (based on fat and protein component pricing only) followed by animals with high antibody response at $3827.87 per lactation ($286.62 less than Group 3 animals), and animals with average antibody response at $3814.04 per lactation ($300.45 less than low antibody response animals and $13.82 less than high response animals). In the long term however, it may be more beneficial to own animals with superior health traits that minimize disease-related costs (approximately $140–300/cow/lactation in Ontario; Zhang et al., 1993) and still produce milk at an optimal level of production quantity and quality. A previous U.S. study (Dunklee et al., 1994) determined that health costs were positively associated with higher production, however, health costs did not outweigh profit potential. Regardless of whether health costs do or do not have an impact on the production profit potential of dairy animals, reduced occurrence of mastitis will nonetheless be mutually beneficial to dairy producers, processors and consumers. Milk producers will benefit through a reduction in economic loss incurred by mastitis, processors manufacturing milk products will benefit from an enhancement in milk quality, and consumers concerned about animal welfare and food safety standards will appreciate knowing that antibiotic usage to treat mastitis has been reduced as a direct result of reduced mastitis occurrence. Further, as disclosed in this description, as certain immune response traits are heritable, it would be possible to select or breed cows with a desired level of immune response which should influence disease resistance. Milk quantity and quality may also be influenced by such breeding practice. It may be that cows with higher than average disease resistance and with high, but not maximum milk yields would result in maximum profits.

Example 5

Effects of Growth Hormone, Insulin-like Growth Factor-I, and Cortisol on Periparturient Antibody Response Profiles of Dairy Cattle The objectives of this example were to determine hormone and antibody response profiles from the prepartum period to peak lactation, and evaluate potential immunomodulatory effects of the classic endocrine hormones, growth hormone (GH), insulin-like growth factor-I (IGF-I) and cortisol. Specifically, 33 Holstein cows were immunized with ovalbumin (OVA) and *Escherichia coli* J5 at weeks –8 and –3 prior to parturition. At parturition (week 0), cows received an additional immunization of OVA. Blood was collected at weeks –8, –3, 0, 3 and 6 relative to parturition and various samples were used to determine plasma hormone concentration, serum immunoglobulin (Ig), and specific antibody response to OVA and *E. coli*. Colostrum and milk samples were also collected post-parturition to monitor local immunoglobulin and antibody responses. Results indicated that not all periparturient cows exhibited depressed immune response, and that antibody response to OVA could be used to partition cows into 3 groups recognizing animals with sustained measurable antibody response before and after parturition (Group 1), animals which responded poorly to immunization at parturition (Group 2), and animals which did not respond to immunizations at week –3 or parturition (Group 3). Cows with the highest antibody response to OVA (Group 1) also tended (P<0.10) to have the highest response to *E. coli* J5 at parturition and had the lowest incidence of disease, particularly mastitis. Antibody response to OVA measured in milk tended to be higher in Group 1 cows, particularly at week 0 (P<0.06) compared to cows of Group 3. IGF-I was higher (P<0.05) in cows of Group 1 than Group 3 at peak lactation (week 6).

To further understand the complex endocrine-immune interactions that occur around parturition and their impact on host resistance, we utilized the dairy cow as a large animal stress model of pregnancy, parturition, and lactation. To evaluate peripartum and peak 5 lactation immune response and hormone profiles, 33 cows were immunized with ovalbumin (OVA) and *Escherichia coli* (*E. coli*) J5. Blood samples were collected to measure antibody response, GH, IGF-I, and cortisol concentrations at dry-off (approximately 8 weeks prepartum) and weekly from week –3 to week 6 postpartum.

Materials and methods

Animals and Treatments

Antibody response and hormone profiles of 33 Holstein cows were examined from approximately eight weeks prepartum (week –8) based on predicted calving dates to six weeks postpartum (week 6). Twenty-six animals were multiparous cows and seven were primiparous heifers. To determine associations between periparturient immune responses and hormone profiles, animals received an intramuscular (im) injection of a mastitis endotoxemia preventive vaccine with the manufacturer's adjuvant (Rhône Mérieux *E. coli* J5, Rhône Mérieux, Lenexa, Kans.) along with the antigen, OVA (Type VII, Sigma Chemical Co., St. Louis Mo.), at weeks –8 (4 mg) and –3 (2 mg). At parturition (week 0), cows received an additional immunization of OVA without adjuvant dissolved in phosphate buffered saline (PBS–0.1 M, pH 7.4) (2 mg, im). OVA was chosen as an inert antigen to which these animals had not been previously exposed. *E. coli* J5 was used as an antigen previously recognized by most dairy cows and of more complex response, but of biological relevance. Animals were initially classified according to their serum antibody response curve kinetics to OVA as either high responders (Group 1) relative to cows that exhibited a lack of measurable response to immunization either postpartum (Group 2) or pre- and postpartum (Group 3) (FIG. 13A).

Blood and Milk Sampling Schedule

Peripheral blood was collected via tail venipuncture at week −8, and weekly from weeks −3 to 6 relative to parturition. Various samples were used to monitor plasma hormone concentrations (GH, IGF-I, cortisol), serum immunoglobulin $G_{1\&2}$, and specific antibody response to OVA and *E. coli* J5. Colostrum and milk samples were collected to monitor specific antibody to OVA and to monitor total $IgG_1$ (weeks 0, 3, 6) and $IgG_2$ (weeks 0 and 3). Colostrum was collected at the first milking following parturition. Milk samples were stripped from all quarters approximately 2–4 hr after morning milking. Colostrum and milk samples were stored frozen without preservative at −20° C. until time of whey separation and immunoglobulin quantification.

ELISA for OVA Antibody Detection In Serum and Whey

Serum was separated from coagulated peripheral blood by centrifugation and stored frozen (−20° C.) until time of assay. Milk samples were stored frozen (−20 C.) until time of assay when they were centrifuged twice (11,000 g, 15 min) to separate fat from whey. Antibody to OVA was detected by ELISA and quantified based on optical density measurements according to the procedure described by Burton, et al. 1993. Briefly, 96-well polystyrene plates (Fisher Scientific, Don Mills, Ont.) were coated with a $3.11 \times 10^{-5}$ M solution of OVA (OVA, Type VII, Sigma Chemical Co., St. Louis Mo.) dissolved in carbonate-bicarbonate coating buffer (pH 9.6). Plates were incubated (4° C., 48 h), then washed with PBS and 0.05% Tween 20 solution, (pH 7.4). Plates were blocked with a PBS–3% Tween 20 solution and incubated (room temperature; rt, 1 h). Plates were washed and diluted test sera (1/50 and 1/200) or milk whey (Neat, 1/10, 1/100 and 1/400) and controls were added using a quadrant system (Wright, 1987). Sera samples were added in duplicate, and whey samples were added in quadruplicate. Negative and positive controls included a pooled sample of pre-immunization sera and a pooled sample of sera from cows 14 days post secondary immunization respectively. Plates were incubated at rt for 2 h. Subsequently, alkaline phosphatase conjugate rabbit anti-bovine IgG (whole molecule) (Sigma Chemical Co., St. Louis, Mo.) was dissolved in wash buffer, added to the plates and incubated (rt, 2 h). P-Nitrophenyl Phosphate Disodium tablets (pNPP) (Sigma, St. Louis, Mo.) were dissolved in a 10% diethanolamine substrate buffer, (pH 9.8). Plates were washed with wash buffer, pNPP was added to the plates and was then incubated at rt for 30 minutes (min). Plates were read on a EL311 automatic ELISA plate reader (BIO-TEK Instruments, Highland Park, Vt.) and the optical density (OD) was recorded at 405 and 630 nanometres (nm) when the positive control reached $OD \geq 0.999$. The mean of the number of replicates added to each plate was corrected to an OD=1.0 by multiplying by the inverse of the mean of the positive controls. Corrected means of each dilution were then added together to give an additive OD value, indicative of antibody response.

ELISA for *E. coli* J5 Antibody Detection In Serum

According to the method described by Rhône-Mérieux Animal Health (Lenexa, Kans.; 1994 personal communication), heat-killed *E. coli* strain J5 (ATCC, Rockville, Md.) was coated at a concentration of $6.25 \times 10^7$ colony forming units per mL onto Dynatech Immulon II polystyrene 96-well flat bottom plates overnight at 4° C. After washing with wash buffer (PBS plus 0.05% Tween 20), 1% gelatin was added to block non-specific binding and plates were incubated (rt, 1 h). Plates were washed and four replicates of test serum (dilutions of 1/1000, 1/1500, 1/2000 and 1/2500) were added using a modified quadrant system. PBS–0.05% Tween 20 was used as a blank and fetal calf serum (FCS, Bockneck Laboratories, Can Sera, Rexdale, Ont.) was used as a negative control. Negative and positive controls prepared from pooled pre- and post immunization sera were plated respectively. Test sera were incubated (rt, 2 h), and plates were washed with PBS–0.05% Tween 20. Horseradish peroxidase conjugate goat anti-bovine IgG whole molecule in PBS (1/4000; The Binding Site, Birmingham, UK) was added and the plates were incubated (rt, 1 h). After washing, the substrate, 2,2'-azino-di-(3-ethyl-benzthiazoline sulphonate-6) (ABTS; Boehringer Mannheim, Laval, Que.) was added and plates were incubated (rt, 30 min). Plates were then read on an EL311 automatic ELISA plate reader (BIO-TEK Instruments, Highland Park, Vt.) and OD recorded at 405 nm and 490 nm. The mean OD of the four sample replicates were corrected to an OD=1.0. Based on the immunization protocol and phenotypic observation of antibody response curve kinetics of all dilutions tested, the 1/1000 dilution consistently allowed for differentiation between positive and negative controls, exhibiting minimal prozone effect and therefore was the dilution of choice for comparison between animals.

Radial Immunodiffusion Assay

Radial immunodiffusion was used according to a method previously described (Mallard et al. 1992) to determine the concentrations of $IgG_{1\&2}$ in serum and whey from colostrum and milk. Whey from weeks 0 and 3 were tested for the $IgG_{1\&2}$ subclasses. At week 6 however, $IgG_1$ only was tested in whey since very low concentrations of $IgG_2$ exist in normal milk (Butler, 1980).

Disease Occurrence

Occurrence of infectious and metabolic diseases were recorded throughout the study period since connections within the endocrine-immune axis may conceivably affect both. Disease events were classified by number as follows: none =0, mastitis =1, ketosis =2, and other (diseases occurring at lower frequency in this study; for example, milk fever and pneumonia)=3.

Somatic Cell Count

Milk (AM/PM composite sample) was collected weekly during milking to determine somatic cell count (SCC). Only the SCC counts which coincided with the day of blood sample collection for each week are reported. SCC, an indicator of subclinical mammary gland infection, was transformed to somatic cell score (SCS) for analysis. SCS is the natural logarithm of SCC in cells/$\mu$L and is calculated as follows (Shook, 1993):

$$SCS=\log_e(SCC/100) \div \log_e(2)+3$$

Hormone Assays

Peripheral blood samples collected for hormone assay were immediately put on ice. Samples were centrifuged at 4° C. and the plasma was removed. Plasma from each cow was individually aliquoted into multiple 1 mL containers and stored frozen at −20° C. until time of each hormone assay.

Cortisol

Plasma cortisol concentration ($\mu$g/dL) was determined using a commercially available Gamma Coat Cortisol $^{125}$I, RIA kit (INCSTAR Corporation, Stillwater, Minn.). The assay sensitivity was 0.21 $\mu$g/dL and the inter- and intra-assay CV were less than 10%.

IGF-I and GH

Radioimmunoassay (RIA), as described previously by Elsasser et al. (1989), was used to determine the IGF-I concentration (ng/mL) of samples. The IGF-I used for tracer and standards was recombinant threonine-59-substituted human IGF-I (Amgen; Thousand Oaks, Calif.). Based on duplicate samples, all performed on the same day, the intra-assay CV was less than 10%. GH concentration (ng/mL) was quantified using RIA (Elsasser et al., 1988).

Statistical Methods

Least squares analysis of variance (ANOVA) and corrected means (least square means, LS Means) were generated using the General Linear Models (GLM) Procedure of the Statistical Analysis System (SAS; Helwig and Council, 1979). The statistical models used in this study included fixed effects of antibody response groups (1,2,3), cow nested within antibody response group, and week relative to parturition (weeks −3, 0, 3, and 6). In preliminary analysis, the effect of parity was not significant and was therefore removed from all subsequent models. A model was constructed for the following dependent variables: antibody response to OVA in sera and whey, antibody response to $E.\ coli$ J5 in sera, and the concentration of $IgG_{1\&2}$ in serum and whey. Sources of variation included in the model for each dependent variable are summarized in Table 7. Hormone concentrations (GH, IGF-I, cortisol) were included as covariates in all models. Data that did not show a normal distribution as indicated by the univariate procedure of SAS, were transformed to natural logarithms. Pearson product moment correlation coefficients between immune response variables and hormone concentrations were generated using the correlations procedure of SAS (Proc CORR). Results were considered to be statistically significant if the P-value was $\leq 0.05$ and trends were reported at the P-value $\leq 0.10$.

Results

Antibody Response to OVA Serum

Serum antibody response to OVA varied significantly over the peripartum period and individuals could be readily classified into three immune response groups: high responders (Group 1, n=12; 6 heifers, 6 cows) relative to animals which exhibited a lack of measurable response to immunization either postpartum (Group 2, n=12 cows) or pre- and postpartum (Group 3, n=9; 8 cows, 1 heifer). Approximately ⅓ (Group 1) of the animals showed consistent, above average serum antibody response to OVA following immunization at weeks −8, −3, and 0 relative to parturition. The remaining animals had either an average amount of antibody, or had responses lower than the population mean and did not respond following immunization at week −3 or 0 relative to parturition (FIG. 13A). All cows including those of Group 3 exhibited responses greater than background (week −8) at week −3 and therefore were considered low responders rather than non-responders. ANOVA indicated that the statistical model accounted for 94.19% of the total variation in serum antibody response to OVA over the peripartum period, and that the effects of cow ($P \leq 0.0001$), antibody response group ($P \leq 0.005$), and the interaction between antibody response group and week ($P \leq 0.0001$), contributed significantly to the variation in antibody response to OVA (Table 7). Growth hormone (GH) exhibited some tendency to be positively associated with antibody response to OVA ($P \leq 0.15$). Animals in Group 1, with the highest antibody response to OVA, consistently had the highest GH concentrations in plasma at each sample week in comparison to animals in Groups 2 and 3 (FIG. 14A). Although these differences as determined in the ANOVA may not have been statistically significant (Table 7), correlation analysis indicated a significant and positive relationship ($r^2=0.29$, $P \leq 0.001$) between antibody response to OVA and GH, regardless of week or antibody response group (Table 8). This would suggest that there is biological significance to the consistently higher GH concentrations in the high immune response group (J. L. Burton 1991, PhD Thesis, University of Guelph). LS Means of IGF-I and cortisol concentrations in plasma (FIGS. 14B,C) were not significantly different between immune response groups, except at week 6 when Group 1 cows had higher concentrations of IGF-I ($P \leq 0.05$) compared to cows in Group 3 (FIG. 14B). Correlation analysis of antibody response to OVA indicated relationships with IGF-I ($r^2=-0.19$, $P \leq 0.04$) and cortisol ($r^2=0.17$, $P \leq 0.06$) (Table 8).

Whey

ANOVA indicated that cow ($P \leq 0.006$), antibody response group ($P \leq 0.003$) and the interaction between IGF-I concentration and week ($P \leq 0.005$) contributed significantly to the variation in whey antibody response (Table 7). There was a tendency for week relative to parturition ($P \leq 0.06$) to associate with antibody response to OVA in whey. Corrected population least square means (LS Means) of antibody response to OVA in whey declined significantly following parturition, such that at week 0 the OD value was 1.68±0.17 compared to 0.85±0.17 ($P \leq 0.004$) at week 3 and 0.50±0.20 ($P \leq 0.0001$) at week 6 (FIG. 13B). At parturition, there was a tendency ($P \leq 0.06$) for antibody response to OVA in whey to differ between Groups 1 (1.96±0.26) and 3 (1.33±0.23). Comparable to the antibody response to OVA in serum, correlation analysis indicated a significant relationship between OVA antibody response in whey with GH ($r^2=0.31$, $P \leq 0.0005$) and IGF-I ($r^2=-0.22$, $P \leq 0.01$) (Table 8).

Antibody Response to $E.\ coli$ J5

Only the effect of cow ($P \leq 0.0002$) contributed significantly to the variation in antibody response to $E.\ coli$ J5. Pre-immunization sera (week −8) indicated that these cows had minimal background OD values of measurable $E.\ coli$ J5 specific antibody prior to vaccination (population mean±SEM=0.314±0.11; n=33) compared to post-vaccination natural antilogarithm OD values at week −3 (0.663) and week 0 (0.830). Antibody response to $E.\ coli$ when grouped by antibody response group (1, 2, or 3), indicated that only at parturition (week 0) did Group 1 animals tend ($P \leq 0.10$) to have a higher concentration of $E.\ coli$ specific antibody (OD value=1.053) than Group 3 animals (OD value=0.702). Correlation analysis indicated that GH was significantly correlated with antibody response to J5 $E.\ coli$ ($r^2=0.18$, $P \leq 0.04$) (Table 8). Antibody response to $E.\ coli$ J5 was positively correlated with antibody response to OVA ($r^2=0.59$, $P \leq 0.0001$).

$IgG_1$ & $IgG_2$ in serum colostrum, colostrum and milk

Antibody response group significantly contributed to the variation of serum $IgG_2$ ($P \leq 0.002$) only. There was a tendency for the interaction between IGF-I and week relative to parturition to account for variation in total whey $IgG_1$ concentration ($P \leq 0.07$). The model constructed for whey $IgG_2$ was unable to explain the variation in this response. Correlation analysis indicated a significant, negative relationship between GH and $IgG_1$ in serum ($r^2=-0.26$; $P \leq 0.01$). Conversely, IGF-I tended to correlate positively with total $IgG_1$ in serum ($r^2=0.19$, $P \leq 0.07$). Growth hormone ($r^2=0.26$, $P \leq 0.03$) and IGF-I ($r^2=-0.20$, $P \leq 0.10$) correlations with $IgG_1$ in whey were reversed from that in serum.

Disease Occurrence

Records of disease events indicated that 54.5% of the 33 animals evaluated were considered healthy during this study. Of the diseased animals, 7 cows had mastitis events (21.21%), 7 had ketosis events (21.21%) and 3 cows had other disease events (9.09%) while on this study. Group 1 animals which showed a consistent above average antibody response to OVA, had the lowest percent occurrence of disease (FIG. 15) and actually had no occurrence of clinical mastitis.

Somatic Cell Score (SCS)

At parturition, LS Means of SCS were significantly lower ($P \leq 0.05$) for Group 2 cows (SCS=3.2) compared to Group 1 (SCS=4.36) and Group 3 (SCS=4.98) cows. At weeks 2,3,4, and 6 after parturition, all groups differed significantly from one another, and, Group 1 cows consistently had the lowest SCS while Group 3 cows consistently had the highest SCS.

Hormones

At parturition, least square mean (LS Mean) concentrations of GH (FIG. 14A) and cortisol (FIG. 14C) were at a maximum while IGF-I (FIG. 14B) was at a minimum. After parturition, GH concentrations decreased ($P \leq 0.05$) until week 6. Cortisol concentrations also decreased ($P \leq 0.05$) post-parturition and then increased slightly after week 3. In contrast, IGF-I concentrations decreased ($P \leq 0.05$) at parturition and then continued to increase ($P \leq 0.05$) toward peak lactation.

The present study is the first to simultaneously evaluate specific antibody responses and hormone profiles during the peripartum period and has revealed some associations between IGF-1 and antibody response, however, no actual cause and effect relationship can be established from this study. In addition, an elevation of plasma IGF-I during the latter stages of pregnancy followed by a dramatic decline around parturition with a steady increase in concentrations following parturition was demonstrated. Some of these observations have been confirmed in the literature; for instance, Vega et al. (1991) attributed changes in IGF-1 and GH to the decrease in metabolic demands associated with the cessation of milk production, during late gestation, followed by an increase in metabolic demand associated with the onset of lactation at parturition. As well, the demand of the mammary gland may alter the transport of IGF-I by sequestering it from the blood. Lactogenic hormones, such as prolactin and cortisol, may also prevent the synthesis of IGF-I and IGF-I binding proteins (Vega et al., 1991).

As previously reported (Hoshino et al., 1991), circulating concentrations of GH increased around parturition, concurrent with early milk production, and decreased as lactation progressed. The inverse relationship between peripartum IGF-I and GH is noteworthy in that IGF-I production is normally dependent on GH as blood concentrations influence liver production of IGF-I (Burton et al., 1992). However, due to the peripartum uncoupling between these two hormones, it may be possible to evaluate the influence of each hormone separately on both the innate and humoral aspects of the immune system.

Although the interaction of GH, and to a lesser extent IGF-I, with the immune system has been widely reported in a variety of species including dogs, humans and mice, direct effects of GH on lymphoid cells have not been unequivocally demonstrated. For example, GH deficient patients often are not found to be immuno-compromised (Fornari et al., 1994). Furthermore, various studies have demonstrated that the immune systems of GH deficient children treated with GH can be normal, suppressed or even enhanced (Gupta et al., 1983; Kelley, 1990; Petersen et al., 1990). It is also suggested that some effects of GH on the immune system are a result of IGF-I (Burton et al., 1992; Badolato et al., 1994). In general these studies indicate that the precise relationships between these hormones and immune responsiveness will be challenging to untangle. In the present study, GH concentration was positively, and IGF-I negatively correlated with antibody response. Animals in Group 1 with the highest antibody response to OVA, tended to have the highest GH concentrations. Although some of the results were not necessarily statistically significant, correlation analysis indicated a positive relationship between antibody and GH. For this reason the present invention may be used to select high immune responders with naturally enhanced levels of growth hormone. Thus the benefits of higher levels of growth hormone in animals could be obtained, while avoiding the side effects associated with artificially enhancement of growth hormone levels such as those associated with the use of synthetic growth hormones. For the most part, IGF-I concentrations were not different among immune response groups, except at week 6 when cows of Group 1 had significantly higher concentrations than Group 3 cows. Thus, the methods of the present invention could be used to identify or select for animals with high post- peripartim IGF-1 levels. These results are consistent with the work of Yoshida et al., (1992) which demonstrated that GH stimulates B cell growth and Ig synthesis by B cells and B cell lines. Growth hormone has been reported to alter antibody synthesis in response to T-dependent antigens, as well as increase activity of T lymphocytes and natural killer (NK) cells (Geffner et al., 1990; Schurmann et al., 1995). Badolato et al., (1994) found that B cells displayed relatively high numbers of GH receptors, whereas T and NK cells showed much lower numbers of receptors. In addition, increased GH concentrations can enhance otherwise suppressed antibody response due to stress released glucocorticoids (Franco et al., 1990). Again, it has been suggested that the effects of GH may be mediated through IGF-I, a lymphocyte growth factor (Franco et al., 1990), but whether this is true during the peripartum period when these hormones become uncoupled seems unlikely.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

FULL CITATIONS FOR REFERENCES REFERRED TO IN THE SPECIFICATION

A. Arestrup, F. M., Jensen, N. E., and Østergard, H., 1995. Analysis of associations between major histocompatibility complex (BoLA) class I haplotypes and subclinical mastitis of dairy cows. J. Dairy Sci., 78:1684–1692.

Arthur, R. P., and Mason, D., 1986. T cells that help B cell responses to soluble antigen are distinguishable from those producing interleukin 2 on mitogenic or allogenic stimulation. J. Exp. Med., 163:774–786.

Bachen, E. A., Manuck, S. B., Marsland, A. L., Cohen, S., Malkoff, S. B., Muldoon, M. F., and Rabin, B. S., 1992. Lymphocyte subset and cellular immune responses to a brief experimental stressor. Psychosom. Med., 54:673–679.

Badolato, R., Bond, H. M., Valerio, G., Petrella, A., Morrone, G., Waters, M. J., Venuta, S., and Tenore, A., 1994.

Differential expression of surface membrane growth hormone receptor on human peripheral blood lymphocytes detected by dual fluorochrome flow cytometry. J. Clin. Endocrinol. Metab., 79:984–990.

Banos, G., and Shook, G. E., 1990. Genotype by environment interaction and genetic correlations among parities for somatic cell count and milk yield. J. Dairy Sci., 73:2563–2573.

Bauman, D. E., Eppard, P. J., DeGeeter, M. J. and Lanza, G. M., 1985. Responses of high-producing dairy cows to long-term treatment with pituitary somatotropin and recombinant somatotropin. J. Dairy Sci., 68:1352–1362.

Biozzi, G., Stiffel, C., Mouton, D., Bouthillier, Y., and Deereusefound, C., 1968. A kinetic study of antibody producing cells in the spleen of mice immunized intravenously with sheep erythrocytes. Immunol., 14:7–20.

Biozzi, G., Stiffel, C., Mouton, D., Bouthillier, Y., and Decreusefond, C., 1972. Cytodynamics of the immune response in two lines of mice genetically selected for high and low antibody synthesis. J. Exp. Med., 135:1071–1094.

Biozzi G., Mouton, D., Sant'Anna, O. A., Passos, H. C., Gennari, M., Bouthillier, Y. Ibanez, O. M., Stiffer, C., and Siquerira, M., 1979. Genetics of immunoresponsiveness to natural antigens in the mouse. Curr. Top. Microbiol. Immunol., 85:31–98.

Blalock, J. E., 1994. The syntax of immune-neuroendocrine communication. Immunol.Today, 15:504–511.

Boettcher, P. J., Hansen, L. B., Van Raden, P. M. and Ernst, C. A., 1992. Genetic evaluation of Holstein bulls for somatic cells in milk of daughters. J. Dairy Sci., 75:1127–1137.

Bruecker, K. A. and Schwartz, L. W., 1982. Bovine peripheral blood polymorphnuclear neutrophil chemotactic response to Pastuerella hemolytica or zymosan-activated serum. Am. J. Vet. Res., 43:1879–1881.

Burrells, C., Wells, P. W., and Sutherland, A. D., 1978. Reactivity of ovine lymphocytes to phytohemagglutinin and pokeweed mitogen during pregnancy and in the immediate post-parturient period. Clin. Exp. Immunol., 55:410–415.

Burton, J. L., Mallard, B. A., and Mowat, D. N., 1993. Effects of supplemental chromium on immune resposes of periparturient and early lactation dairy cows. J. Anim. Sci., 71(6):1532–1539.

Burton, J. L., Burnside, E. B., Kennedy, B. W., Wilkie, B. N., and Burton, J. H., 1989a. Antibody responses to human erythrocytes and ovalbumin as marker traits of disease resistance in dairy calves. J. Dairy Sci., 72:1252–1265.

Burton, J. L., Kennedy, B. W., Burnside, E. B., Wilkie, B. N., and Burton, J. H., 1989b. Dinitrochlorobenzene contact hypersensitivity as a marker trait for selection to improve disease resistance in calves. J. Dairy Sci., 72:2351–2361.

Burton, J. L., McBride, B. W., Kennedy, B. W., Burton, J. H., Elsasser, T. H. and Woodward, B., 1991. Influence of exogenous bovine somatotropin on the responsiveness of peripheral blood lymphocyte to mitogen. J. Dairy Sci., 74:916–928.

Burton, J. L., McBride, B. W., Kennedy, B. W., Burton, J. H., Elsasser, T. H., and Woodward, B., 1992. Contact sensitivity and systemic antibody responses in dairy cows treated with recombinant somatotropin. J. Dairy Sci., 75:747–755.

Burton, J. L., Nonnecke, B. J., Elsasser, T. H., Mallard, B. A., Yang, W. Z., and Mowat, D. N., 1995. Immunomodulatory activity of blood serum from chromium-supplemented periparturient dairy cows. Vet. Immunol. Immunopath., 49:29–38.

Burvenich, C., Paape, M. J., Hill, A. W., Guidry, A. J., Miller, R. H., Heyneman, R., Kremer, W. D. J. and Brand A., 1994. Role of the neutrophil leukocyte in the local and systemic reactions during experimentally induced *E.coli* mastitis in cows immediately after calving. Vet. Quart., 16:45–50.

Butler, J. E., 1980. A concept of humoral immunity among ruminants and an approach to its investigations. The Ruminant Immune System: Proc. Int. Symp. Rum.Imm. Sys., Plymouth, N.H., pp. 3–55.

Butler, W. R., Everett, R. W., and Coppock, C. E., 1981. The relationships between energy balance, milk production, and ovulations in postpartum Holstein cows. J. Anim. Sci., 53:742–748.

Byfield, P. E., and Howard, J. G., 1972. Equivalent graft-versus-host reactivity of spleen cells from two lines of mice genetically selected for high and low humoral antibody formation. Transplant. 14:133–134.

Cai, T., Weston, P. G., Lund, L. A., Brodie, B., McKenna, D. J., Wagner, W. C., 1994. Association between neutrophil functions and periparturient disorders in cows. Am. J. Vet. Res., 55:934–943.

Caroll, E. J., Mueller, R. and Panico, L., 1982. Chemotactic factors for bovine leukocytes. Am. J. Vet. Res., 43:1661–1664.

Caroll, E. J., 1983. Immunological aspects of coliform mastitis. Vet. Res. Comm. 7:247.

Chang, X., Mallard, B. A., and Mowat, D. N., 1994. Proliferation of peripheral blood lymphocytes of feeder calves in response to chromium. Nut. Res., 14:851–864.

Clarke, A. G. and Kendall, M. D., 1994. The thymus in pregnancy: the interplay of neural, endocrine and immune influences. Immunol. Today, 15(11): 545–551.

Colditz, I. G., and Maas, P. J. C., 1987. The inflammatory activity of activated complement in ovine and bovine mammary glands. Immunol. Cell Biol., 65:433–436.

Craven, N., 1986. Chemotactic factors for bovine neutrophil in relation to mastitis. Comp. Immunol. Microbiol. Inf. Dis., 9:29–36.

Craven, N., and Williams, M. R., 1985. Defences of the bovine mammary gland against infection and prospects for their enhancement. Vet. Immunol. Immunopath. 10:71.

Cullor, J., 1991. The *Escherichia coli* J5 vaccine: Investigating a new tool to combat coliform mastitis. Vet. Med., 836–844.

Daley, M. J., Oldham, E. R., Williams, T. J., and Coyle, P. A., 1991. Quantitative and qualitative properties of host polymorphnuclear cells during experimentally induced *Staphylococcus aureus* mastitis in cows. Am. J. Vet. Res., 52(3):474–479.

Davis, R. S., Gluckman, P. D., Hart, I. C., and Henderson, H. V., 1987. Effects of injecting growth hormone or throixine on milk production and blood plasma concentrations of insulin-like growth factors I and II in dairy cows. J. Endocrinol., 114:17–24.

Dehoff, M. H., Elgin, R. G., Collier, R. J., and Clemmons, D. R., 1988. Both type I an II insulin-like growth factor receptory binding increase during lactogenesis in bovine mammary tissue. Endocrinol., 122:2412–2417.

Dekkers, J. C. M. and Burnside, E. B., 1994. Sire selection for udder health. Ont. Milk Prod. September 1994, pp. 31–34.

Dekkers, J. C. M., TenHag, J. H., and Weersink, A., 1996. Economic aspects of persistency of lactation. 1996 Dairy Research Report, Ontario Ministry of Agriculture, Food and Rural Affairs, Publ. No. 0396, pp. 81–85.

Dekkers, J. C. M., Kolstad, B., Jairath, L. K., and Liu, Z., 1996. A new economic index for selection of sires. 1996 Dairy Research Report, Ontario Ministry of Agriculture, Food and Rural Affairs, Publ. No. 0396, pp15–25.

Dekkers, J. C. M., Boettcher, P. J., and Mallard, B. A., 1998., Genetic improvement of udder health. 6th World Congr. Genet. Appl. Livest. Prod., Australia.

Derijk, R. and Stemberg, E. M., 1994. Corticosteroid action and neuroendocrine-immune interactions. Ann. N. Y. Acad. Sci., 746:33–44.

Detilleux, J. C., Koehler, K. J., Freeman, A. E., Kehrili, Jr., M. E., and Kelley, D. H., 1994. Immunological parameters of periparturient Holstein cattle: genetic variation. J. Dairy Sci., 77:2640–2650.

Detilleux, J. C., Kehrli, Jr., M. E., Freeman, A. E., Whetston, C. A., and Kelley, D. H., 1995a. Two retroviral infections of periparturient Holstein cattle: A phenotypic and genetic study. J. Dairy Sci., 78:2294–2298.

Detilleux, J. C., Kehrli, Jr., M. E., Stabel, J. R., Freeman, A. E., and Kelley, D. H., 1995b. Study of immunological dysfunction in periparturient Holstein cattle selected for high and average milk production. Vet. Immunol. Immunopath., 44:251–267.

Detilleux, J. C., Kehrli, Jr., M. E., Stabel, J. R., Freeman, A. E., Fox, L., and Kelley, D. H. 1995c. Mastitis of periparturient Holstein cattle: A phenotypic and genetic study. J. Dairy Sci., 78:2285–2293.

Dietz, A. B., Cohen, N. D., and Timms, L., 1997a. Bovine lymphocyte antigen cl. II alleles as risk factors for high somatic cell counts in milk of lactating dairy cows. J. Dairy Sci., 80:406–412.

Dietz, A. B., Detilleux, J. C., Freeman, A. E., Kelley, D. H., Stabel, J. R. and Kehrli Jr., M. E., 1997b. Genetic association of bovine lymphocyte antigen DRB3 alleles with immunological traits of Holstein cattle. J. Dairy Sci., 80(2):400–405.

Dubey, D. P., 1992. Histocompabitiblity and transplantation immunology. Manual of laboratory immunology. ASM Press. Editors: N. R. Rose, E. C. DeMacario, J. L. Fahey, H. Friedman, G. M. Penn., pp. 870–871.

Dunklee, T. S., Freeman, A. E., and Kell, D. H., 1994. Comparison of Holsteins selected for high and average milk production. 2. Health and reproductive response to selection for milk. J. Dairy Sci., 77:3683–3690.

Dürr, J. W., Monardes, H. B. and Turner, J. D., 1996. Correlations of neutrophil phagocytosis for proven bulls with traits of economic importance of their daughters. J. Dairy Sci., 79:133–139.

Durum, S. K., Schmidt, J., and Oppenheim, J. J., 1985. Interleukin-1: an immunological perspective. Ann. Rev. Immunol., 3:263–287.

Eichmann, K., Braun, D. G., and Krause, R. M., 1971. Influence of genetic factors on the magnitude and the heterogeneity of the immune response in the rabbit. J. Exp. Med., 134:48–65.

Elsasser, T. H., Rumsey T. S., Hammond, A. C., and Fayer, R., 1988. Influence of parisitism on plasma concentrations of growth hormone, somatomedin-C and somatomedin-binding proteins in calves. J. Endocrinol., 116:191–200.

Elsasser, T. H., Rumsey, T. S., and Hammond, A. C., 1989. Influence of diet on basal and growth hormone-stimulated plasma concentrations of IGF-I in beef cattle. J. Anim. Sci., 67:128–141.

Emmanuelson, U., Danell, B., and Phillipsson, J., 1988. Genetic parameters for clinical mastitis, somatic cell counts, and milk production estimated by multiple-trait restricted maximum likelihood. J. Dairy Sci., 71:467–475.

Envoldsen, C., Hindhede, J., and Kristensen, T., 1996. Dairy herd management types assessed from indicators of health, reproduction, replacement, and milk production. J. Dairy Sci., 79:1221–1236.

Fomari, M. C., Scolnik, M. P., Palacios, M. F., Intebi, A. D., and Diez, R. A., 1994. Growth hormone inhibits normal B cell differentiation and neutrophils' chemotaxis in vitro. Int. J. Immunopharmac., 16(8):667–673.

Franco, P., Marelli, O., Lattuda, D., Locatelli, V., Cocchi, D., and Muller, E. E., 1990. Influence of growth hormone on the immunosuppressive effect of prednisolone in mice. Acta Endocrinologica, 123:339–344.

Franklin, S. T., Young, J. W., and Nonnecke, B. J., 1991. Effects of ketones, acetate, butyrate, and glucose on lymphocyte proliferation., J. Dairy Sci., 74:2507–2514.

Fries, R., Hediger, R., and Stranzinger, G., 1986. Tentative chromosomal localization of the bovine majorhistocompatibility complex by in situ hybridization. Anim. Genet., 17:287–294.

Gambel, P. I., and Ferguson, F. G., 1982. An in vitro and in vivo analysis of murine immunocompetence during pregnancy and lactation. J. Reprod. Immunol., 4:107–119.

Gavora, J. S., Spencer, J. L., Gowe, S., and Harris, D. L., 1980. Lymphoid leukosis virus infection: Effects on production, mortality, and consequences for selection for high egg production. Poultry Sci., 59:2165–2178.

Gavora, J. S., and Spencer, J. L., 1983. Breeding for immune responsiveness and disease resistance. Anim. Blood Groups Biochem. Genet., 14:159–180.

Gawazdauskas, F. C., Keys, J. E., and McGilliard, M. L., 1986. Adrenal response during periparturient period to adrenocorticotropin in dairy cattle fed corn silage and grass legume silage. J. Dairy Sci., 69:2134–2139.

Geffner, M. E., Bersch, N., Lippe, B. M., Rosenfeld, R. G., Hintz, R. L., and Golde, D. W., 1990. Growth hormone mediates the growth of T-lymphoblast cell lines via locally generated insulin-like growth factor-I. J. Clin. Endocrinol. Metab., 71:464–469.

Gilbert, R. O., Gröhn, Y. T., Miller, P. M., and Hoffman, D. J., 1993a. Effect of parity on periparturient neutrophil function in dairy cows. Vet. Immunol. Immunopath., 36:75–82.

Gilbert, R. O., Gröhn, Y. T., Guard, C. L., Surman, V., Neilsen, N., and Slauson, D. O., 1993b. Impaired post partum neutrophil function in cows which retain fetal membranes. Res. Vet. Sci., 55:15–19.

Gilbert, F. B., Poutrel, B. and Sutra, L., 1994. Immunogenecity in cows of *Staphylococcus aureus* type 5 capsular polysaccharide-ovalbumin conjugate. Vaccine, 12(4):369–374.

Gillis, S., Ferris, M., Ou., W., and Smith, K., 1978. T cell growth factor: parameters for production and a quantitiative microassay for activity. J. Immunol., 120:2027–2032.

Giraudo, J. A., Calzolari, A., Rampone, H., Rampone, A., Giraudo, A. T., Bogni, C., Larriestra, A., and Nagel, R., 1997. Field trials of a vaccine against bovine mastitis. 1. Evaluation in heifers. J. Dairy Sci., 80:845–853.

Glass, E. J., and Spooner, R. L., 1990. Generation and characterization of bovine antigen-specific T cell lines. J. Immunol. Methods, 128:267–275.

Glass, E. J., Oliver, R. A., and Spooner, R. L., 1990. Variation in T cell responses to ovalbumin in cattle: evidence for Ir gene control. Anim. Genet., 21:15–28.

Goff, J. P., and Horst, R. L., 1997. Phsiological changes at parturition and their relationship to metabolic disorders. J. Dairy Sci., 80:1260–1268.

Goff, J. P., and Stabel, J. R., 1990. Decreased plasma retinol, α-tocopherol, and zinc concentration during the periparturient period: effect of milk fever. J. Dairy Sci., 73(11):3195–3199.

Gonzalez, R. L., Cullor, J. S., Jasper, J. E., Farver, T. B., Bushnell, R. B. and Oliver, M. N., 1989. Prevention of clinical coliform mastitis in dairy cows by a mutant *Escherichia coli* vaccine. Can. J. Vet. Res., 53(3):301–305.

Gray, G. D., Knight, K. A., Nelson, R. D., and Herron, M. J., 1982. Chemotactic requirements of bovine leukocytes. Am. J. Vet. Res., 43: 757–759.

Griffin, J. F. T., 1989. Stress and Immunity: a Unifying Concept. Vet. Immunol. Immunopathol., 20: 263–312.

Gröhn, Y. T., Eicker, S. W., and Hertl, J. A. 1995. The association between previous 305-day milk yield and disease in New York state dairy cows. J. Dairy Sci., 78:1693–1702.

Guidry, A. J., Paape, M. J., and Pearson, R. E., 1976. Effects of parturition and lactation on blood and milk cell concentrations, corticosteroids, and neutrophil phagocytosis of the cow. Am. J. Vet. Res., 37:1195–1200.

Gupta, S., Fikrig, S. M., and Noval, M. S., 1983. Immunological studies in patients isolated with growth hormone deficiency. Clin. Exp. Immunol., 54:87–90.

Harmon, R. J., Schanbacker, F. L., Ferguson, L. C., and Smith, K. L., 1975. Concentration of lactoferrin in milk of normal lactating cows and changes occurring during mastitis. Am. J. Vet. Res., 36:1001–1007.

Harmon, R. J., 1994. Physiology of mastitis and factors affecting somatic cell counts. 1994. J. Dairy Sci., 77: 2103–2112.

Harp, J. A., Kehrli, M. E., Hurley, D. J., Wilson, R. A., and Boone, T. C., 1991. Number and percent of T lymphocytes in bovine peripheral blood during the peripartum period. Vet. Immunol. Immunopath., 28:29–35.

Helwig, T. T. and Council, K. A., 1982. SAS User's Guide. SAS Institute, Raleigh, N.C.

Hein, W. R. and Mackay, C. R., 1991. Prominence of γδ T cells in the ruminant immune system. Immunol. Today, 12:30–34.

Hessing, M. J. C., Coenen, G. J., Vaiman, M., and Renard, C., 1995. Individual differences in cell-mediated and humoral immunity in pigs. Vet Immunol. Immunopath., 45:97–113.

Heyneman, R., Burvenich, C., and Vercauteren, R., 1990. Interaction between the respiratory burst activity of neutrophils, leukocytes and experimentally induced *Escherichia coli* mastitis in cows. J. Dairy Sci., 73:985–994.

Hill, A. W., Heneghan, D. J. S., and Williams, M. R., 1983. The opsonic activity of bovine milk whey for the phagocytosis and killing by neutrophils of encapsulated and non-encapsulated *Escherichia coli*. Vet. Microbiol., 8:293–300.

Hoffman-Goetz, L. and Pedersen, B. K., 1994. Exercise and the immune system: a model of the stress response? Immunol. Today, 15(8):382–387.

Hoshino, S., Wakita, M., Kobayashi, Y., Sakauchi, R., Nishiguchi, Y., Ozawa, A., Hodate, K., Hamaguchi, I. and Yotani, Y., 1991. Variations in serum level of insulin-like growth factor-1, growth hormone, and thyroid hormones during lactation in dairy cows. Comp. Biochem. Physiol., 99(12):61–64.

Hutt, F. B., 1958. Genetic resistance to disease in domestic animals. Ithaca, N.Y., Cornell University Press; London., 198pp.

Ibanez, O. M., Reis, M. S., Gennari, M., Ferreira, V. C. A, Sant'Anna, O. A., Siqueira, M., and Biozzi, G., 1980. Selective breeding of high and low antibody-responder lines of guinea pigs. Immunogenet., 10:283–293.

Ishikawa, H., 1983. Depression of B lymphocytes by mastitis and treatment with levamisole. J. Dairy Sci., 66:556–561.

Ishikawa, H., 1987. Observation of lymphocyte function in perinatal cows and neonatal calves. Jpn. J. Vet. Sci., 49(3):469–475.

Kashiwazaki, Y., 1984. Lymphocyte activities in dairy cows with special preference to outbreak of mastitis pre-and postpartus. Jpn. J. Vet. Res., 32:101.

Kashiwazaki, Y., 1985. Transformation of bovine peripheral blood lymphocytes in the perinatal period. Jpn. J. Vet. Sci., 47(2):337–339.

Kehrli, M. E., Jr., Nonnecke, B. J., and Roth, J. A., 1989a. Alterations in bovine lymphocyte function during the periparturient period. Am. J. Vet. Res., 50(2):215–220.

Kehrli, M. E. Jr, Nonnecke, B. J., and Roth, J. A., 1989b. Alterations in bovine neutrophil function during the periparturient period. Am. J. Vet. Res., 50(2):207–214.

Kehrli, M. E. Jr., Goff, J. P., Harp, J. A., Thurston, J. R., Norcross, N. L., 1990a. Effects of preventing periparturient hypocalcemia in cow by parathyroid hormone administration on hematology, conglutinin, immunoglobulin and shedding of *Staphylococcus aureus* in milk. J. Dairy Sci., 73(8):2103–2111.

Kehrli, M. E., Schmalstieg, F. C., Anderson, D. C., Van Der Maaten M. J., Hughes, B. J., Ackermann, M. R., Willhelmsen, C. L., Brown, G. B., Stevens, M. G., and Whetstone, C. A., 1990b. Molecular definition of the bovine granulocytopathy syndrome: Identification of deficiency of the Mac-I (CD 11b/CD18) glycoprotein. Am. J. Vet. Res., 51:1826–1836.

Kehrli, M. E. Jr., Weigel, K. E., Freeman, A. E., Thurston, J. R., and Kelley, D. H., 1991. Bovine sire effects on daughters' in vitro blood neutrophil functions, lymphocyte blastogenesis, serum complement and conglutinin levels. Vet. Immunol. Immunopath., 27:303–319.

Kelley, K. W., 1990. The role of growth hormone in modulation of the immune response. Ann. N.Y. Acad. Sci., 594:95–103.

Kelley, K. W., Greenfield, R. E., Evermann, J. F., Parish, S. M., and Perryman, L. E., 1982. Delayed-type hypersensitivity, contact hypersensitivity, and phytohemagglutinin skin-test responses of heat and cold-stressed calves. Am. J. Vet. Res., 43(5):775–779.

Kelm, S. C., Detilleux, J. C., Freeman, A. E., Kehrli, Jr., M. E., Dietz, A. B., Fox, L. K., Butler, J. E., Kasckovics, I., and Kelley, D. H. Genetic association between parameters of innate immunity and measures of mastitis in periparturient Holstein cattle. J. Dairy Sci. (submitted).

Kensinger, M. H., Hurley, D. J., and Wilson, R. A., 1990. Culture conditions for blastogenic responses of bovine mammary mononuclear cells. Vet. Immunol. Immunopath., 24:323–330.

Khansari, D. N., Murgo, A. J., and Faith, R. E., 1990. Effects of stress on the immune system. Immunol. Today, 11(5):170–175.

Kollmann, D., 1993. Thesis: Eimeria infections in cows and their calves during the periparturient phase. Veterinarmedizin, pp. 1–150. (in German, with English abstract).

Kremer, W. D. J., Noordhuizen-Stassen, E. N., and Lohuis, J. A. C. M. 1990. Host defence mechanisms and bovine coliform mastitis—a review. Vet. Quart. 12(2):103–113.

Kuby, J., 1997. Immunology. Third edition., W. H. Freeman and Company, USA.

Larsen, B., Jensen, N. E., Madsen, P., Nielsen, S. M., Klastrup, O. and Madsen, P. S., 1985. Association of the M blood group system with bovine mastitis. Anim. Blood Groups Biochem. Genet., 16:165–173.

Lewin, H., 1989. Disease resistance and immune response genes in cattle: Strategies for their detection and evidence of their existence. J. Dairy Sci., 72(50):1334–1348.

Lewin, H., 1994., Host genetic mechanism of resistance and susceptibility to a bovine retroviral infection. Anim. Biotech., 5(2):183–191.

Liacopoulos-Briot, M., Bouthillier, Y., Mouton, D., Lambert, F., Dcreusefond, C., Stiffel, C., and Biozzi, G., 1972. Comparison of skin allograft rejection and cytotoxic antibody production in tow line os mice genetically selected for 'high' and 'low' antibody synthesis. Transplant., 14:590–596.

Liacopoulos-Briot, M., Lambert, F., Mouton, D., Bouthillier, Y., Decreusefond, C., Stiffel, C., and Biozzi, G., 1972. Stimulation des lymphocytes par la phytohémagglutinine chez les souris des lignées génétiquement sélectionnées d'après le caractère 'production d'anticorps'. Ann. Immunol., Paris, 123:135.

Lie, Ø. 1979. Genetic analysis of some immunological traits in young bulls. Acta Vet. Scand., 20:372–386.

Lie, Ø., 1985. Genetic approach to mastitis control. Kiel. Milchwirtsch. Forshungsber., 37:487.

Lie, Ø., Solbu, H., Larsen, H. J., and Spooner, R. L., 1986. Possible association of antibody responses to human serum albumin and (T,G)-A—L with the bovine major histocompatibility complex (BoLA). Vet. Immunol. Immunopath., 11:333–350.

Logg, M. H., 1942. Effect of pregnancy and parturition on pulmonary tuberculosis. Br. Med. J., 1:468–469.

Lundén, A., Sigurdardottir, S., Edfors-Lilja, I., Danell, B., Rendel, J. and Andersson, L., 1990. The relationship between bovine major histocompatibility complex class II polymorphism and disease studied by use of bull breeding values. Anim. Genet., 21:221–232.

Lutje, V. and Black, S. J., 1991. Cellular interactions regulating the in vitro response of bovine lymphocytes to ovalbumin. Vet. Immunol. Immunopath., 28(3–4):275–288.

MacPhee, I. A. M., Antoni, F. A., and Mason, D. W., 1989. Spontaneous recovery of rats from experimental allergic encephalomyelitis is dependent on regulation of the immune system by endogenous adrenal corticosteroids. J. Exp. Med., 169:431–445.

Madsen, P., 1989. Genetic resistance to bovine mastitis. Curr. Top. Vet. Med. Anim. Sci., 52:169–177.

Mallard, B. A., Wilkie, B. N., and Kennedy, B. W., 1989. Genetic and other effects on antibody and cell mediated immune response in SLA-defined miniature pigs. Anim. Genet., 20:167–178.

Mallard, B. A., Wilkie, B. N., Kennedy, B. W., and Quinton, M., 1992. Use of Estimated Breeding Values in a selection index to breed Yorkshire pigs for high and low immune and innate resistance factors. Anim. Biotech., 3(2):257–280.

Mallard, B. A., Wagter, L. C., Ireland, M. J., and Dekkers, J. C. M., 1997. Effects of growth hormone, insulin-like growth factor I, and cortisol on periparturient antibody response profiles of dairy cattle. Vet. Immunol. Immunopath. (accepted for publication).

Mallard, B. A., Wilkie, B. N., Kennedy, B. W., Gibson, J., and Quinton, M., 1998. Immune responsiveness in swine: Eight generations of selection for high and low immune response in Yorkshire pigs. 6th World Congr. Genet. Appl. Livest. Prod., Australia.

Mallard, B. A., Leslie, K. E., Dekkers, J. C. M., Hedge, R., Bauman, M., and Stear, M. J., 1995. Differences in bovine lymphocyte antigen associations between immune response and risk of disease following intramammary infection with *Staphylococcus aureus*. J. Dairy Sci., 78:1937.

Mallard, B. A., Dekkers, J. C., Ireland, M. J., Leslie, K. E., Sharif, S, Lacey-Van Kampen, C., Wagter, L. and Wilkie, B. N., 1997. Alteration in immune responsiveness during the peripartum period. J. Dairy Sci. (accepted for publication).

Malo, D., Hu, J., Skamene, E., and Schurr, E., 1994. Population and molecular genetics of susceptibility to intracellular pathogens. Anim. Biotech., 5(2):173–182.

Manak, R. C., 1982. Mitogenic responses of peripheral blood lymphocytes from pregnant and ovariectomized heifers and their modulation by serum. J. Reprod. Immunol., 4:263–276.

Martin, W., Meek, A., and Willeberg, P., 1987. Veterinary Epidemiology: principles and methdods. $1^{st}$ Edition. Iowa State University Press. pp. 129–131.

Mason, D., 1991. Genetic variation in the stress response: susceptibility to experimental allergic encephalomyelitis and implication for human inflammatory disesase. Immunol. Today, 12(2):57–60.

Matthews, K. R., Harmon, R. J. and Langlois, B. E., 1992. Prevalence of Staphylococcus species during the periparturient period in primiparous and multiparous cows. J. Dairy Sci., 75:1835–1839.

McClure, A. M., Christopher, E. E., Wolff, W. A., Fales, W. H., Krause, G. F., and Miramonti, J., 1994. Effect of Re-17 mutant *Salmonella typhimurium* bacterin toxoid on clinical coliform mastitis. J. Dairy Sci., 77:2272–2280.

Mejdell, C. M., Lie, Ø., Solbu, H., Amet, E. F., and Spooner, R. L., 1994. Association of major histocompatibility complex antigens (BoLA-A) with AI bull progeny test results for mastitis, ketosis, and fertility in Norwegian cattle. Anim. Genet., 25:99–104.

Miglior, F., Burnside, E. B., and Dekkers, J. C. M., 1995. Nonadditive genetic effects and inbreeding depression for somatic cell counts of Holstein cattle. J. Dairy Sci., 78:1168–1173.

Mouton, D., Bouthillier, Y., Oriol, R., Decreusefond, C., Stiffel, C., and Biozzi, G., 1981.
Intensité de la réaction d'hypersensibilitée retardée chez les souris des lignées sélectionnées <<bonnes>> et <<mauvaises>> productrices d'anticorps. Ann. Immunol., Paris, 125C:581–588.

Morrow-Tesch, J. L., McGlone, J. J., and Norman, R. L., 1993. Consequences of restraint on natural killer cell activity, behaviour, and hormone levels in rhesus macaques. Psychoneuroendocrinol., 18(5–6):383–385.

Morrow-Tesch, J. L., Wollen, N., and Hahn, L., 1996. Response of $\gamma\delta$ T-lymphocytes to heat stress in *Bos taurus* and *Bos indicus* crossbred cattle. J. Therm. Biol., 21(2):101–108.

Myllys, V. and Rautala, H., 1995. Characterization of clinical mastitis in primiparous heifers. J. Dairy Sci., 78:538–545.

Nardone, A., Lacetera, N., Bemabucci, U., and Ronchi, B., 1997. Composition of colostrum from dairy heifers exposed to high air temperatures during late pregnancy and the early postpartum period. J. Dairy Sci., 80:838–844.

Nagahata, H., Ogawa, A., Sanada, Y., Noda, H., and Yamamota, S., 1992. Peripartum changes in antibody producing capability of lymphocytes from dairy cows. Vet. Quart., 14(1):39–40.

Nagahata, H., Makino, S., Takeda, S., Takahashi, H., and Noda, H., 1988. Assessment of neutrophil function in the dairy cow during the perinatal period. J. Vet. Med., 35:747–751.

Nakao, T., and Grunnert, E., 1990. Adrenocortical function in cows with the downer cow syndrome. A preliminary report. J. Vet. Med., 37(8):610–613.

Nardone, A., Lacetera, N., Bemabucci, U., and Ronchi, B., 1997. Composition of colostrum from dairy heifers exposed to high air temperatures during late pregnancy and the early postpartum period. J. Dairy Sci., 80:838–844.

Nash, M. S., 1994. Excercise and immunology. Med. Sci. Sports Exerc., 26(2):125–127.

National Mastitis Council. 1994. Udder Topics, 17(4):1–4.

Newbould, F. H. S., 1976. Phagocytic activity of bovine leukocytes during pregnancy. Can. J. Comp. Med., 40:111–116.

Nickerson, S. C., Owens, W. E., Boddie, R. L., and Boddie, N. T., 1992. The effect of chronic immunostimulation of the nonlactating bovine mammary gland with interleukin-2, pokeweed mitogen and lipopolysaccharide. J. Dairy Sci., 75(12):3339–3351.

Nickerson, S. C., 1993. Vaccination programs for preventing and controlling mastitis. Natl. Mast. Coun. Reg. Mtg. Proc., pp. 64–72.

Nickerson, S. C., Owens, W. E., Rejman, J. J., and Oliver, S. P., 1993. Effects of interleukin-1 and interleukin-2 on mammary gland leukocyte populations and histology during the early nonlactation period. J. Vet. Med., 40:621–633.

Nickerson, S. C., Baker, P. A., and Trinidad, P., 1989. Local immunostimulations of the bovine mammary gland with interleukin-2. J. Dairy Sci., 72:1764–1773.

Nielson, U. S., Pedersen, G. A., Pedersen, J., and Jensen, J. 1997., In Proc. Genet. Improvement Func. Traits in Cattle., Uppsula, Sweden.

Nonnecke, B. J., and Harp, J. A., 1985. Effect of chronic staphylococcal mastitis on mitogenic responses of bovine lymphocytes. J. Dairy Sci., 68:3323–3328.

de Oliveira, S. L., Ibanez, O. M., Mouton, D., Sant'Anna, O. A., Siqueira, M., and Biozzi, G., 1985. Independent polygenic regulation of quantitative antibody responsiveness and expression of delayed-type hypersensitivity (DTH). Expl. Clin. Immunogenet., 2:223–233.

Ontario Milk Producer, February 1997. Prices., p30.

Oppenheim, J. J., Kovacs, E. J., Matsuchima, K., and Durams, S. K., 1986. There is more than one interleukin-1. Immunol. Today, 7:45–56.

Paape, M. J., Hafs, H. D. and Snyder, W. W., 1963. Variation of estimated numbers of milk somatic cells stained with wright's stain or pyronin y-methyl green stain. J. Dairy Sci., 46: 1211–1216.

Park, Y. H., Fox, L. K., Hamilton, M. J. and Davis, W. C., 1992. Bovine mononuclear leukocyte subpopulations in peripheral blood and mammary gland secretions during lactation. J. Dairy Sci., 75:998–1006.

Parker, K. A., Leyh, R., Field, M. F., and Anderson, G. A., 1994. Serologic response of cattle to core antigen vaccination. Natl. Mast. Coun. Ann. Mtg. Proc., pp. 326–327.

Peter, A. T. and Bosu, W. T. K., 1987. Peripartal endocrine changes associated with retained placenta in dairy cows. Theriogenol., 28:383–393.

Petersen, B. H., Rapaport, R., Henry, D. P., Huseman, C., and Moore, W. V., 1990. Effect of treatment with biosynthethic human growth hormone (GH) on peripheral blood lymphocyte populations and function in growth hormone-deficient children. J. Clin. Endocrinol. Metab., 70:1756–1760.

Pinard, M. H. and Van der Zijpp, A. J., 1992. Divergent selection for immune resposiveness in chickens: Estimation of realized heritability with an animal model. J. Anim. Sci., 70(10):2986–2993.

Politis, I., Hidiroglou, M., Batra, T. R., Gilmore, J. A., Gorewit, R. C., and Scherf, H., 1995. Effects of vitamin E on immune function of dairy cows. Am. J. Vet. Res., 56(2):179–184.

Puel, A, and Mouton, D., 1996. Genes responsible for quantitative regulation of antibody production. Crit. Rev. Immunol., 16:223–250.

Reents, R., Dekkers, J. C. M., and Schaeffer, L. R., 1995. Genetic evaluation for somatic cell score with a test day model for multiple lactations. J. Dairy Sci., 78:2858–2870.

Rich, A. R., 1951. The influence of sex and age. In: The pathogenesis of tuberculosis. 2nd ed. Springfield: Charles C Thomas. pp. 189–195.

Rogers, M. P., Dubey, D., and Rech P., 1979. The influence of psyche and the brain on immunity and disease susceptibility: a critical review. Psychosom. Med., 41:147–164.

Romagnani, S., 1997. The Th1/Th2 paradigm. Immunol. Today, 18(6):263–266.

Roth, J. A., and Kaeberle, M. L., 1982. Effect of glucocorticoids on the bovine immune system. J. Am. Vet. Med. Assoc., 180:894–901.

Saad, A. M., Concha, C., and Astrom, G., 1989. Alterations in neutrophil phagocytosis lymphocyte blastogenesis in dairy cows around parturition. J. Vet. Med., 36:337–345.

Sandholm, M. and Mattila, T., 1986. Mechanisms of infection and inflammation of the mammary gland—an overview. Proceedings of symposion on mastitis control and hygienic production of milk. Espoo, Finland.

Schaeffer, L. R., Minder, C. E., McMillan, I., and Burnside, E. B., 1977. Nonlinear techniques for predicting 305-day lactation production of Holsteins and Jerseys. J. Dairy Sci., 60:1636–1644.

Schiebel, I. F., 1943. Hereditary differences in the capacity of guinea-pigs for the production of diptheria antitoxin. Acta Path. Microbiol. Scand., 20:464–484.

Schukken, Y. H., Mallard, B. A., Dekkers, J. C. M., Leslie, K. E., and Stear, M. J., 1994. Genetic impact on the risk of intramammary infection following *Staphylococcus aureus* challenge. J. Dairy Sci., 77:639–647.

Schmutz, S. M., Berryere, T. G., Robbins, J. W., and Carruthers, T. D., 1992. Resistance to *Staphylococcus aureus* mastitis detected by a DNA marker. Proc. Nation. Mast. Council. pp. 124–133.

Schurmann, A., Spencer, G. S. G., and Berry, C. J., 1995. Growth hormone alters lymphocyte sub-populations and antibody production in dwarf rats in vivo. Experientia, 51:780–785.

Schutz, M. M., 1994. Genetic evaluation of somatic cell scores for united states dairy cattle. J. Dairy Sci., 77:2113–2129.

Sharif, S., Mallard, B. A., Wilkie, B. N., Sargeant, J. M., Scott, H. M., Dekkers, J. C. M., and Leslie, K. E., 1997. Associations of the bovine major histocompatibility complex DRB3 (BoLA-DRB3) alleles with occurrence of disease and milk somatic cell score in Canadian dairy cattle., Anim. Genet. (submitted).

Shook, G. E., 1989. Selection for disease resistance. J. Dairy Sci., 72:1349–1362.

Shook, G. E., 1993. Genetic Improvement of mastitis through selection on somatic cell count. Veterinary clinics of north america: Food animal practice, 9(3):563–580.

Shook, G. E. and Schutz, M. M., 1994. Selection on somatic cell score to improve resistance to mastitis in the United States. J. Dairy Sci., 77:648–658.

Shuster, D. E., Lee, E. K., and Kehrli, M. E., 1996. Bacterial growth, inflammatory cytokine production and neutrophil recruitment during coliform mastitis in cows within ten days after calving, compared with cows at midlactation. Am. J. Vet. Res., 57(11):1569–1575.

Siegel, B. P., and Gross, W. B., 1980. Production and persistence of antibodies in chickens to sheep erythrocytes. 1. Directional selection. Poultry Sci., 59:1–5.

Sigguradóttir, S., Lunden, A., and Andersson, L., 1988. Restriction fragment length polymorphis of DQ and DR class II genes of the bovine major histocompatibility complex. Anim. Genet., 19:133–150.

Smith, K. L., and Hogan, J. S., 1994. Understanding environmental mastitis. Natl. Mast. Coun. Reg. Mtg. Proc., pp. 33–38.

Smith, K. L., Todhunter, D. A., and Schoenberger, P. S., 1985. Environmental pathogens and intramammary infection during the dry period. J. Dairy Sci., 68:402–417.

Smith, V. G., Edgerton, L. A., Hafs, H. D., and Convey, E. M., 1973. Bovine serum estrogens progestins, and glucocorticoids during late pregnancy, parturition, and early lactation. J. Anim. Sci., 36:391–396.

Solbu, H., Spooner, R. L. and Lie, Ø. 1982. A possible influence of the bovine major histocompatibility complex (BOLA) on mastitis. Proc. 2nd World Congr. Genet. Appl. Livest. Prod., 7:368.

Soller, M., 1994. Marker assisted-selection-an overview. Anim. Biotech., 5:193–207.

Sordillo, L. M., 1995. Vaccination as a protection against bovine mastitis. Natl. Mast. Coun. Reg. Mtg. Proc., pp. 64–68.

Sordillo, L. M., and Babiuk, L. A., 1991. Controlling acute *Escherichia coli* mastitis during the periparturient period with recombinant bovine interferon gamma. 1991. Vet. Microbiol., 28:189–198.

Sordillo, L. M., Redmon, M., Campos, M., Warren, L., and Babiuk, L. A., 1992. Cytokine activity in bovine mammary gland secretions during the periparturient period. Can. J. Vet. Res., 55:298–301.

Spangelo, B. L. and Gorospe, W. C., 1995. Role of cytokines in the neuroendocrine-immune system axis. Front. Neuroendocrinol., 16(1):1–22.

Sridama, V., Pacini, F., Yang, S-L., Moawad, A., Reilly, M., and DeGroot, L. J., 1982. Decreased levels of helper T cells. N. Engl. J. Med., 307:352–356.

Sternberg, E. M., Hill, J. M., Chrousos, G. P., Kamilarus, T., Listwak, S. J., Gold, P. W., and Wilder, R. L., 1989. Inflammatory mediator-induced hypothalamic-pituitary-adrenal axis activation is defective in streptococcal cell wall arthritis-susceptible Lewis rats. Proc. Natl. Acad. Sci. USA, 86(7):2374–2378.

Sulimova, G. E., Udina, I. G., Shaikhaev, G. O., and Zakharov, I. A., 1995. DNA polymorphism at the BoLA-DRB3 gene of cattle in relation to resistance to susceptibility to leukemia. Russ. J. Genet., 31:1105–1109.

Todhunter, D. A., Smith, K. L., and Hogan, J. S., 1990. Growth of Gram-negative bacteria in dry cow secretions. J. Dairy Sci., 73:363–372.

Van der Zijpp, A. J., Frankena, K., Boneschanscher, J., and Nieuwland, M. G. B., 1983. Genetic analysis of primary and secondary immune response in the chicken. Poultry Sci., 6: 565–572.

Van Kampen, C. and Mallard, B. A., 1997. Effects of peripartum stress and disease on bovine lymphocyte subsets. Vet. Immunol. Immunopath. (Accepted for publication).

Van Werven, T., Noordhuizen-Stassen, E. N., Daemen, A. J. J. M., Schukken, Y. H., Brand, A. and Burvenich, C., 1997. Preinfection in vitro chemotaxis, phagocytosis, oxidative burst, and expression of CD11/CD18 receptors and their predictive capacity on the outcome of mastitis induced in dairy cows with *Escherichia coli*. J. Dairy Sci., 80:67–74.

Vassilopoulou-Sellin, R., 1994. Endocrine effects of cytokines. Oncology. Huntingt., 8(10):4 3–46.

Vega, J. R., Gibson, C. A., Skaar, T. C., Hadsell, D. L. and Baumrucker, C. R., 1991. Insulin-like growth factor (IGF) 1 and 2 and IGF binding proteins in serum and mammary secretions during the dry period and early lactation in dairy cows. J. Anim. Sci., 69:2538–2547.

Watson, D. L., and Schwartskoff, C. L., 1990. A field trial to test the efficacy of a staphylococcal mastitis vaccine in commercial dairies in Australia. In: Proc. Int. Symp. Bov. Mast., Indianapoli, IN, pp73.

Weigel, K. A., Kehrli, Jr., M. E., Freeman, A. E., Thurston, J. R., Stear, M. J., and Kelley, D. H., 1991. Associations of class I bovine lymphocyte antigen complex alleles with in vitro blood neutrophil functions, lymphocyte blastogenesis, serum complement and conglutinin levels in dairy cattle. Vet. Immunol. Immunopath., 27:321–335.

Weiland, F., and Straub, O. C., 1976. Differences in the in vitro response of lymphocytes from leukotic and normal cattle to concanavalin A. Res. Vet. Sci., 20:340–341.

Weinberg, E. D., 1984. Pregnancy-associated depression of cell-mediated immunity. Rev. Inf. Dis., 6(6):814–831.

Wells, P. W., Burrells, C., and Martin, W. B., 1977. Reduced mitogenic responses in cultures of lymphocytes from newly calved cows. Clin. Exp. Immunol., 29:159–161.

Weller, J. I., Saran, A., and Zeliger, Y., 1992. Genetic and environmental relationships among somatic cell count, bacterial infection, and clinical mastitis. J. Dairy Sci., 75:2532–2540.

Wijngaard, P. L. J., Metzelaar, M. J., MacHugh, N. D., Morrison, W. I., and Clevers, H. C., 1992. Molecular characterization of the WC1 antigen expressed specifically on bovine CD4-CD8-↓δ T lymphocytes. J. Immunol., 149:3273–3277.

Williams, M. R., and Hill, A. W., 1982. A role for IgM in the in vitro opsonisation of *Staphylococcus aureus* and *Escherichia coli* by bovine polymorphonuclear leucocytes. Res. Vet. Sci., 33:47–53.

Wright, P., 1987. Enzyme Immunoassay: observations on aspects of quality control. Vet. Immunol. Immunopath., 17:441–452.

Xu, A., van Eijk, M. J. T., Park, C., and Lewin, H. A., 1993. Polymorphism in BoLA-DRB3 exon 2 correlates with resistance to persistent lymphocytosis caused by bovine leukemia virus. J. Immunol., 151:6977–6985.

Yang, T. J., Mather, J. F., and Rabinovsky, E. D., 1988. Changes in subpopulations of lymphocytes in peripheral blood, and supramammary and prescapular lymph nodes of cows with mastitis and normal cows. Vet. Immunol. Immunopath., 18:279–285.

Yoshida, A., Ishioka, C., Kimata, H., and Mikawa, H., 1992. Recombinant human growth hormone stimulates B cell immunoglobulin synthesis and proliferation in serum-free medium. Acta Endocrinologica, 126:524–529.

Zanotti, M., Poli, G., Ponti, W., Polli, M., Rocchi, M., Bolzani, E., Longeri, M., Russo, S., Lewin, H. A., van Eijk, M. J. T., 1996. Association of BoLA class II haplotypes with subclinical progression of bovine leukemia virus infection in Holstein-Friesian cattle. Anim. Genet. 27:337–341.

Zhang, W. C., Dekkers, J. C. M., Banos, G., and Burnside, E. B., 1993. Sire genetic evaluation for somatic cell score and relationships with other traits. 1993 Dairy Research Report, Ontario Ministry of Agriculture, Food and Rural Affairs, Publ. No. 0193, pp., 106–109.

DETAILED FIGURE LEGENDS

FIG. 1. LS Means of antibody response to OVA in A) serum and B) whey by antibody response group following immunization at weeks −8, −3, and 0 as measured by enzyme linked immunosorbent assay (ELISA). Group 1=high measurable antibody response; Group 2=lack of measurable response to immunization postpartum (week 0); Group 3=lack of measurable response to immunization pre- and postpartum; Pop=population mean. Animal classification is based on serum antibody response to OVA. Significant differences between animals in the three groups are indicated by different letters above error bars (P≦0.05).

Figure 2:
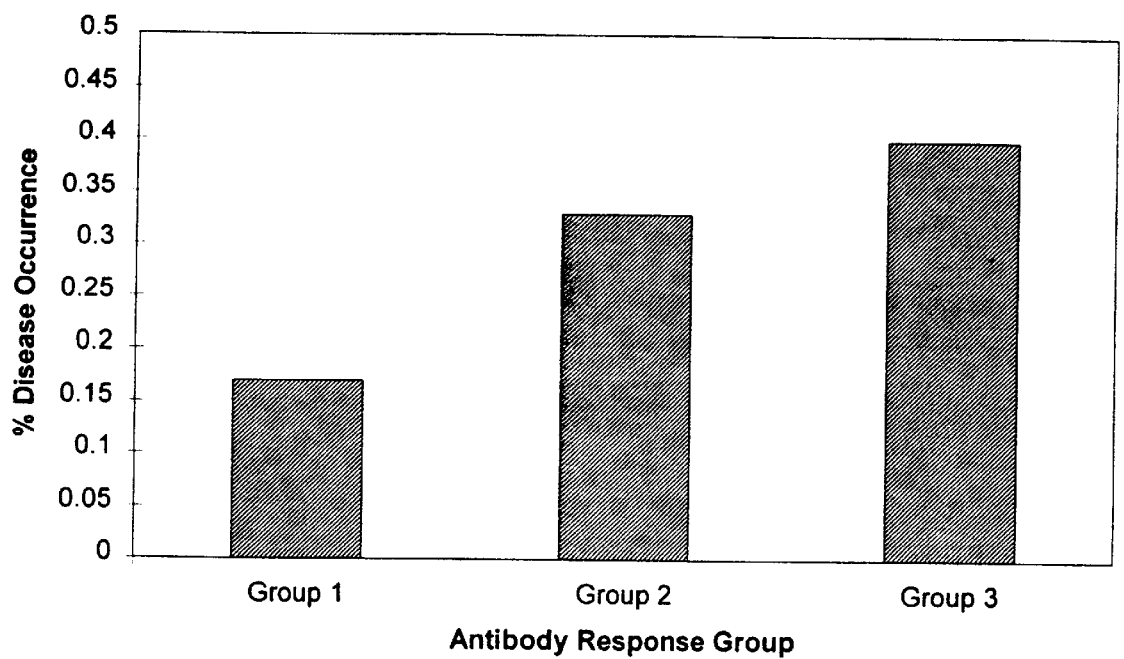
FIG. 2 is a bar graph showing the percentage of disease occurrence in the animals of Group 1, Group 2 and Group 3.

FIG. 2. Percent disease occurrence by antibody response group. Group 1=high measurable antibody response; Group 2=lack of measurable response to immunization postpartum (week 0); Group 3=lack of measurable response to immunization pre- and postpartum. Animal classification is based on serum antibody response to ovalbumin (OVA).

FIG. 3. LS Means of serum antibody response to ovalbumin (OVA) by antibody response group. Group 1=high antibody response, Group 2=average antibody response, and Group 3=low antibody response based on described index, and Population mean (PM). Significant differences between groups are indicated with lower case letters between groups and differences over time are indicated by different uppercase letters (P<0.05).

Figure 4:
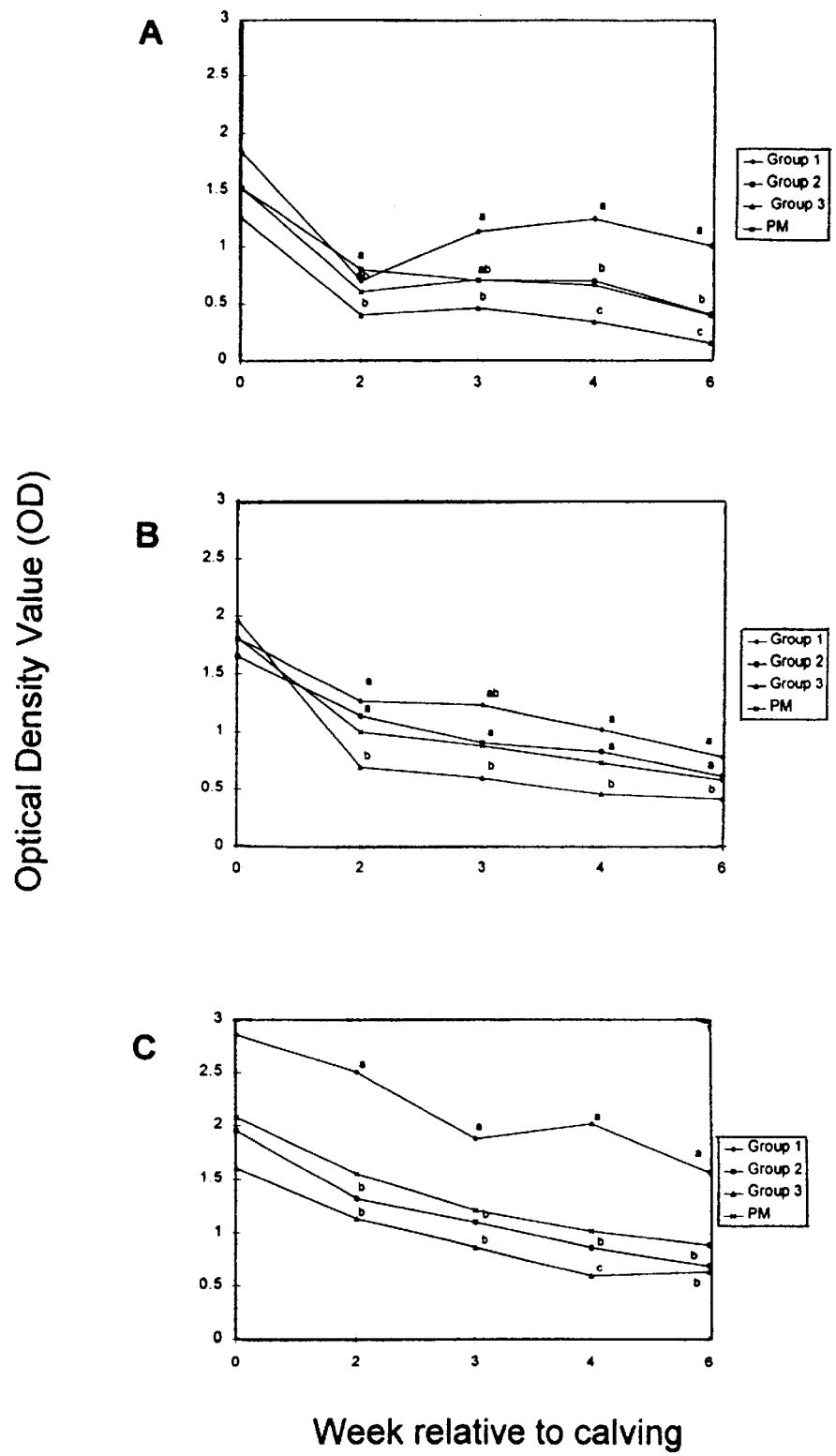
FIGS. 4A–C are graphs showing the anti-OVA antibody levels in whey versus time for the animals in Group 1, Group 2 and Group 3.

FIG. 4. LS Means of whey antibody response to ovalbumin (OVA) by antibody response group for A) Herd 1, B) Herd 2 and C) Herd 3. Group 1=high antibody response, Group 2=average antibody response, and Group 3=low antibody response based on described index, and Population mean (PM). Significant differences between groups are indicated with lower case letters and differences over time are indicated by different uppercase letters (P<0.05).

Figure 5:
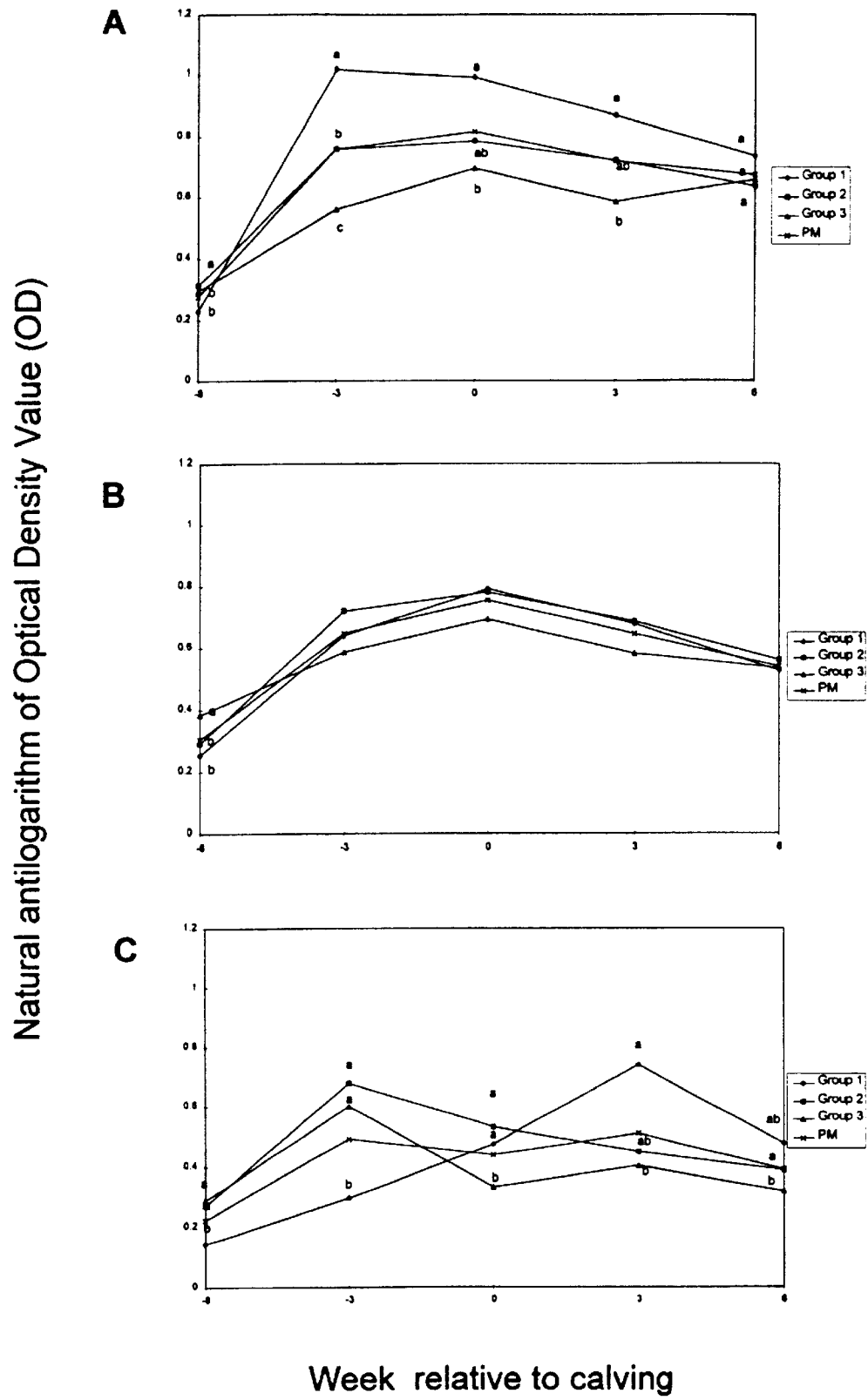
FIGS. 5A–C is a graph showing the anti-E. coli antibody levels versus time for the animals of Group 1, Group 2 and Group 3.

FIG. 5. LS Means of sera antibody response to *E. coli* for A) Herd 1, B) Herd 2 and C) Herd 3. Group 1=high antibody response, Group 2=average antibody response, and Group 3=low antibody response based on described index, and population mean (PM). Significant differences between groups are indicated with different lower case letters (P<0.05).

Figure 6:
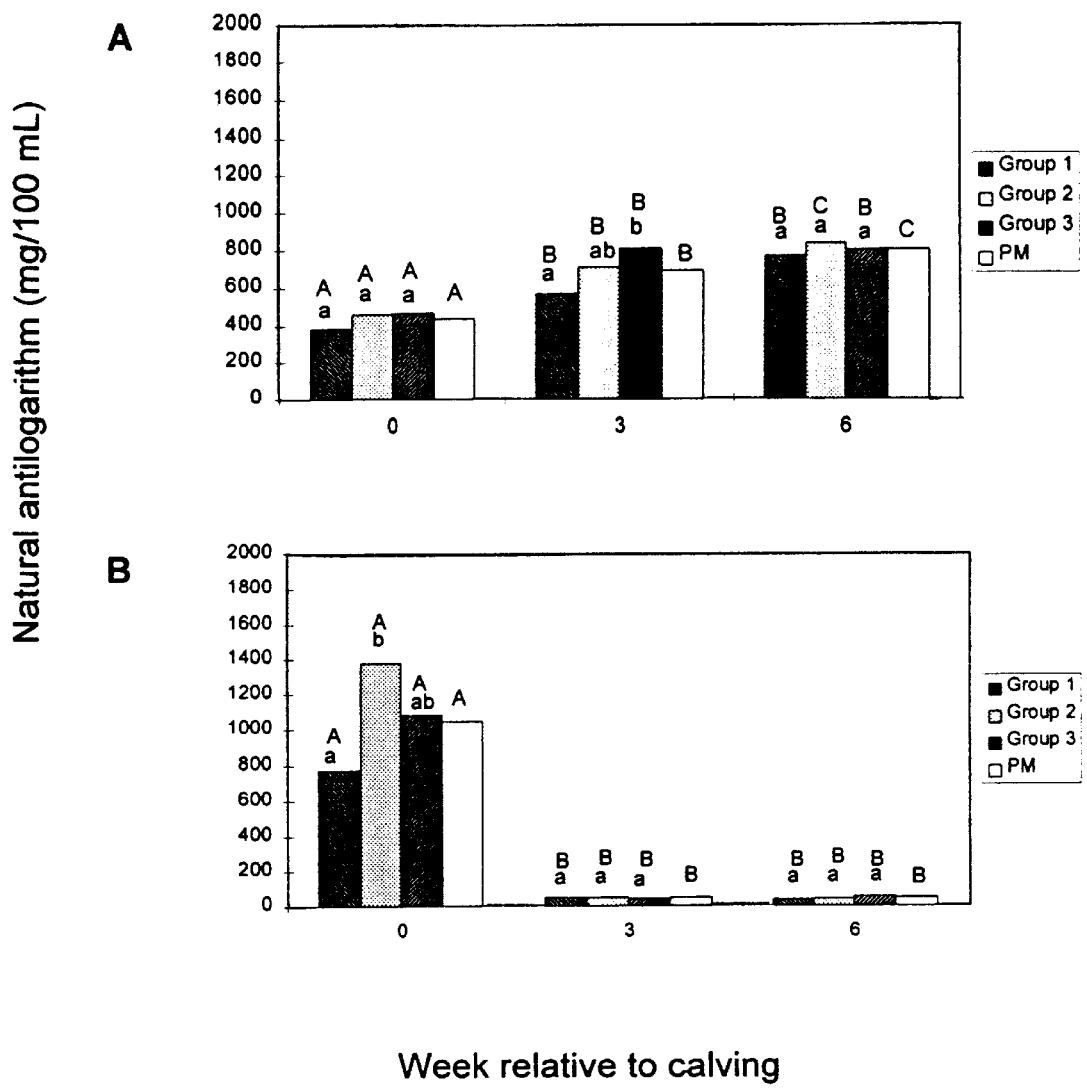
FIGS. 6A and B are bar graphs showing antibody levels versus time in the animals of Group 1, Group 2 and Group 3.

FIG. 6. LS Means of $IgG_1$ in A) sera and B) whey. Group 1=high antibody response, group 2=average antibody response, and Group 3=low antibody response based on described index, and Population mean (PM). Significant differences between groups are indicated with lower case letters and differences over time are indicated by different upper case letters(P<0.05).

FIG. 7. Rate of Mastitis occurrence (%) by antibody response group within herd.

Figure 8:
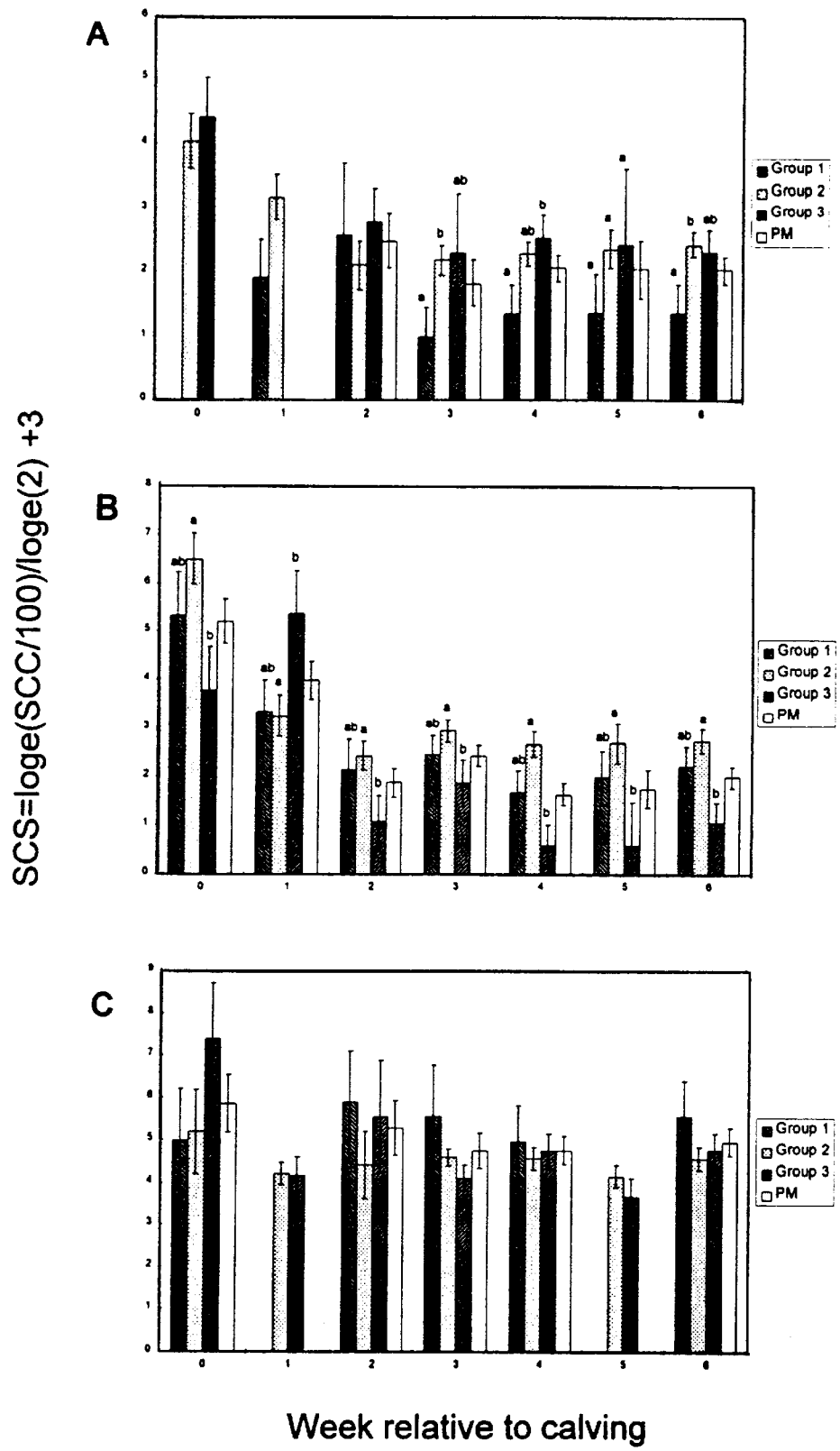
FIGS. 8A–C is a graph showing the somatic cell score versus time for the animals in Herd 1, Herd 2 and Herd 3.

FIG. 8. LS Means of Somatic Cell Score by antibody response group for A) Herd 1; B) Herd 2; and C) Herd 3. Group 1=high antibody response, Group 2=average antibody response, and Group 3=low antibody response based on described index, and Population mean (PM). Significant differences between groups are indicated with different lower case letters (P<0.05).

Figure 9:
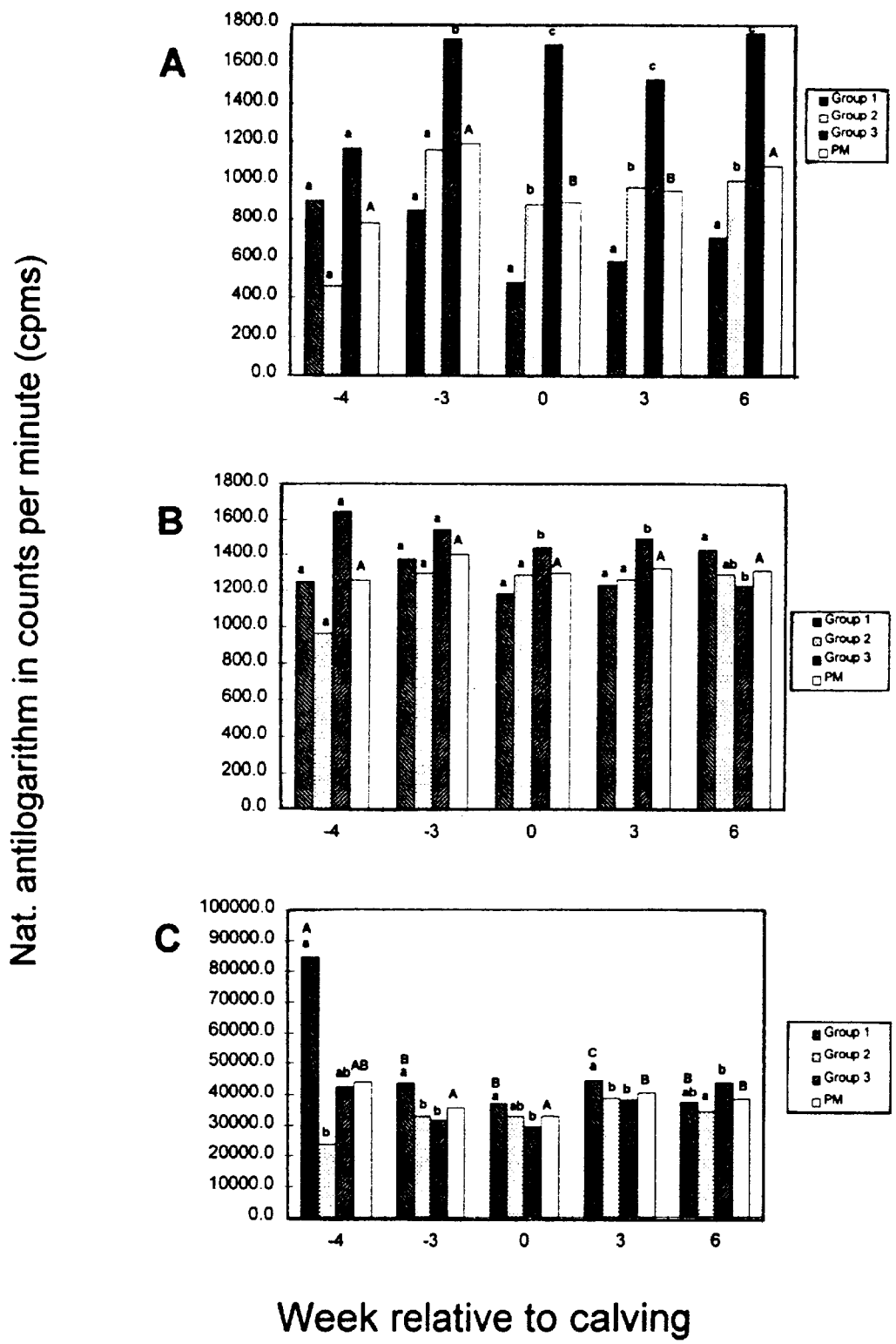
FIG. 9 is a graph showing Con A stimulated lymphocyte proliferatives versus time for the animals of Group 1, Group 2 and Group 3.

FIG. 9. Type III LS Means of counts per minute (cpm) measuring unstimulated (1A) and stimulated lymphocyte proliferation to ovalbumin (OVA; 1B) and concanavalin A (Con A; 1C). Group 1=high antibody response to OVA, Group 2=average antibody response to OVA, and Group 3=low antibody response to OVA and Population mean=PM. Significant differences between groups are indicated with lower case letters and differences over time are indicated by different upper case letters(P<0.05).

Figure 10:
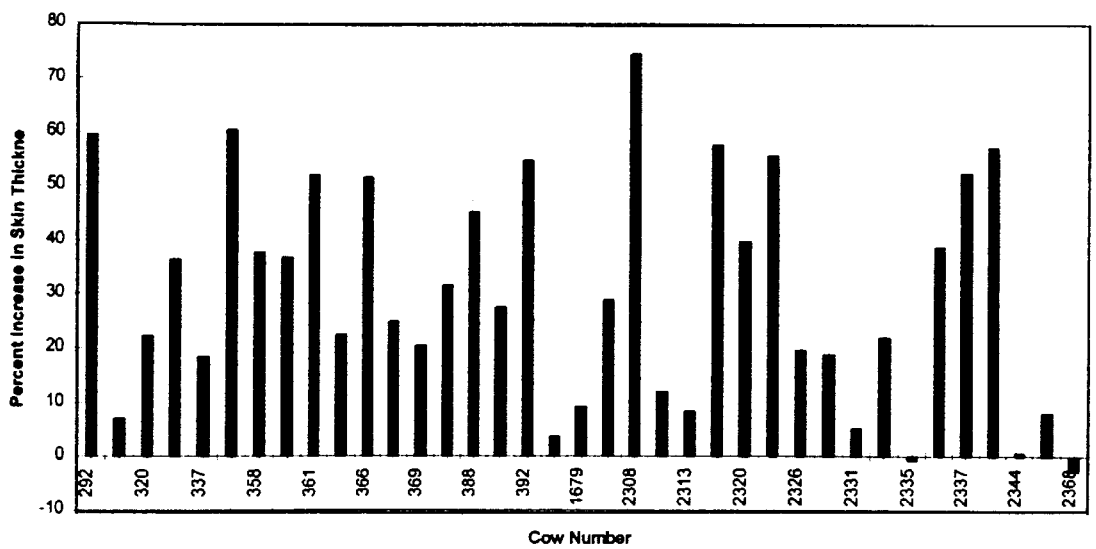
FIG. 10 is a bar graph showing the percent increase in skin thickness after challenge with PPD in cows and heifers.

FIG. 10. Percent increase in skin thickness 48 hours after challenge with the purified protein derivative of tuberculin (PPD) in cows and heifers previously sensitized to BCG.

FIG. 11. Type III LS Means of lymphocyte counts (cells/mL) in blood during the peripartum period. Group 1=high antibody response to OVA, Group 2=average antibody response to OVA, and Group 3=low antibody response to OVA and Population mean=PM. Significant differences between groups are indicated with lower case letters and differences over time are indicated by different upper case letters(P<0.05).

Figure 12:
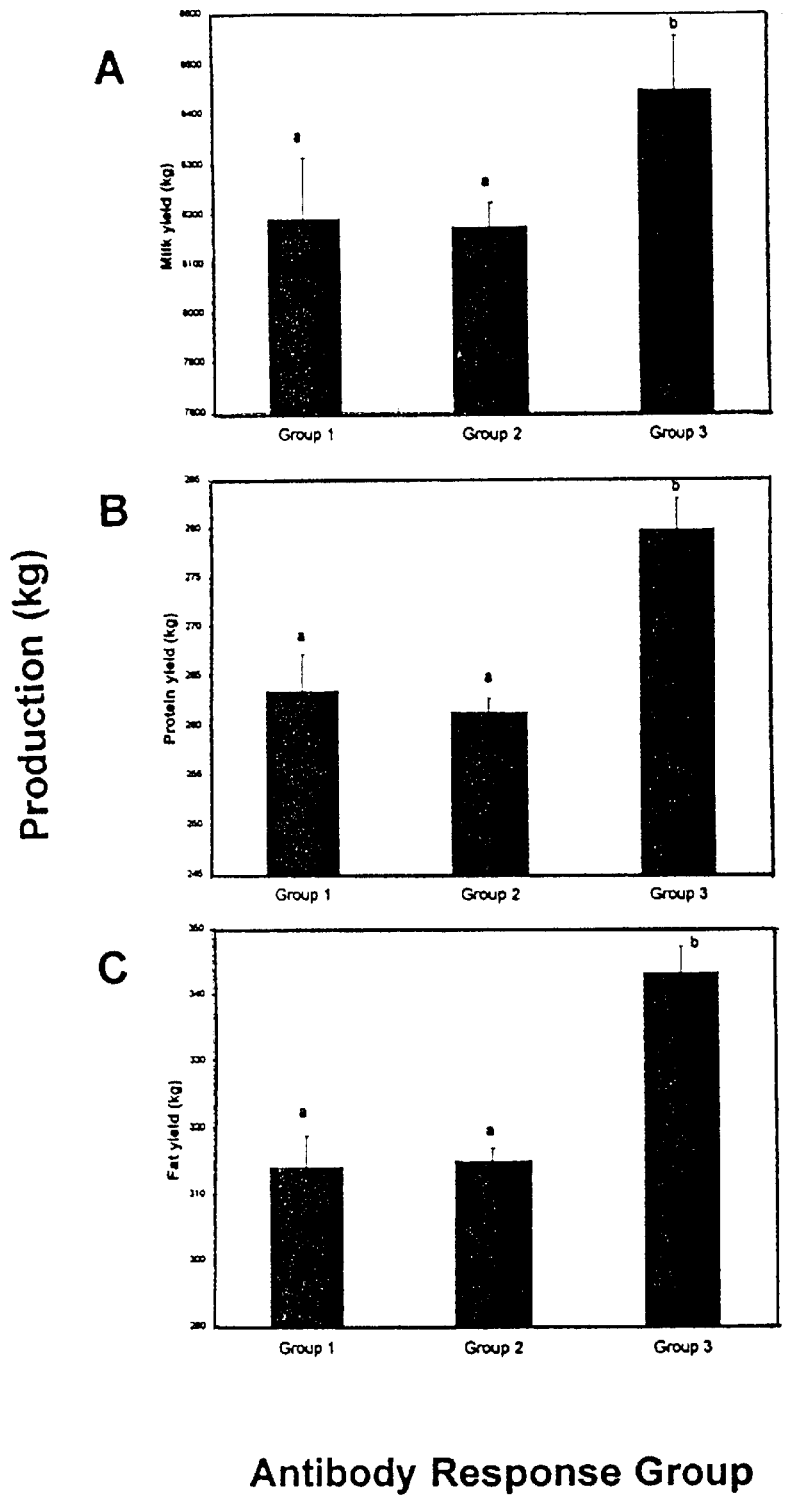
FIGS. 12A–C are bar graphs showing the production versus antibody response for the animals of Group 1, Group 2 and Group 3.

FIG. 12. Type III LS Means of projected 305 day yield for milk (1A), protein (1B), and fat (1C). Group 1=high antibody response, Group 2=average antibody response, and Group 3=low antibody response based on described index, and Population mean (PM). Significant differences between groups are indicated with lower case letters (P<0.05).

Figure 13:
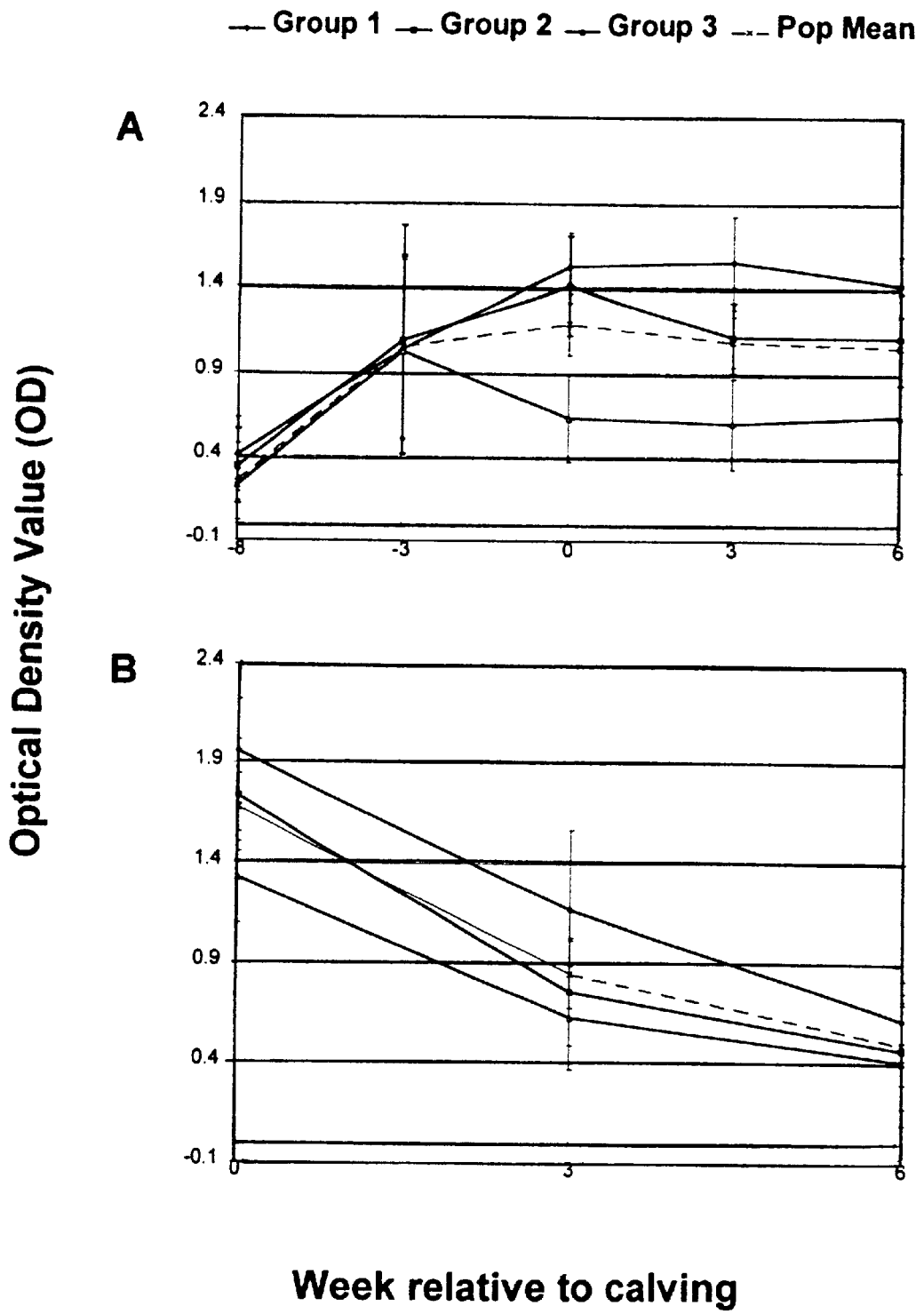
FIGS. 13A and B are graphs showing the anti-OVA antibody levels versus time for the animals of Group 1, Group 2 and Group 3.

FIG. 13. LS Means of antibody response to OVA in A) serum and B) whey by antibody response group following immunization at weeks −8, −3, and 0 as measured by enzyme linked immunosorbent assay (ELISA). Group 1=high measurable response; Group 2=lack of measurable response to immunization postpartum (week 0); Group 3=lack of measurable response to immunization pre- and postpartum; Pop=population mean. Animal classification is based on serum antibody response to OVA. Significant differences between animals in the three groups are indicated by different letters above error bars (P<0.05).

Figure 14:
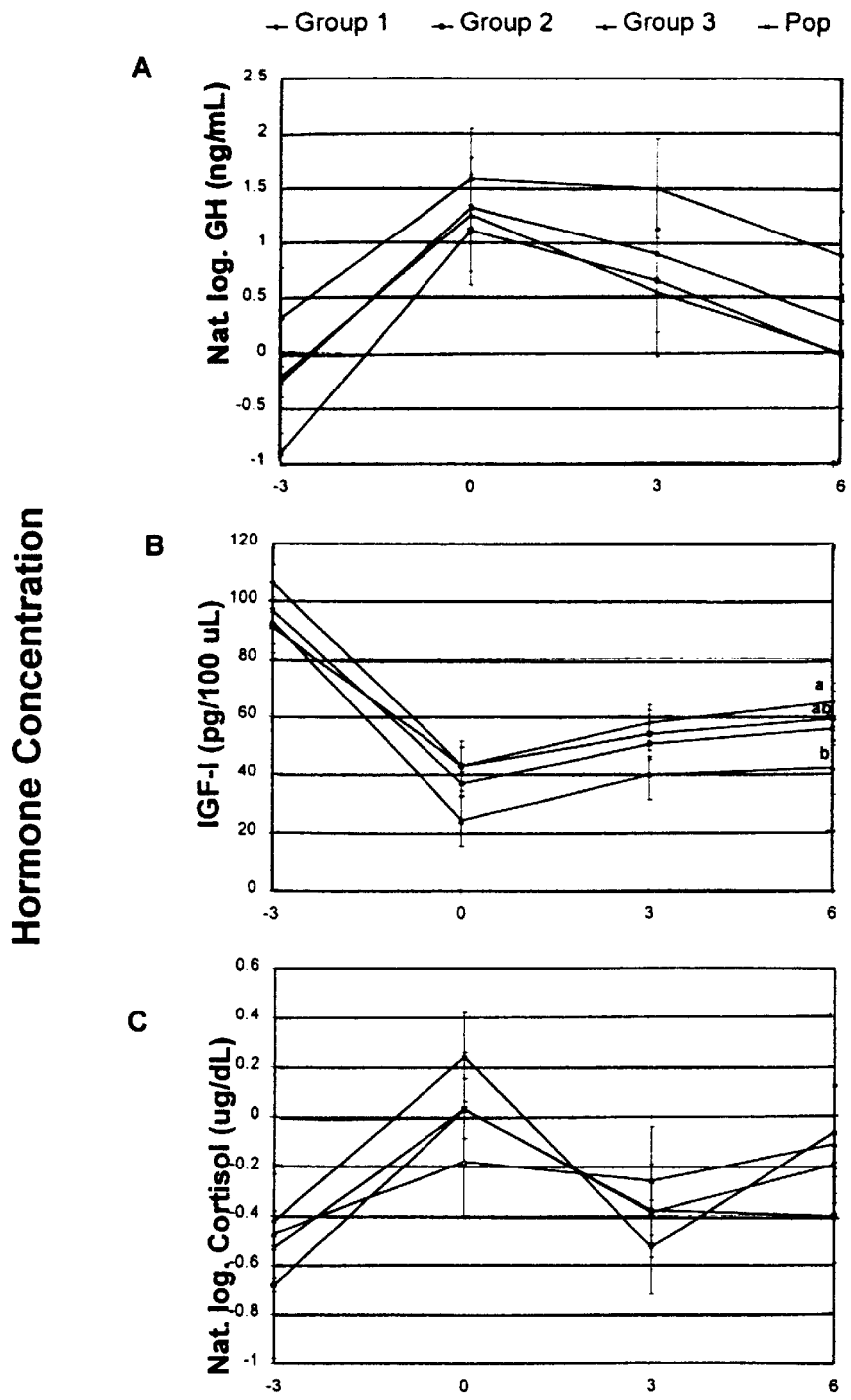
FIGS. 14A–C are graphs showing the hormone concentration versus time for the animals of Group 1, Group 2 and Group 3.

FIG. 14. LS Means of hormone concentrations by antibody response group as determined by radioimmunoassay (RIA). FIG. 14A=growth hormone (GH); FIG. 14B=insulin-like growth factor-I (IGF-I); FIG. 14C=Cortisol. Group 1=high measurable response in serum; Group 2=lack of measurable response to immunization postpartum (week 0); Group 3=lack of measurable response to immunization pre- and postpartum; Pop=population mean. Animal classification is based on serum antibody response to ovalbumin (OVA). Nat. log.=natural logarithm. Significant differences between animals in the three groups are indicated by different letters above standard error bars (P≦0.05).

Figure 15:
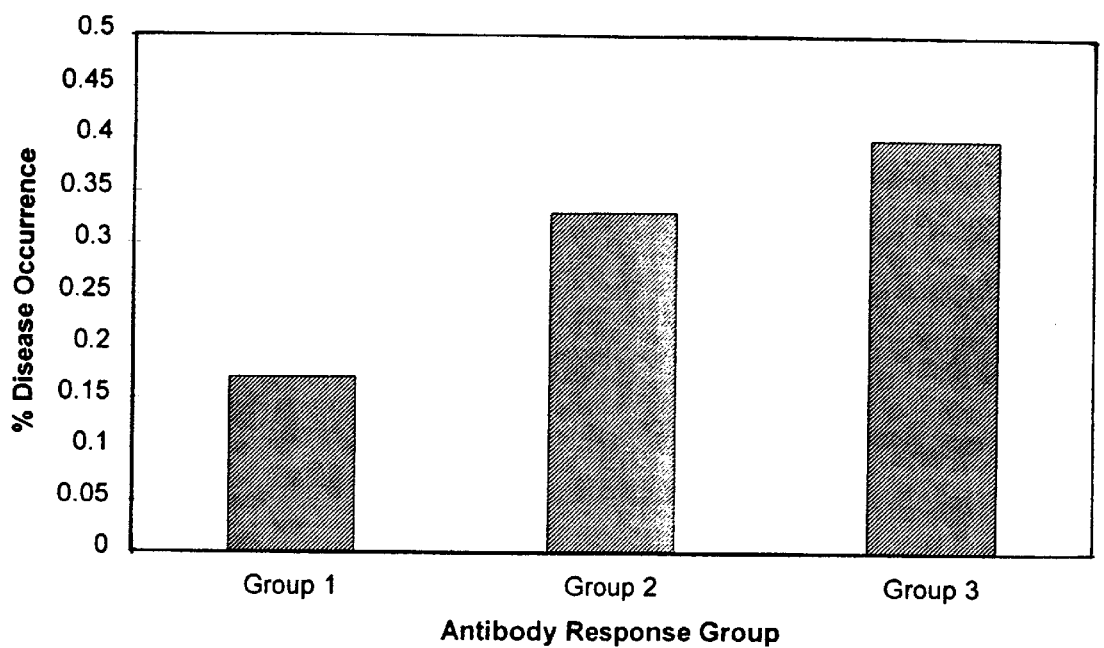
FIG. 15 is a bar graph showing the percentage disease occurrence and the antibody response in the animals of Group 1, Group 2 and Group 3.

FIG. 15. Percent disease occurrence by antibody response group. Group 1=high measurable response in serum; Group 2=lack of measurable response to immunization postpartum (week 0); Group 3=lack of measurable response to immunization pre- and postpartum. Animal classification is based on serum antibody response to ovalbumin (OVA).

TABLE 1

Analysis of variance of antibody response to ovalbumin (OVA) and E. coli J5, and the concentration of immunoglobulin $G_{1\&2}$ in serum and whey
Source of Variation

| Dependent Variable | $R^{2a}$ (%) | C.V.[b] (%) | Cow (Group)[c] | Week | Group[d] | Group* W |
|---|---|---|---|---|---|---|
| Antibody Response | | | | | | |
| Serum anti-OVA | 88.31 | 21.66 | 0.0001 | 0.0001 | 0.0001 | 0.0001 |
| Whey anti-OVA | 74.97 | −127.86 | 0.0001 | 0.0001 | 0.0001 | 0.09 |
| Serum anti-E. Coli | 78.29 | −60.42 | 0.0001 | 0.0001 | 0.0001 | ns[f] |
| Immunoglobulin concentration | | | | | | |
| Serum $IgG_1$ | 64.91 | 6.97 | ns | 0.0001 | ns | ns |
| Serum $IgG_2$ | 67.19 | 4.22 | ns | 0.0001 | 0.0001 | 0.004 |
| Whey $IgG_1$ | 87.16 | 18.92 | ns | 0.0001 | ns | ns |
| Whey $IgG_2$ | 95.11 | 14.15 | ns | 0.0001 | ns | ns |

[a] $R^2$ = coefficient of determination
[b] C.V. = coefficient of variation
[c] Cow(Group) = Cow nested within group
[d] Group = variation due to antibody response group in which cows are classified as high or low responders based on antibody response to OVA
[e] negative C.V. are from log-transformed data
[f] ns = not significant

TABLE 2

Analysis of variance of antibody response to ovalbumin (OVA) and E. coli J5, the concentration of immunoglobulin $G_{1\&2}$ in serum and whey, and somatic cell score (SCS)
Source of Variation

| Dependent Variable | $R^{2a}$ (%) | C.V.[b] (%) | Herd | Season-yr[c] | Cow[d] | Group[e] | Parity | Group* parity | Week | Group* Week | Parity* Week |
|---|---|---|---|---|---|---|---|---|---|---|---|
| Antibody Response | | | | | | | | | | | |
| Serum anti-OVA | 79.41 | 27.63 | — | — | 0.0001 | 0.0001 | 0.096 | ns[f] | 0.0001 | 0.0001 | — |
| Whey anti-OVA | 73.73 | 32.16 | 0.02 | — | 0.0001 | 0.0001 | ns | ns | 0.0001 | ns | — |
| Herd 1 | 75.34 | — | — | — | 0.0001 | 0.0001 | 0.0001 | — | 0.0001 | 0.05 | — |
| | | 130.01 h | | | | | | | | | |
| Herd 2 | 71.29 | −524.16 | — | — | 0.0001 | 0.007 | — | — | 0.0001 | 0.07 | — |
| Herd 3 | 82.72 | 6682.1 | — | — | 0.0001 | 0.0002 | — | — | 0.0001 | ns | — |
| Serum anti-E. coli | 74.23 | −43.72 | 0.003 | — | 0.0001 | — | 0.0004 | — | 0.0001 | — | 0.0001 |
| Herd 1 | 78.63 | −54.79 | — | — | 0.0001 | ns | — | — | 0.0001 | 0.06 | — |
| Herd 2 | 76.89 | −45.16 | — | — | 0.0001 | ns | 0.0001 | 0.0001 | 0.0001 | ns | — |
| Herd 3 | 70.63 | −31.53 | — | — | 0.0001 | ns | — | — | 0.0001 | 0.002 | — |

TABLE 2-continued

Analysis of variance of antibody response to ovalbumin (OVA) and *E. coli* J5, the concentration of immunoglobulin $G_{1\&2}$ in serum and whey, and somatic cell score (SCS)

Source of Variation

| Dependent Variable | $R^{2a}$ (%) | $C.V.^b$ (%) | Herd | Season-yr[c] | Cow[d] | Group[e] | Parity | Group*parity | Week | Group*Week | Parity*Week |
|---|---|---|---|---|---|---|---|---|---|---|---|
| Immunoglobulin Concentration | | | | | | | | | | | |
| Serum $IgG_1$ | 49.74 | 7.53 | — | — | ns | 0.07 | ns | ns | 0.0001 | ns | — |
| Serum $IgG_2$ | 63.14 | 4.34 | 0.0001 | — | 0.0001 | ns | 0.04 | ns | 0.025 | ns | — |
| Herd 1 | 59.97 | 4.67 | — | — | 0.02 | ns | — | — | 0.0015 | ns | — |
| Herd 2 | 48.49 | 4.36 | — | — | 0.021 | 0.08 | ns | 0.08 | ns | ns | — |
| Herd 3 | 56.14 | 3.7 | — | — | 0.005 | — | 0.04 | — | 0.09 | — | ns |
| Whey $IgG_1$ | 90.1 | 15.11 | — | — | ns | ns | 0.01 | ns | 0.0001 | ns | — |
| Whey $IgG_2$ | 96.85 | 13.5 | 0.03 | — | ns | ns | 0.0009 | ns | 0.0001 | ns | — |
| Herd 1 | 94.85 | 14.96 | — | — | ns | ns | — | — | 0.0009 | ns | — |
| Herd 2 | ns | ns | — | — | ns | ns | 0.08 | ns | 0.02 | ns | — |
| Herd 3 | 97.41 | 12.94 | — | — | ns | 0.097 | — | — | 0.0001 | ns | — |
| Somatic Cell Score | | | | | | | | | | | |
| SCS(Herd 1) | 83.51 | 44.89 | — | — | 0.0001 | ns | — | — | 0.0013 | ns | — |
| SCS(Herd 2) | 81.43 | 46.7 | — | — | 0.0001 | ns | — | — | 0.0001 | ns | — |
| SCS(Herd 3) | 78.84 | 26.54 | — | — | 0.0001 | ns | — | — | ns | ns | -- |

[a] $R^2$ = coefficient of determination
[b] C.V. = coefficient of variation
[c] Season-Year = season and year of calving
[d] Cow nested or 'grouped' within the interaction between antibody response group and parity, i.e. Cow(group*parity). If parity is not significant, parity is removed and the model becomes cow nested within antibody response group only.
[e] Group = variation due to antibody response group in which cows are classified as high or low responders based on antibody response to OVA
[f] ns = not significant
[g] ------ = not significant therefore removed and no longer relevant to that dependent variable
[h] Coefficient of variation is negative due to analysis of variance of natural logarithm transformed data

TABLE 3

Percent Occurrence (%) of clinical mastitis by antibody response group within herd

| Herd | | % Occurrence of Mastitis within an Antibody Response Group | | | Overall Mastitis Frequency by Herd |
|---|---|---|---|---|---|
| | | Group 1 | Group 2 | Group 3 | |
| Herd 1 | # of animals | n = 4 | n = 22 | n = 6 | n = 32 |
| | % with mastitis | 0 | 21.7 | 33.3 | 21.2 |
| Herd 2 | # of animals | n = 13 | n = 47 | n = 7 | n = 67 |
| | % with mastitis | 15.4 | 2.1 | 0 | 4.5 |
| Herd 3 | # of animals | n = 1 | n = 26 | n = 10 | n = 37 |
| | % with mastitis | 0 | 11.5 | 10 | 10.8 |
| All herds | # of animals | n = 18 | n = 95 | n = 23 | n = 136 |
| | % Overall Mastitis Frequency by Group | 11.1 | 9.3 | 13.6 | — |

TABLE 4

Analysis of Variance of lymphocyte proliferation to ovalbumin (OVA) and concanavalin A (Con A), lymphocyte and neutrophil number, delayed type hypersensitivity and somatic cell score

| Dependent Variable | R2[a] (%) | CV[b] | Herd | Season-Year[c] | Cow[d] | Group[e] | Parity | Group *Parity | Week | Group *Week | Parity* Week |
|---|---|---|---|---|---|---|---|---|---|---|---|
| Lymphocyte Proliferation | | | | | | | | | | | |
| Unstimulated | 58.69 | 11.5 | --[f] | -- | 0.0001 | ns[g] | ns | 0.0001 | 0.0001 | 0.05 | -- |
| OVA | 85.75 | 6.34 | -- | -- | 0.0001 | 0.01 | 0.0006 | 0.0001 | ns | 0.009 | -- |
| Con A | 67.2 | 5.15 | -- | -- | 0.0001 | ns | 0.004 | 0.0001 | 0.0001 | 0.0002 | -- |
| Complete Blood Cell Counts | | | | | | | | | | | |
| Lymphocytes | 83.16 | 17.31 | -- | -- | 0.0001 | ns | 0.0001 | 0.0001 | 0.08 | ns | -- |
| Segmented Neutrophils | 37.42 | 2.81 | -- | -- | 0.003 | ns | ns | ns | ns | ns | -- |
| Banded Neutrophils | ns | ns | -- | -- | ns | ns | ns | ns | ns | ns | -- |
| Somatic Cell Score | | | | | | | | | | | |
| Herd 1 | 83.5 | 44.89 | -- | -- | 0.0001 | ns | -- | -- | 0.001 | ns | -- |
| Herd 2 | 81.43 | 46.7 | -- | -- | 0.0001 | ns | -- | -- | 0.0001 | ns | -- |
| Herd 3 | 78.84 | 26.54 | -- | -- | 0.0001 | ns | -- | -- | ns | ns | -- |

[a]$R^2$ = coefficient of determination
[b]CV = coefficient of variation
[c]Season-Year = season and year of calving
[d]Cow nested or 'grouped' within the interaction term between antibody response group and parity i.e. cow (Group*parity). If parity is not significant, it is removed and the cow term then becomes 'grouped' within antibody response group
[e]Group = variation due to antibody response group in which cows are classified as high or low responders based on antibody response to OVA
[f]-- = not relevant to that dependent variable and therefore removed from the model
[g]ns = not significant

TABLE 5

Correlation analysis of antibody to ovalbumin (OVA) with unstimulated and stimulated lymphocyte proliferation to OVA and concanavalin A (Con A), and cutaneous delayed type hypersensitivity (DTH) response to purified protein derivative (PPD) of *M. tuberculosis*.

| Dependent Variable | Independent Variable | $r^2$ | P-value |
|---|---|---|---|
| Unstimulated Lymphocyte Proliferation | Antibody to OVA | −0.26 | 0.0001 |
| OVA-Stimulated Lymphocyte Proliferation | Antibody to OVA | −0.27 | 0.0001 |
| Con A-Stimulated Proliferation | Antibody to OVA | −0.14 | 0.0001 |
| DTH - 48 hours | Antibody to OVA | ns | ns |
| DTH - 72 hours | Antibody to OVA | ns | ns |

TABLE 6

Analysis of Variance (ANOVA) of projected 305-day milk, protein and fat yields

| Dependent Variable | R2[a](%) | CV[b] | Herd | Season-Year[c] | Group[d] | Parity | Group *Parity |
|---|---|---|---|---|---|---|---|
| Milk yield | 19.5 | 14.98 | --[e] | -- | 0.06 | 0.0001 | 0.0001 |
| Protein yield | 15.26 | 14.76 | -- | -- | 0.0001 | 0.0001 | 0.0001 |
| Fat Yield | 17.51 | 13.53 | -- | -- | 0.0001 | 0.0001 | 0.0001 |

[a]$R^2$ = coefficient of determination
[b]CV = coefficient of variation
[c]Season-Year = season and year of calving
[d]Group = variation due to antibody response group in which cows are classified as high or low responders based on antibody response to OVA
[e]-- = not relevant to that dependent variable and therefore removed from the model

TABLE 7

Analysis of variance of antibody response to ovalbumin (OVA) and E. coli J5, and the concentration of immunoglobulin $G_{1\&2}$ in serum and whey Source of Variation

| Dependent Variable | $R^{2a}$ (%) | $C.V.^b$ (%) | Cow (Group)[c] | Week | Group[d] | Group * Week | $GH^e$ | GH* Week | IGF-I[f] | IGF-I* Week | Cort[g] | Cort* week |
|---|---|---|---|---|---|---|---|---|---|---|---|---|
| Antibody Response | | | | | | | | | | | | |
| Serum OVA | 94.19 | 14.01 | 0.0001 | ns[h] | 0.005 | 0.0001 | 0.15 | ns | ns | ns | ns | ns |
| Whey OVA | 83.81 | 37.36 | 0.006 | 0.06 | 0.003 | ns | ns | ns | 0.12 | 0.005 | ns | ns |
| E. coli | 79.1 | 97.18 | 0.0002 | ns | ns | ns | ns | ns | ns | ns | ns | ns |
| Immunoglobulin | | | | | | | | | | | | |
| Serum $IgG_1$ | 73.17 | 7.88 | ns | ns | ns | ns | ns | ns | ns | ns | ns | ns |
| Serum $IgG_2$ | 75.47 | 4.63 | ns | ns | 0.001 | ns | ns | ns | ns | ns | ns | ns |
| Whey $IgG_1$ | 94.66 | 16.46 | ns | ns | ns | ns | ns | ns | 0.07 | ns | ns | ns |
| Whey $IgG_2$ | 87.25 | 30.92 | ns | ------[i] | ns | ------- | ns | ------- | ns | ------- | ns | ------- |

[a] $R^2$ = coefficient of determination
[b] C.V. = coefficient of variation
[c] Cow(Group) = Cow nested within group
[d] Group = variation due to antibody response group in which cows are classified as high or low responders based on antibody response to OVA
[e,f,g] = growth hormone, insulin-like growth factor-I, cortisol,
[h] ns = not significant
[i] ------ = not relevant to that dependent variable

TABLE 8

Correlation analysis of hormone concentration with antibody response to ovalbumin (OVA), and E. coli J5, and the concentration of $IgG_{1\&2}$ in serum and whey

| Dependent Variable | Independent Variable | $r^{2a}$ | P value |
|---|---|---|---|
| Antibody Response | | | |
| Serum OVA | GH[b] | 0.29 | 0.001 |
| | IGF-I[c] | −0.19 | 0.04 |
| | Cortisol[d] | 0.17 | 0.06 |
| Whey OVA | GH | 0.31 | 0.0005 |
| | IGF-I | −0.22 | 0.01 |
| | Cortisol | — | ns |
| E. coli J5 | GH | 0.18 | 0.04 |
| | IGF-I | — | ns |
| | Cortisol | — | ns |
| Radial Immunodiffusion | | | |
| Serum $IgG_1$ | GH | −0.26 | 0.01 |
| | IGF-I | 0.19 | 0.07 |
| | Cortisol | — | ns |
| Serum $IgG_2$ | GH | — | ns |
| | IGF-I | — | ns |
| | Cortisol | — | ns |
| Whey $IgG_1$ | GH | 0.26 | 0.03 |
| | IGF-I | −0.2 | 0.1 |
| | Cortisol | — | ns |
| Whey IgG2 | GH | — | ns |
| | IGF-I | — | ns |
| | Cortisol | — | ns |

[a] $r^2$ = SAS Pearson Product Moment Correlation Coefficient
[b, c, d] = growth hormone, insulin-like growth factor-I, cortisol

We claim:

1. A method of ranking the immune response of a test animal within a population of animals under a stress of periparturition comprising:

(a) immunizing the animals with at least one antigen at least once before onset of the stress and at least once during the stress; and (b) for each of the animals within the population, measuring an antibody response to the at least one antigen at least once before the onset of the stress and at least three times during the stress, and at least once after the stress (c) calculating the mathematical index of the antibody response wherein the mathematical index is: y=primary response+secondary response+tertiary response+quaternary response wherein, (i) y is the total antibody response;

(ii) the primary response is the difference in antibody quantity at a first period of time preperipartum and at a second period of time prepartum, wherein the animal is immunized at the first period of time preperipartum;

(iii) the secondary response is the difference in antibody quantity at the second period of time prepartum and at about parturition, wherein the animal is immunized at the second period of time prepartum;

(iv) the tertiary response is the difference in antibody quantity at about parturition and at a first period of time postpartum, wherein the animal is immunized at about parturition; and (v) the quaternary response is the difference in antibody quantity at the first period of time postpartum and a second period of time post peripartum, wherein animals exhibiting negative secondary or tertiary responses are weighted with a positive coefficient and the test animal having a y value greater than about one standard deviation above the average of the population is a high immune responder.

2. A method according to claim 1 wherein the antigen is selected from the group consisting of hen egg white lysozyme, human serum albumin, tyrosine-glutamine-alanine-lysine (SEQ.ID.NO.1) copolymer, and ovalbumin.

3. A method according to claim 2 wherein the antigen is ovalbumin.

4. A method according to claim 1 wherein the antigen is formulated into a vaccine.

5. A method according to claim 1 wherein a source for measuring antibody response is selected from the group consisting of milk and blood.

* * * * *

SEQUENCE LISTING

<160> NUMBER OF SEQ ID NOS: 1

<210> SEQ ID NO 1
<211> LENGTH: 4
<212> TYPE: PRT
<213> ORGANISM: synthetic construct

<400> SEQUENCE: 1

Tyr Gln Ala Lys